United States Patent [19]
Gilliam et al.

[11] Patent Number: 6,068,975
[45] Date of Patent: *May 30, 2000

[54] ISOLATION AND USES OF A WILSON'S DISEASE GENE

[75] Inventors: T. Conrad Gilliam, New York, N.Y.; Rudolph E. Tanzi, Canton, Mass.

[73] Assignees: The Trustees of Columbia University in the City of New York, New York, N.Y.; General Hospital Corporation, Boston, Mass.

[ * ] Notice: This patent is subject to a terminal disclaimer.

[21] Appl. No.: 08/338,579

[22] PCT Filed: Sep. 1, 1994

[86] PCT No.: PCT/US94/09851

§ 371 Date: Jun. 17, 1996

§ 102(e) Date: Jun. 17, 1996

[87] PCT Pub. No.: WO95/06714

PCT Pub. Date: Mar. 9, 1995

Related U.S. Application Data

[63] Continuation-in-part of application No. 08/118,441, Sep. 1, 1993, Pat. No. 5,578,493.

[51] Int. Cl.$^7$ .............................. C12Q 1/68; C12P 21/00; C12N 5/00; C07H 21/04
[52] U.S. Cl. .......................... 435/6; 435/69.1; 435/91.4; 435/320.1; 435/325; 536/23.5
[58] Field of Search .............................. 435/6, 69.1, 91.4, 435/325, 320.1; 536/23.5

[56] References Cited

PUBLICATIONS

Hodgson TGeh vector void in Gene therapy. Can viral vectors and transfection be combined to permit sate, efficacious, and targeted gene therapy? Bio/technology vol. 13:222–225, Mar. 1995.
Orkin et al. Report and recommendations of the panel to assess the NIH investment in research on gene therapy, Dec. 7, 1995.
Weatherall Scope and limitations of gene therapy. British Medical Bulletin vol. 51(1):1–11, Jan. 1995.
Adams, M.D. et al. (1993) *Nature Genetics* 4:373–380 (Exhibit 1).
Altshul, S.F. et al. (1990) *J. Mol. Biol.* 215(3):403–410 (Exhibit 2).
Bonne–Tamir, B. et al. (1986) *Genet. Epidemiol.* 3(3):201–209 (Exhibit 3).
Bowcock, A.M. et al. (1987) *Am. J. Hum. Genet.* 41(1):27–35 (Exhibit 4).
Bull, P.C. et al. (1993) *Nature Genetics* 5:327–336.
Chelly, J. and Monaco, A.P. (1993) *Nature Genetics* 5:317–318.
Chelly, J. (1993) *Nature Genetics* 3:14–19.
Farrer, L.A. et al. (1991) *Neurology* 41(7):992–999 (Exhibit 5).
Figus, A. et al. (1995) *J. Hum. Genet.* 57(6):1318–1324 (Exhibit 6).
Frydman, M. et al. (1985) *Proc. Natl. Acad.Sci. USA* 82:1819–1821 (Exhibit 7).
Fujimura, F.K. (1991) *Clin. Biochem.* 24(4):353–361 (Exhibit 8).
Houwen, R.H.J. et al. (1995) *J. Med. Genet.* 32:480–483 (Exhibit 9).
Kooy, R.F. (1993) *Human Genetics* 91:504–506.
Lutsenko, S. and Kaplan, J.H. (1994) *J. Biol. Chem.* 269(6):4555–4564 (Exhibit 10).
Mercer, J.F.B. et al. (1993) *Nature Genetics* 3:20–25.
Morral, N. et al. (1993) *Hum. Mol. Genet.* 2(7):1015–1022 (Exhibit 11).
Pellequer, J.–L. et al. (1993) *Immunol. Lett.* 36(1):83–99 (Exhibit 12).
Petrukhin, K.E. et al. (1993) *Genomics* 15(1):76–85 (Exhibit 13).
Petrukhin, K.E. et al. (1994) *Hum. Mol. Genet.* 3(9):1647–1656 (Exhibit 14).
Petrukhin, K.E. et al. (1993) *Nature Genetics* 5:338–343.
Shimizu, N. et al. (1995) *Biochem. Biophys. Res. Comm.* 217(1):16–20 (Exhibit 15).
Silver, S. et al. (1993) *Mol. Microbiol.* 10(1):7–12 (Exhibit 16).
Tanzi, R.E. et al. (1993) *Nat. Genet.* 5:344–350.
Thomas, G.R. et al. (1995) *Nat. Genet.* 9:210–217 (Exhibit 17).
Thomas, G.R. et al. (1994) *Am. J. Hum. Genet.* 54(1):71–78 (Exhibit 18).
Toyofuku, T. et al. (1993) *J. Biol. Chem.* 268(4):2809–2815 (Exhibit 19).
Toyofuku, T. et al. (1992) *J. Biol. Chem.* 267(20):14490–14496 (Exhibit 20).
Vulpe, C. et al. (1993) *Nature Genetics* 3:7–13.
Watson, F. (1993) *TibTech* 11:114–117.
Wu, J. (1994) *Nat. Genet.* 7:541–545 (Exhibit 21).
Yamaguchi, Y. et al. (1993) *Biochem. Biophys. Res. Comm.* 197(1):271–277.
Yuan, D.S. (1995) *Proc. Natl. Acad. Sci USA* 92:2632–2636 (Exhibit 22).

*Primary Examiner*—John S. Brusca
*Assistant Examiner*—William Sandals
*Attorney, Agent, or Firm*—John P. White; Cooper & Dunham LLP

[57] ABSTRACT

This invention provides an isolated, vertebrate nucleic acid molecule encoding the normal protein that prevents development of Wilson's disease. This invention also provides a nucleic acid molecule comprising a nucleic acid molecule of at least 15 nucleotides capable of specifically hybridizing with a sequence included within the sequence of the above-described nucleic acid molecule. Finally, this invention provides various uses of the isolated Wilson's disease gene.

10 Claims, 27 Drawing Sheets

A. Probe: 3a3 (arrow)
Positives: 3a4, 2a2, 5b3

B. Probe: 3a4 (arrow)
Positives: 3a3, 2a2, 5b3

C. Probe: 2a2 (arrow)
Positives: 3a3, 3a4, 5b3

D. Probe: 5b3 (arrow)
Positives: 3a3, 3a4, 2a2, 4b2

E. Probe: 4b2 (arrow)
Positives: 5b3, 4b4

F. Probe: 4b4 (arrow)
Positives: 4b2, 5a5

G. Probe: 5a5 (arrow)
Positive: 4b4

FIG. 5-1

```
1                                              GTGGAGGGCATGACC
                                               V  E  G  M  T    5
 16 TGCCAGTCCTGTGTCAGCTCCATTGAAGGCAAGGTCCGGAAACTGCAAGGA
     C  Q  S  C  V  S  S  I  E  G  K  V  R  K  L  Q  G   22
 67 GTAGTGAGAGTCAAAGTCTCACTCAGCAACCAAGAGGCCGTCATCACTTAT
     V  V  R  V  K  V  S  L  S  N  Q  E  A  V  I  T  Y   39
118 CAGCCTTATCTCATTCAGCCCGAAGACCTCAGGGACCATGTAAATGACATG
     Q  P  Y  L  I  Q  P  E  D  L  R  D  H  V  N  D  M   56
169 GGATTTGAAGCTGCCATCAAGAGCAAAGTGGCTCCCTTAAGCCTGGGACCA
     G  F  E  A  A  I  K  S  K  V  A  P  L  S  L  G  P   73
220 ATTGATATTGAGCGGTTACAAAGCACTAACCCAAAGAGACCTTTATCTTCT
     I  D  I  E  R  L  Q  S  T  N  P  K  R  P  L  S  S   90
271 GCTAACCAGAATTTTAATAATTCTGAGACCTTGGGGCACCAAGGAAGCCAT
     A  N  Q  N  F  N  N  S  E  T  L  G  H  Q  G  S  H  107
322 GTGGTCACCCTCCAACTGAGAATAGATGGAATGCATTGTAAGTCTTGCGTC
     V  V  T  L  Q  L  R  I  D  G  M  H  C  K  S  C  V  124
373 TTGAATATTGAAGAAAATATTGGCCAGCTCCTAGGGGTTCAAAGTATTCAA
     L  N  I  E  E  N  I  G  Q  L  L  G  V  Q  S  I  Q  141
424 GTGTCCTTGGAGAACAAAACTGCCCAAGTAAAGTATGACCCTTCTTGTACC
     V  S  L  E  N  K  T  A  Q  V  K  Y  D  P  S  C  T  158
475 AGCCCAGTGGCTCTGCAGAGGGCTATCGAGGCACTTCCACCTGGGAATTTT
     S  P  V  A  L  Q  R  A  I  E  A  L  P  P  G  N  F  175
526 AAAGTTTCTCTTCCTGATGGAGCCGAAGGGAGTGGGACAGATCACAGGTCT
     K  V  S  L  P  D  G  A  E  G  S  G  T  D  H  R  S  192
577 TCCAGTTCTCATTCCCCTGGCTCCCCACCGAGAAACCAGGTCCAGGGCACA
     S  S  S  H  S  P  G  S  P  P  R  N  Q  V  Q  G  T  209
628 TGCAGTACCACTCTGATTGCCATTGCCGGCATGACCTGTGCATCCTGTGTC
     C  S  T  T  L  I  A  I  A  G  M  T  C  A  S  C  V  226
679 CATTCCATTGAAGGCATGATCTCCCAACTGGAAGGGGTGCAGCAAATATCG
     H  S  I  E  G  M  I  S  Q  L  E  G  V  Q  Q  I  S  243
730 GTGTCTTTGGCCGAAGGGACTGCAACAGTTCTTTATAATCCCTCTGTAATT
     V  S  L  A  E  G  T  A  T  V  L  Y  N  P  S  V  I  260
781 AGCCCAGAAGAACTCAGAGCTGCTATAGAAGACATGGGATTTGAGGCTTCA
     S  P  E  E  L  R  A  A  I  E  D  M  G  F  E  A  S  277
832 GTCGTTTCTGAAAGCTGTTCTACTAACCCTCTTGGAAACCACAGTGCTGGG
     V  V  S  E  S  C  S  T  N  P  L  G  N  H  S  A  G  294
883 AATTCCATGGTGCAAACTACAGATGGTACACCTACATCTGTCCAGGAAGTG
     N  S  M  V  Q  T  T  D  G  T  P  T  S  V  Q  E  V  311
934 GCTCCCCACACTGGGAGGCTCCCTGCAAACCATGCCCCGGACATCTTGGCA
     A  P  H  T  G  R  L  P  A  N  H  A  P  D  I  L  A  328
985 AAGTCCCCACAATCAACCAGAGCAGTGGCACCGCAGAAGTGCTTCTTACAG
```

FIG. 5-2

```
          K   S   P   Q   S   T   R   A   V   A   P   Q   K   C   F   L   Q    345
1236 ATCAAAGGCATGACCTGTGCATCCTGTGTGTCTAACATAGAAAGGAATCTG
         I   K   G   M   T   C   A   S   C   V   S   N   I   E   R   N   L    362
1287 CAGAAAGAAGCTGGTGTTCTCTCCGTGTTGGTTGCCTTGATGGCAGGAAAG
          Q   K   E   A   G   V   L   S   V   L   V   A   L   M   A   G   K    379
1338 GCAGAGATCAAGTATGACCCAGAGGTCATCCAGCCCCTCGAGATAGCTCAG
          A   E   I   K   Y   D   P   E   V   I   Q   P   L   E   I   A   Q    396
1389 TTCATCCAGGACCTGGGTTTTGAGGCAGCAGTCATGGAGGACTACGCAGGC
          F   I   Q   D   L   G   F   E   A   A   V   M   E   D   Y   A   G    413
1440 TCCGATGGCAACATTGAGCTGACAATCACAGGGATGACCTGCGCGTCCTGT
          S   D   G   N   I   E   L   T   I   T   G   M   T   C   A   S   C    430
1491 GTCCACAACATAGAGTCCAAACTCACGAGGACAAATGGCATCACTTATGCC
          V   H   N   I   E   S   K   L   T   R   T   N   G   I   T   Y   A    447
1542 TCCGTTGCCCTTGCCACCAGCAAAGCCCTTGTTAAGTTTGACCCGGAAATT
          S   V   A   L   A   T   S   K   A   L   V   K   F   D   P   E   I    464
1593 ATCGGTCCACGGGATATTATCAAAATTATTGAGAGCAAACCTCAGAAGCC
          I   G   P   R   D   I   I   K   I   I   E   S   K   T   S   E   A    481
1644 CTGGCTAAACTCATGTCTCTCCAAGCCACAGAAGCCACCGTTGTGACCCTT
          L   A   K   L   M   S   L   Q   A   T   E   A   T   V   V   T   L    498
1695 GGTGAGGACAATTTAATCATCAGGGAGGAGCAAGTCCCCATGGAGCTGGTG
          G   E   D   N   L   I   I   R   E   E   Q   V   P   M   E   L   V    515
1746 CAGCGGGGCGATATCGTCAAGGTGGTCCCTGGGGGAAAGTTTCCAGTGGAT
          Q   R   G   D   I   V   K   V   V   P   G   G   K   F   P   V   D    532
1797 GGGAAAGTCCTGGAAGGCAATACCATGGCTGATGAGTCCCTCATCACAGGA
          G   K   V   L   E   G   N   T   M   A   D   E   S   L   I   T   G    549
1848 GAAGCCATGCCAGTCACTAAGAAACCCGGAAGCACTGTAATTGCGAGGTCT
          E   A   M   P   V   T   K   K   P   G   S   T   V   I   A   R   S    566
1899 ATAAATGCACATGGCTCTGTGCTCATTAAAGCTACCCACGTGGGCAATGAC
          I   N   A   H   G   S   V   L   I   K   A   T   H   V   G   N   D    583
1950 ACCACTTTGGCTCAGATTGTGAAACTGGTGGAAGAGGCTCAGATGTCAAAG
          T   T   L   A   Q   I   V   K   L   V   E   E   A   Q   M   S   K    600
2001 AACCCCAACAAGCACATCTCCCAGACAGAGGTGATCATCCGGTTTGCTTTC
          N   P   N   K   H   I   S   Q   T   E   V   I   I   R   F   A   F    617
2052 CAGACGTCCATCACGGTGCTGTGCATTGCCTGCCCCTGCTCCCTGGGGCTG
          Q   T   S   I   T   V   L   C   I   A   C   P   C   S   L   G   L    634
2103 GCCACGCCCACGGCTGTCATGGTGGGCACCGGGGTGGCCGCGCAGAACGGC
          A   T   P   T   A   V   M   V   G   T   G   V   A   A   Q   N   G    651
2154 ATCCTCATCAAGGGAGGCAAGCCCCTGGAGATGGCGCACAAGATAAAGACT
          I   L   I   K   G   G   K   P   L   E   M   A   H   K   I   K   T    668
2205 GTGATGTTTGACAAGACTGGCACCATTACCCATGGCGTCCCCAGGGTCATG
          V   M   F   D   K   T   G   T   I   T   H   G   V   P   R   V   M    685
2256 CGGGTGCTCCTGCTGGGGGATGTGGCCACACTGCCCCTCAGGAAGGTTCTG
          R   V   L   L   L   G   D   V   A   T   L   P   L   R   K   V   L    702
2307 GCTGTGGTGGGGACTGCGGAGGCCAGCAGTGAACACCCCTTGGGCGTGGCA
          A   V   V   G   T   A   E   A   S   S   E   H   P   L   G   V   A    719
2358 GTCACCAAATACGTAAAGAGGAACTTGGAACAGAGACCTTGGGATACTGC
```

FIG. 5-3

```
              V  T  K  Y  C  K  E  E  L  G  T  E  T  L  G  Y  C      736
2209 ACGGACTTCCAGGCAGTGCCAGGCTGTGGAATTGGGTGCAAAGTCAGCAAC
        T  D  F  Q  A  V  P  G  C  G  I  G  C  K  V  S  N         753
2260 GTGGAAGGCATCCTGGCCCACAGTGAGCGCCCTTTGAGTGCAACGGCCAGT
        V  E  G  I  L  A  H  S  E  R  P  L  S  A  P  A  S         770
2311 CACCTGAATGAGGCTGGCAGCCTTCCCGCAGAAAAAGATGCAGTCCCCCAG
        H  L  N  E  A  G  S  L  P  A  E  K  D  A  V  P  Q         787
2362 ACCTTCTCTGTGCTGATTGGAAACCGTGAGTGGCTGAGGCGCAACGGTTTA
        T  F  S  V  L  I  G  N  R  E  W  L  R  R  N  G           804
2413 ACCATTTCTAGCGATGTCAGCGACGCTATGACAGACCACGAGATGAAAGGA
        T  I  S  S  D  V  S  D  A  M  T  D  H  E  M  K    G      821
2464 CAGACAGCCATCCTGGTGGCTATTGACGGTGTGCTCTGTGGGATGATCGCA
        Q  T  A  I  L  V  A  I  D  G  V  L  C  G  M  I  A         838
2515 ATCGCAGACGCTGTCAAGCAGGAGGCTGCCCTGGCTGTGCACACGCTGCAG
        I  A  D  A  V  K  Q  E  A  A  L  A  V  H  T  L  Q         855
2566 AGCATGGGTGTGGACGTGGTTCTGATCACGGGGGACAACCGGAAGACAGCC
        S  M  G  V  D  V  V  L  I  T  G  D  N  R  K  T  A         872
2617 AGAGCTATTGCCACCCAGGTTGGCATCAACAAAGTCTTTGCAGAGGTGCTG
        R  A  I  A  T  Q  V  G  I  N  K  V  F  A  E  V  L         889
2668 CCTTCGCACAAGGTGGCCAAGGTCCAGGAGCTCCAGAATAAAGGGAAGAAA
        P  S  H  K  V  A  K  V  Q  E  L  Q  N  K  G  K  K         906
2719 GTCGCCATGGTGGGGGATGGGGTCAATGACTCCCCGGCCTTGGCCCAGGCA
        V  A  M  V  G  D  G  V  N  D  S  P  A  L  A  Q  A         923
2770 GACATGGGTGTGGCCATTGGCACCGGCACGGATGTGGCCATCGAGGCAGCC
        D  M  G  V  A  I  G  T  G  T  D  V  A  I  E  A  A         940
2821 GACGTCGTCCTTATCAGAAATGATTTGCTGGATGTGGTGGCTAGCATTCAC
        D  V  V  L  I  R  N  D  L  L  D  V  V  A  S  I  H         957
2872 CTTTCCAAGAGGACTGTCCGAAGGATACGCATCAACCTGGTCCTGGCACTG
        L  S  K  R  T  V  R  R  I  R  I  N  L  V  L  A  L         974
2923 ATTTATAACCTGGTTGGGATACCCATTGCAGCAGGTGTCTTCATGCCCATC
                    I  Y  N  L  V  G  I  P  I  A  A  G  V  F  M  P  I    991
2974 GGCATTGTGCTGCAGCCCTGGATGGGCTCAGCGGCCATGGCAGCCTCCTCT
                  G  I  V  L  Q  P  W  M  G  S  A  A  M  A  A  S  S   1008
3025 GTGTCTGTGGTGCTCTCATCCCTGCAGCTCAAGTGCTATAAGAAGCCTGAC
                V  S  V  V  L  S  S  L  Q  L  K  C  Y  K  K  P  D      1025
3076 CTGGAGAGGTATGAGGCACAGGCGCATGGCCACATGAAGCCCCTGACGGCA
        L  E  R  Y  E  A  Q  A  H  G  H  M  K  P  L  T  A        1042
3127 TCCCAGGTCAGTGTGCACATAGGCATGGATGACAGGTGGCGGGACTCCCCC
        S  Q  V  S  V  H  I  G  M  D  D  R  W  R  D  S  P        1059
3178 AGGGCCACACCATGGGACCAGGTCAGCTATGTCAGCCAGGTGTCGCTGTCC
        R  A  T  P  W  D  Q  V  S  Y  V  S  Q  V  S  L  S        1076
3229 TCCCTGACGTCCGACAAGCCATCTCGGCACAGCGCTGCAGCAGACGATGAT
        S  L  T  S  D  K  P  S  R  H  S  A  A  A  D  D  D        1093
3280 GGGGACAAGTGGTCTCTGCTCCTGAATGGCAGGGATGAGGAGCAGTACATC
```

FIG. 5-4

```
              G   D   K   W   S   L   L   L   N   G   R   D   E   E   Q   Y   I  1110
3331 T GAT GAC TTC AGG CAG GCG GGC CGG GGC AGG GAC TTG CCT CCA CTC ACC AC
        *
3382 AAGCTGAGCAGGACAGCCAGCAGCAGGATGGGCTGAGCTAGCCTCCAGCTT
3433 TGGGGACTTCCGCTCCCTGGATATGTCCAGTCATCCTGCCCTGCAGCACGC
3484 GGCCTTGTCTGGGTGCAGCTGGGCTTGGCCTGGAGAGGACGGCCCTGCCTG
3535 CCTCTTGGCCTCACGGGACCGTCAGCATGGGCTTTGTCTTGGACTCTAGTC
3586 CTTGGCTGGACTGTAGAAGGTGAGAGGCGAGTCACCCTCCTCACAGACCTC
3637 TGCTTGGAGTATTTAGGATGACTGCTGTGAAATGGAGAACAGTTTCATCAG
3688 GACCAAAAAACCTCACTGGGCCTTTCCAGAGAACTGCAGACCTCACTGTCA
3739 GGGTCTTTCTGATGACGCCTGTCTGTGCATCATGTTTCTGAGACCACAG
3790 TTTACCTCAGGTGTGCCTGTTGCTTTCTTCCTGCATAGTCTGTTCCTTTCT
3841 TCGTACATAGTCTGTTCCTTTTCTCTCCTGTGTGCTTGTCAGTGGGACCC
3892 CTCGCAACCCTGCCTGTCACCTGGGAGGGTGGGACCAATGTCCTTGTGGTC
3943 TTTGCTGCTGCTCTCAGGCGCTTCTCCAATGCTCTGGAGTGTGCATTTCAG
3994 CTTGAACCTGCTTCCTGGCTCACACATCCCCAGCCAGGGAGCTTGCCACAC
4045 TCTTCTTCAAGTTGAGGAGAGTTCTTTTTTGCTTAAAGCCCCCTTCTCCAT
4096 GGAGTGTTGGCTTCTCAATAGAGTGTTGTTGCTGACCAGCTGGAGTGAGGG
4147 CCTCAGAGCCTGACCTGAGAGTCCGTACTCGGCTTCCTGTGGGGTGTAGGT
4198 TCTCGCGATTCAGGACGTCCTTCCATATCCCTGCCCAGCCTGTGGTGCTTG
4249 AAACGTTTGCCCCATGGGAAACGTATGTGTGCAGGAGCCTCCCTGCACGGC
4300 CCAAGGGGCTTCGTTTTCAGTCTTCTGACTGTCACCTCGTGGGGTTCAGTA
4351 GAGAATTCAATTACTAGCGCCTGGCCTTGTGTGGCTTGGAGGAAATGGTAC
4402 TGCCCAAATAGGAGGAAAACACAGCCTCCCTGAGCCTGCATTCTGCACGCT
4453 GCCCAGGGGCTTCAGAAAAGGAGTGGCCACAGCACCCCGAAGGGAGCATCT
4504 ATTTACCTGGCAGTGGCTCTCAGAGCAGCAGAACGGGTTCAGTTTTAGACT
4555 CTGAAGTTGGTTGTGATTGACAGAACCCTTTGGGAGCAAACTAGTAGAGTT
4606 GGATTAAATTCTGGGTGAAACCCTTTTCTCCCACACAAAATAGTTTTAGTG
4657 ATTTTTTTCATTGTCCATTACTTGCCAGGGGCAGTTTTAGCAGCACTTTTG
4708 ATAGATTACGTCTAATCCTCCCAACCAACCAGCAGGGTAGCTATTACTGTC
4759 CACATTTTACAGGCAAGGAAACAGGCTCCAAGAGGCTGAGGACTTTGCCCA
4810 GGATGACATAGCCAATGGACAAGCAGTGTCTGTCAGCTGTGAAGGCTTCAC
4861 TCTTATTGTCCTTCTACCTTGAATAGAAGTTTTCCTGATAAGAATAAACGA
4912 GGAAAAGGTCCTTGCCTCCTGGAAGAACAAATCTACCAGGTGATCTATTCA
4963 TTGTTTCAACTCAGAATGCACTTGATTCAGGAGGTCATCTGACCTTCACCT
5014 TGGATGGTTAGTTTCACTTTTTACATATAGTTTTTGCAGGGTTTTATTTTA
5065 TAAAATCCAAGCGCGCTGTTGATTGTGTTTTCCTTGTTTTCAGCCCCCGA
5116 CTCCAGCCCGCAGCACATTTCCGCTGTCCGTCAGTAATTGTGTCCTCTCTT
5167 TATGCTTGCTTGGGAATGTTGTTTTCTGACTAGGCTGATCATTATCTAAA
5218 GAATCTAATTCTGTTGATTTTAAAACTTTTAGGACCATAAACGTTGTGTT
5269 CATATATGGACATGGAAATATTTATATAATTTTATAGAAAATAACCTTTTA
5320 GATGGTCAAAGTGTAAGGAGTTTTTTTGTCAGATAATCATTTCTACTTCAA
5371 AAACATTTCATGCAATATTAGAATAAAGTTCCTGTCATTCCTCTAAAAAAA
```

FIG. 6-1

| transduction | | | | | | | | | | | | | | |
|---|---|---|---|---|---|---|---|---|---|---|---|---|---|---|
| | * | * | * | * | * | * | * | * | * | * | * | * | * | * |
| pWD518_596 | G D | V | G | P | D G | V | G | D E S | I T G | R A | A | S | G | L V . A |
| Mc1 | G D | V | G | P | D G | V | G | D E S | I T G | E A | A | S | G | L V . A |
| CopA | D D | I | G | P | D G | I | G | D E S | L T G | E S | S | T | G | M V . A |
| K+ ATPase (E. Faecalis) | G D | V | G | P | D G | I | G | D E S | V T G | E S | S | S | G | . . . |
| Cd ATPase | G D | V | G | A | D G | I | Q | N Q A | I T G | E S | S | T | G | L V . A |
| H+/K+ ATPase | G D | V | G | A | D G | V | G | N Q T | I T G | Q E S | S | T | G | L V . A |
| FixI | G D | V | G | P | D G | V | G | D R S | V N G | E S | S | T | G | L M . A |
| K+ ATPase (E.Coli) | G D | V | G | P | D G | V | G | D E S | I T G | E S | S | S | G | M V . A |
| H+ ATPase | G D | L | G | P | D G | I | . | D Q S | I T G | E S | S | S | G | L V . A |
| ATPase S.c. | G E | L | G | P | D G | I | Q | D Q S | I T G | E S | S | S | G | L V . A |
| E1-E2 ATPase 1A | G D | L | G | P | D C | I | Q | D E A | L T G | E S | S | S | G | L L . V |

FIG. 6-2

| phospho_site | * * | * | * | * | * | * * * | * | * * * |
|---|---|---|---|---|---|---|---|---|
| PWD621_723 | I.V | CPC.L | G | E | V | DKTGTIT | G.P.V | V | E..SHPLG.AV |
| Mc1 | I.V | CPC.L | G | E | V | DKTGTIT | G.P.V | I | E..SHPLG.AI |
| CopA | V.V | CPC.L | G | E | I | DKTGTLT | G.P.V | I | E..SHPLG.AI |
| K+ ATPase (E. Faecalis) | V.V | CPH.L | S | E | I | DKTGTLT | G.F.V | I | E..AHPLA.GI |
| Cd ATPase | L.V | CPC.L | A | E | V | DKTGTLT | G.P.V | L | E..SHPLA.AI |
| H+/K+ ATPase | L.V | CPC.L | A | E | I | DKTGTLT | G.P.V | L | E..SHPLA.AI |
| FixI | V.V | CPC.L | A | E | V | DKTGTIT | G.P.L | | A..SHPIA.AI |
| K+ ATPase (E. Coli) | V.L | IPT.I | G | E | L | DKTGTIT | G | | |
| H+ ATPase 1 | L.I | VPV.L | G | E | L | DKTGTLT | N | | |
| H+ ATPase 2 | L.I | VPV.L | G | E | L | DKTGTLT | N | | |
| E1-E2 ATPase 1A | V.V | IPI.L | G | E | L | DKTGTLT | N | | |

FIG. 6-3

| ATP | | | | | | | | | | |
|---|---|---|---|---|---|---|---|---|---|---|
| | * | * | | * | * | | * | * * * | * * | * * |
| pWD836_956 | D..K | G | GD | G | A | P..K | V..M | GDGVNDSP | L | A..G..A...GTD....AD |
| Mc1 | D..K | G | GD | G | A | P..K | V..M | GDGINDSP | L | A..G..A...GTD....AD |
| CopA | D..K | G | GD | G | A | P..K | V..M | GDGINDAP | L | A..G..A...GTD....AD |
| K+ ATPase (E. Faecalis) | D..K | N | GD | G | G | P..K | V..M | GDGVNDAP | L | A..G..A...GTD....AD |
| Cd ATPase | D..R | G | GD | G | S | P..K | V..M | GDGINDAP | L | S..G..A...GTD....AD |
| H+/K+ ATPase | D..R | G | GD | G | A | P..K | V..M | GDGVNDAP | L | S..G..A...GTD....AD |
| FixI | D..R | G | GD | G | A | P..K | A..V | GDGTNDAP | L | A..S..A...AAD....AD |
| K+ ATPase (E. Coli) | D..K | G | GD | G | A | P..K | V..M | GDGINDAP | L | A..A..A...GTQ....GN |
| E1-E2 ATPase | D..R | G | GD | G | A | P..K | V..M | GDGTNDAP | L | A..G..S...GSD....AG |
| H+ ATPase 1 | D..R | G | GD | G | A | P..K | V..M | GDGVNDAP | L | A..G..A...ATD....AD |
| H+ ATPase 2 | D..R | G | GD | G | A | P..K | V..M | GDGVNDAP | L | A..G..A...ASD....AD |
| Mg++ ATPase | D..K | G | GD | G | A | P..K | V..F | GDGINDAP | L | A..G..S...AAD....SD |
| E1-E2 ATPase 1A | D..R | G | GD | D | A | | C..M | GDGVNDAP | L | A..G..A...ATD....AD |
| Ca++ ATPase | D..R | G | GD | G | | | V..V | GDGTNDGP | L | A..G..A...GTD....SD |

FIG. 6-4

| metal | | | | | | | | | | |
|---|---|---|---|---|---|---|---|---|---|---|
| | | ★ ★ | | | ★ | ★ ★ | | | | ★ |
| pWD1_60 | ..G | M T | C | C | .... E | ...... G | V | .... V | ........ | I |
| Mc1(2) | ..G | M T | C | C | .... E | ...... G | V | .... V | ........ | I |
| pWD115_174 | ..G | M H | C | C | .... E | ...... G | V | .... V | ........ | V |
| Mc1(3) | ..G | M H | C | C | .... E | ...... Y | V | .... V | ........ | V |
| pWD217_278 | ..G | M T | C | C | .... E | ...... G | V | .... V | ........ | V |
| Mc1(4) | ..G | M T | C | C | .... E | ...... G | V | .... V | ........ | V |
| pWD346_405 | ..G | M T | C | C | .... E | ...... G | V | .... V | ........ | I |
| Mc1(5) | ..G | M T | C | C | .... E | ...... G | I | .... V | ........ | V |
| pWD422_481 | ..G | M T | C | C | .... E | ...... G | I | .... V | ........ | V |
| Mc1(6) | ..G | M T | C | C | .... E | ...... G | I | .... V | ........ | I |
| CopA | ..G | M T | C | C | .... E | ...... G | V | .... V | ........ | V |
| Cd ATPase | ..G | F S | C | C | .... E | ...... G | V | .... V | ........ | V |
| Cd ATPase | ..G | F S | C | C | .... E | ...... G | V | .... V | ........ | V |
| Hg++ reductase | ..G | M T | C | C | .... K | ...... G | V | .... V | ........ | L |
| hyp protein 3 | ..G | M T | C | C | .... E | ...... G | V | .... V | ........ | V |
| NR1 Hg++ resistance | ..G | M T | C | C | .... K | ...... G | V | .... V | ........ | V |
| Hg++ transport | ..G | M T | C | C | .... K | ...... G | V | .... V | ........ | V |
| Hg++ resistance | ..G | M T | C | C | .... K | ...... G | V | .... V | ........ | L |

FIG. 9

| | |
|---|---|
| pWD | CPC...P.......DKTG.......SEHPLGVA |
| Mc1 (Menkes) | CPC...P.......DKTG.......SEHPLGTA |
| CopA | CPC...P.......DKTG.......SEHPLGKA |
| fixI | CPC...P.......DKTG.......SRHPIAVA |
| CadA | CPC...P.......DKTG.......SQHPLASA |

FIG. 10

```
  1 TTCCCGGACCCCTGTTTGCTTTAGAGCCGAGCCGCCGCCGCCGATGCCCTCACACTCTG
 61 CGCCTCCTCCTCCCGGGACTTTAACACACCACGCTCTCCTCCACCGACCAGGTGACCTTTGC

121 TCTGAGCCAGATCAGAGAAGAATTCGTGTCCGTGCGGGACGATGCCTGAGCAGGAGAGA
                                              MetProGluGlnGluArg
                                          exon 1 exon 2
181 CAGATCACAGCCAGAGAAGGGGCCAGTCGGAAA ATCTTATCTAAGCTTTCTTTGCCTACC
    GlnIleThrAlaArgGlyGluGlyAlaSerArgLys  IleLeuSerLysLeuSerLeuProThr 241 CGTGCCTGGGAACCAGCAGCAATGAAGAAGAGTTTTGCTTTTGACAATGTTGGCTATGAAGGT
    ArgAlaTrpGluProAlaMetLysLysSerPheAlaPheAspAsnValGlyTyrGluGly 301 GGTCTCGGATGGCCTGGGCCCCTTCTTCTCAGTGGCCACCAGCACAGTCAGGATCTTGGGC
    GlyLeuAspGlyLeuGlyProSerSerGlnValAlaThrSerThrValArgIleLeuGly 361 ATGACTTGCCAGTCCATGTGTGAAGTTCCATTGAGGACAGGATTTCCAATTTGAAAGGCATC
    MetThrCysGlnSerCysValLysSerIleGluAspArgIleSerAsnLeuLysGlyIle 421 ATCAGCATGAAGGTTTCCCTGGAACAAGACAGTGCCACTGTGAAATATGTGCCATCGGTT
    IleSerMetLysValSerLeuGluGlnAspSerAlaThrValLysTyrValProSerVal 481 GTGTGCCTGCAACAGGTTTGCCATCAAATTGGGACATGGGCTTCGAGGCCAGCATTGCA
    ValCysLeuGlnValCysHisGlnIleGlyAspMetGlyPheGluAlaSerIleAla 541 GAAGGAAAGGCAGCCTCCTGCCCTCAAGGTCCCTTGCCTGCCCAGGAGGCTGTGGTCAAG
    GluGlyLysAlaAlaSerTrpProSerArgSerLeuProAlaGlnGluAlaValValLys 601 CTCCGGGTG
    LeuArgVal
```

Exon composition:
l1, b1: ex5-ex6-ex7-ex8-ex9
b2:    ex5-ex6-ex7-ex9
l2:    ex5-ex8-ex9
b3:    ex5-ex9

Exon composition:
l1, b1: ex11-ex12-ex13
b2: ex11-ex13

Exon composition:
l1, b1: ex11-ex12-ex13-ex14
b2: ex11-ex12-ex14
b4: ex11-ex14

FIG. 15A

```
WD-3       HVVTLQLRID  ......  ......  ENIGQLI  PQSIQ....  ......  KT.QVKY.PS  CTSPVALQRA  IEALPPGNFK  VS
WD-5       APQKCFLQIK  ......  ......  RNLQKEA  VLSVL....  ......  GK.EIKT.L.  VIQPLEIAQF  IQDLGFEAAV  ME
WD-6       SDGNIELTTT  ......  ......  SKLTRTN  FTYAS....  ......  SK.LVKF.D.  IIGPRDIIKI  IEEIGFHASL  AQ
WD-2       QEAVVKLRVE  ......  ......  GKVRKLQ  VRVK.....  ......  QE.VTTQ.Y.  LIQPEDLRDH  VNDMGFEAAI  KS
WD-4       TCSTTLIAIA  ......  ......  GMISQLE  VQQIS....  ......  GT.VLYN.S.  VISPEELRAA  IEDMGFEASV  VS
WD-1       QVATSTVRIL  ......  ......  DRISNLK  RISMR....  ......  DS.TVKY.VS  VVCLQQVCHQ  IGDMGFEASI  AE
Consensus  ......L.I.  ......  ......  .........  .........  ......  ...VK.....  ....I.P...  ..I.D.GFEA  ..
```

FIG. 15B

```
WD-1       Q..QSTVRIL  ......  ......  F.SNLK...  .SMKVSL.D  ......  DS..VKY.PS  VVCLQQVCHQ  IGDMGFEASI  AE
WD-3       HV..LQIR.D  ......  ......  ENIGQLI..  PQSIQVSLAN  ......  KT.QVKY.PS  CTSPVALQRA  IEALPPGNFK  VS
Consensus  ...........  ......  ......  ..........  ..VSL.D  ......  .......PS  ...........  ..I........  ..
```

FIG. 15C

```
              QEAVVKLRVE  ......... ......... .VRK... .VRKYNSLSN  QEAVVITQTV  IEDPEILRDH  VNDMGFEAAI  KS
              TCSTTLIAIA  ......... ......... .IEC... SQISQVSLRE  GTATVLMNES  VEEPELLRAA  IEDMGFEASV  VS
```

WD-2
WD-4
Consensus

FIG. 15D

```
MerA-N1       EVKKYRMNVQ  GMTCGCEQCH  .AVALENVGA  KIEVDFRRG  EAFELPDDV  KVEDAKVAIA  DANY.PGEAE  EF
MerA-N2       EVKKYRINVE  GMTCGCEBCH  .AVALENVGA  KCIEVDFRRG  EAFELPMDV  DIDIAKQAIT  DAQYC.PGEAE  EI
Consensus     EVKKYR..NV.  GMTC.GCE.H  .AVALEN.GA  K..IEVDFRRG  EA.FELP.DV  ..AK.AI.  DA.Y.PGEAE  E.
```

MerA-N1
MerA-N2
Consensus

SEQUENCE LISTING (1) GENERAL INFORMATION:

(iii) NUMBER OF SEQUENCES: 107

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (xi) SEQUENCE DESCRIPTION: SEQ ID NO:1:

GGATTACAGG YRTGAGCCA                                               19

(2) INFORMATION FOR SEQ ID NO:2:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (xi) SEQUENCE DESCRIPTION: SEQ ID NO:2:

RCCAYTGCAC TCCAGCCTG                                               19

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (xi) SEQUENCE DESCRIPTION: SEQ ID NO:3:

CCCAGTGAGC AGCCTCTAAA                                          20

(2) INFORMATION FOR SEQ ID NO:4:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:4:

AACAGAAATC AGGCCAGTGT G                                                    21

(2) INFORMATION FOR SEQ ID NO:5:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:5:

CTGCCACCTA TTTTTGTAAA TAAAG                                                25

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:6:

TGATCTGGTG GTTCAACTGG                                                      20

(2) INFORMATION FOR SEQ ID NO:7:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:7:

ATCATACCTG GTTGTGCAAC C                                                    21

(2) INFORMATION FOR SEQ ID NO:8:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:8:

CCAGATGCTT CTTTCTAAAC ACACA                                                    25

(2) INFORMATION FOR SEQ ID NO:9:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:9:

CAAACTTTTA GTATGAGTCT ATCTCTCTCT                                               30

(2) INFORMATION FOR SEQ ID NO:10:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:10:

TCATTAAAGT GAGGAGTGAG GTAAATG                                                  27

(2) INFORMATION FOR SEQ ID NO:11:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:11:

TTATGATGAA AAAGTAATA TAAGAGGTCC C                                              31

(2) INFORMATION FOR SEQ ID NO:12:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:12:

AGCTGTATCT GGGGTTGG                                                            18

(2) INFORMATION FOR SEQ ID NO:13:

(i) SEQUENCE CHARACTERISTICS:
            (A) LENGTH: 31 base pairs
            (B) TYPE: nucleic acid
            (C) STRANDEDNESS: single (D) TOPOLOGY: linear (ii) MOLECULE TYPE: DNA (genomic)

(iii) HYPOTHETICAL: NO (xi) SEQUENCE DESCRIPTION: SEQ ID NO:13:

AGTTTCTACA TGAATAAAAT CGTACTAGAA G                                           31

(2) INFORMATION FOR SEQ ID NO:14:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:14:

GGTATCTTGT ATAATACTAC CTTCCATCA                                              29

(2) INFORMATION FOR SEQ ID NO:15:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:15:

TTTAACTGGC ATGTTAATCT GGG                                                    23

(2) INFORMATION FOR SEQ ID NO:16:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:16:

CTCCCCCTCC TTGCCTGCAA CT                                                     22

(2) INFORMATION FOR SEQ ID NO:17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:17:

CCTGGAACTG GAAGATGGCA                                                        20

```
(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:18:

GGAGTTGGGG AGACCACAAT                                               20

(2) INFORMATION FOR SEQ ID NO:19:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:19:

AATAAA                                                               6

(2) INFORMATION FOR SEQ ID NO:20:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:20:

Gly Xaa Xaa Cys Xaa Xaa Cys
            5

(2) INFORMATION FOR SEQ ID NO:21:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:21:

Gly Asp Gly Xaa Asn Asp Xaa Pro Leu
1               5

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:22:

CAGCTACCAG AGAAGGACAT GG                                            22
```

(2) INFORMATION FOR SEQ ID NO:23:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:23:

Ser Glu His Pro Leu Gly Val Ala
1               5

(2) INFORMATION FOR SEQ ID NO:24:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:24:

Ser Glu His Pro Leu Gly Thr Ala
1               5

(2) INFORMATION FOR SEQ ID NO:25:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:25:

Ser Glu His Pro Leu Gly Lys Ala
1               5

(2) INFORMATION FOR SEQ ID NO:26:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:26:

Ser Arg His Pro Ile Ala Val Ala
1               5

(2) INFORMATION FOR SEQ ID NO:27:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:27:

Ser Gln His Pro Leu Ala Ser Ala
1               5

(2) INFORMATION FOR SEQ ID NO:28:

(i) SEQUENCE CHARACTERISTICS:
    (A) LENGTH: 5421 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (vi) ORIGINAL SOURCE:
    (A) ORGANISM: Homo Sapiens (ix) FEATURE:
    (A) NAME/KEY: CDS
    (B) LOCATION: 1..3330

(xi) SEQUENCE DESCRIPTION: SEQ ID NO:28:

```
GTG GAG GGC ATG ACC TGC CAG TCC TGT GTC AGC TCC ATT GAA GGC AAG      48
Val Glu Gly Met Thr Cys Gln Ser Cys Val Ser Ser Ile Glu Gly Lys
 1               5                  10                  15

GTC CGG AAA CTG CAA GGA GTA GTG AGA GTC AAA GTC TCA CTC AGC AAC      96
Val Arg Lys Leu Gln Gly Val Val Arg Val Lys Val Ser Leu Ser Asn
             20                  25                  30

CAA GAG GCC GTC ATC ACT TAT CAG CCT TAT CTC ATT CAG CCC GAA GAC     144
Gln Glu Ala Val Ile Thr Tyr Gln Pro Tyr Leu Ile Gln Pro Glu Asp
         35                  40                  45

CTC AGG GAC CAT GTA AAT GAC ATG GGA TTT GAA GCT GCC ATC AAG AGC     192
Leu Arg Asp His Val Asn Asp Met Gly Phe Glu Ala Ala Ile Lys Ser
     50                  55                  60

AAA GTG GCT CCC TTA AGC CTG GGA CCA ATT GAT ATT GAG CGG TTA CAA     240
Lys Val Ala Pro Leu Ser Leu Gly Pro Ile Asp Ile Glu Arg Leu Gln
 65                  70                  75                  80

AGC ACT AAC CCA AAG AGA CCT TTA TCT TCT GCT AAC CAG AAT TTT AAT     288
Ser Thr Asn Pro Lys Arg Pro Leu Ser Ser Ala Asn Gln Asn Phe Asn
                 85                  90                  95

AAT TCT GAG ACC TTG GGG CAC CAA GGA AGC CAT GTG GTC ACC CTC CAA     336
Asn Ser Glu Thr Leu Gly His Gln Gly Ser His Val Val Thr Leu Gln
            100                 105                 110

CTG AGA ATA GAT GGA ATG CAT TGT AAG TCT TGC GTC TTG AAT ATT GAA     384
Leu Arg Ile Asp Gly Met His Cys Lys Ser Cys Val Leu Asn Ile Glu
        115                 120                 125

GAA AAT ATT GGC CAG CTC CTA GGG GTT CAA AGT ATT CAA GTG TCC TTG     432
Glu Asn Ile Gly Gln Leu Leu Gly Val Gln Ser Ile Gln Val Ser Leu
    130                 135                 140

GAG AAC AAA ACT GCC CAA GTA AAG TAT GAC CCT TCT TGT ACC AGC CCA     480
Glu Asn Lys Thr Ala Gln Val Lys Tyr Asp Pro Ser Cys Thr Ser Pro
145                 150                 155                 160

GTG GCT CTG CAG AGG GCT ATC GAG GCA CTT CCA CCT GGG AAT TTT AAA     528
Val Ala Leu Gln Arg Ala Ile Glu Ala Leu Pro Pro Gly Asn Phe Lys
                165                 170                 175

GTT TCT CTT CCT GAT GGA GCC GAA GGG AGT GGG ACA GAT CAC AGG TCT     576
Val Ser Leu Pro Asp Gly Ala Glu Gly Ser Gly Thr Asp His Arg Ser
            180                 185                 190

TCC AGT TCT CAT TCC CCT GGC TCC CCA CCG AGA AAC CAG GTC CAG GGC     624
Ser Ser Ser His Ser Pro Gly Ser Pro Pro Arg Asn Gln Val Gln Gly
        195                 200                 205

ACA TGC AGT ACC ACT CTG ATT GCC ATT GCC GGC ATG ACC TGT GCA TCC     672
Thr Cys Ser Thr Thr Leu Ile Ala Ile Ala Gly Met Thr Cys Ala Ser
    210                 215                 220

TGT GTC CAT TCC ATT GAA GGC ATG ATC TCC CAA CTG GAA GGG GTG CAG     720
Cys Val His Ser Ile Glu Gly Met Ile Ser Gln Leu Glu Gly Val Gln
225                 230                 235                 240
```

```
CAA ATA TCG GTG TCT TTG GCC GAA GGG ACT GCA ACA GTT CTT TAT AAT         768
Gln Ile Ser Val Ser Leu Ala Glu Gly Thr Ala Thr Val Leu Tyr Asn
            245                 250                 255

CCC TCT GTA ATT AGC CCA GAA GAA CTC AGA GCT GCT ATA GAA GAC ATG         816
Pro Ser Val Ile Ser Pro Glu Glu Leu Arg Ala Ala Ile Glu Asp Met
            260                 265                 270

GGA TTT GAG GCT TCA GTC GTT TCT GAA AGC TGT TCT ACT AAC CCT CTT         864
Gly Phe Glu Ala Ser Val Val Ser Glu Ser Cys Ser Thr Asn Pro Leu
            275                 280                 285

GGA AAC CAC AGT GCT GGG AAT TCC ATG GTG CAA ACT ACA GAT GGT ACA         912
Gly Asn His Ser Ala Gly Asn Ser Met Val Gln Thr Thr Asp Gly Thr
            290                 295                 300

CCT ACA TCT GTG CAG GAA GTG GCT CCC CAC ACT GGG AGG CTC CCT GCA         960
Pro Thr Ser Val Gln Glu Val Ala Pro His Thr Gly Arg Leu Pro Ala
305                 310                 315                 320

AAC CAT GCC CCG GAC ATC TTG GCA AAG TCC CCA CAA TCA ACC AGA GCA        1008
Asn His Ala Pro Asp Ile Leu Ala Lys Ser Pro Gln Ser Thr Arg Ala
            325                 330                 335

GTG GCA CCG CAG AAG TGC TTC TTA CAG ATC AAA GGC ATG ACC TGT GCA        1056
Val Ala Pro Gln Lys Cys Phe Leu Gln Ile Lys Gly Met Thr Cys Ala
            340                 345                 350

TCC TGT GTG TCT AAC ATA GAA AGG AAT CTG CAG AAA GAA GCT GGT GTT        1104
Ser Cys Val Ser Asn Ile Glu Arg Asn Leu Gln Lys Glu Ala Gly Val
            355                 360                 365

CTC TCC GTG TTG GTT GCC TTG ATG GCA GGA AAG GCA GAG ATC AAG TAT        1152
Leu Ser Val Leu Val Ala Leu Met Ala Gly Lys Ala Glu Ile Lys Tyr
            370                 375                 380

GAC CCA GAG GTC ATC CAG CCC CTC GAG ATA GCT CAG TTC ATC CAG GAC        1200
Asp Pro Glu Val Ile Gln Pro Leu Glu Ile Ala Gln Phe Ile Gln Asp
385                 390                 395                 400

CTG GGT TTT GAG GCA GCA GTC ATG GAG GAC TAC GCA GGC TCC GAT GGC        1248
Leu Gly Phe Glu Ala Ala Val Met Glu Asp Tyr Ala Gly Ser Asp Gly
            405                 410                 415

AAC ATT GAG CTG ACA ATC ACA GGG ATG ACC TGC GCG TCC TGT GTC CAC        1296
Asn Ile Glu Leu Thr Ile Thr Gly Met Thr Cys Ala Ser Cys Val His
            420                 425                 430

AAC ATA GAG TCC AAA CTC ACG AGG ACA AAT GGC ATC ACT TAT GCC TCC        1344
Asn Ile Glu Ser Lys Leu Thr Arg Thr Asn Gly Ile Thr Tyr Ala Ser
            435                 440                 445

GTT GCC CTT GCC ACC AGC AAA GCC CTT GTT AAG TTT GAC CCG GAA ATT        1392
Val Ala Leu Ala Thr Ser Lys Ala Leu Val Lys Phe Asp Pro Glu Ile
450                 455                 460

ATC GGT CCA CGG GAT ATT ATC AAA ATT ATT GAG AGC AAA ACC TCA GAA        1440
Ile Gly Pro Arg Asp Ile Ile Lys Ile Ile Glu Ser Lys Thr Ser Glu
465                 470                 475                 480

GCC CTG GCT AAA CTC ATG TCT CTC CAA GCC ACA GAA GCC ACC GTT GTG        1488
Ala Leu Ala Lys Leu Met Ser Leu Gln Ala Thr Glu Ala Thr Val Val
            485                 490                 495

ACC CTT GGT GAG GAC AAT TTA ATC ATC AGG GAG GAG CAA GTC CCC ATG        1536
Thr Leu Gly Glu Asp Asn Leu Ile Ile Arg Glu Glu Gln Val Pro Met
            500                 505                 510

GAG CTG GTG CAG CGG GGC GAT ATC GTC AAG GTG GTC CCT GGG GGA AAG        1584
Glu Leu Val Gln Arg Gly Asp Ile Val Lys Val Val Pro Gly Gly Lys
            515                 520                 525

TTT CCA GTG GAT GGG AAA GTC CTG GAA GGC AAT ACC ATG GCT GAT GAG        1632
Phe Pro Val Asp Gly Lys Val Leu Glu Gly Asn Thr Met Ala Asp Glu
            530                 535                 540

TCC CTC ATC ACA GGA GAA GCC ATG CCA GTC ACT AAG AAA CCC GGA AGC        1680
Ser Leu Ile Thr Gly Glu Ala Met Pro Val Thr Lys Lys Pro Gly Ser
545                 550                 555                 560
```

-continued

```
ACT GTA ATT GCG AGG TCT ATA AAT GCA CAT GGC TCT GTG CTC ATT AAA    1728
Thr Val Ile Ala Arg Ser Ile Asn Ala His Gly Ser Val Leu Ile Lys
            565                 570                 575

GCT ACC CAC GTG GGC AAT GAC ACC ACT TTG GCT CAG ATT GTG AAA CTG    1776
Ala Thr His Val Gly Asn Asp Thr Thr Leu Ala Gln Ile Val Lys Leu
                580                 585                 590

GTG GAA GAG GCT CAG ATG TCA AAG AAC CCC AAC AAG CAC ATC TCC CAG    1824
Val Glu Glu Ala Gln Met Ser Lys Asn Pro Asn Lys His Ile Ser Gln
            595                 600                 605

ACA GAG GTG ATC ATC CGG TTT GCT TTC CAG ACG TCC ATC ACG GTG CTG    1872
Thr Glu Val Ile Ile Arg Phe Ala Phe Gln Thr Ser Ile Thr Val Leu
            610                 615                 620

TGC ATT GCC TGC CCC TGC TCC CTG GGG CTG GCC ACG CCC ACG GCT GTC    1920
Cys Ile Ala Cys Pro Cys Ser Leu Gly Leu Ala Thr Pro Thr Ala Val
625                 630                 635                 640

ATG GTG GGC ACC GGG GTG GCC GCG CAG AAC GGC ATC CTC ATC AAG GGA    1968
Met Val Gly Thr Gly Val Ala Ala Gln Asn Gly Ile Leu Ile Lys Gly
            645                 650                 655

GGC AAG CCC CTG GAG ATG GCG CAC AAG ATA AAG ACT GTG ATG TTT GAC    2016
Gly Lys Pro Leu Glu Met Ala His Lys Ile Lys Thr Val Met Phe Asp
            660                 665                 670

AAG ACT GGC ACC ATT ACC CAT GGC GTC CCC AGG GTC ATG CGG GTG CTC    2064
Lys Thr Gly Thr Ile Thr His Gly Val Pro Arg Val Met Arg Val Leu
            675                 680                 685

CTG CTG GGG GAT GTG GCC ACA CTG CCC CTC AGG AAG GTT CTG GCT GTG    2112
Leu Leu Gly Asp Val Ala Thr Leu Pro Leu Arg Lys Val Leu Ala Val
            690                 695                 700

GTG GGG ACT GCG GAG GCC AGC AGT GAA CAC CCC TTG GGC GTG GCA GTC    2160
Val Gly Thr Ala Glu Ala Ser Ser Glu His Pro Leu Gly Val Ala Val
705                 710                 715                 720

ACC AAA TAC TGT AAA GAG GAA CTT GGA ACA GAG ACC TTG GGA TAC TGC    2208
Thr Lys Tyr Cys Lys Glu Glu Leu Gly Thr Glu Thr Leu Gly Tyr Cys
            725                 730                 735

ACG GAC TTC CAG GCA GTG CCA GGC TGT GGA ATT GGG TGC AAA GTC AGC    2256
Thr Asp Phe Gln Ala Val Pro Gly Cys Gly Ile Gly Cys Lys Val Ser
            740                 745                 750

AAC GTG GAA GGC ATC CTG GCC CAC AGT GAG CGC CCT TTG AGT GCA CCG    2304
Asn Val Glu Gly Ile Leu Ala His Ser Glu Arg Pro Leu Ser Ala Pro
            755                 760                 765

GCC AGT CAC CTG AAT GAG GCT GGC AGC CTT CCC GCA GAA AAA GAT GCA    2352
Ala Ser His Leu Asn Glu Ala Gly Ser Leu Pro Ala Glu Lys Asp Ala
770                 775                 780

GTC CCC CAG ACC TTC TCT GTG CTG ATT GGA AAC CGT GAG TGG CTG AGG    2400
Val Pro Gln Thr Phe Ser Val Leu Ile Gly Asn Arg Glu Trp Leu Arg
785                 790                 795                 800

CGC AAC GGT TTA ACC ATT TCT AGC GAT GTC AGC GAC GCT ATG ACA GAC    2448
Arg Asn Gly Leu Thr Ile Ser Ser Asp Val Ser Asp Ala Met Thr Asp
            805                 810                 815

CAC GAG ATG AAA GGA CAG ACA GCC ATC CTG GTG GCT ATT GAC GGT GTG    2496
His Glu Met Lys Gly Gln Thr Ala Ile Leu Val Ala Ile Asp Gly Val
            820                 825                 830

CTC TGT GGG ATG ATC GCA ATC GCA GAC GCT GTC AAG CAG GAG GCT GCC    2544
Leu Cys Gly Met Ile Ala Ile Ala Asp Ala Val Lys Gln Glu Ala Ala
            835                 840                 845

CTG GCT GTG CAC ACG CTG CAG AGC ATG GGT GTG GAC GTG GTT CTG ATC    2592
Leu Ala Val His Thr Leu Gln Ser Met Gly Val Asp Val Val Leu Ile
            850                 855                 860

ACG GGG GAC AAC CGG AAG ACA GCC AGA GCT ATT GCC ACC CAG GTT GGC    2640
Thr Gly Asp Asn Arg Lys Thr Ala Arg Ala Ile Ala Thr Gln Val Gly
```

-continued

| | | | | | | | | | | | | | | | | |
|---|---|---|---|---|---|---|---|---|---|---|---|---|---|---|---|---|
| 865 | | | | | 870 | | | | | 875 | | | | | 880 | |
| ATC | AAC | AAA | GTC | TTT | GCA | GAG | GTG | CTG | CCT | TCG | CAC | AAG | GTG | GCC | AAG | 2688 |
| Ile | Asn | Lys | Val | Phe | Ala | Glu | Val | Leu | Pro | Ser | His | Lys | Val | Ala | Lys | |
| | | | | 885 | | | | | 890 | | | | | 895 | | |
| GTC | CAG | GAG | CTC | CAG | AAT | AAA | GGG | AAG | AAA | GTC | GCC | ATG | GTG | GGG | GAT | 2736 |
| Val | Gln | Glu | Leu | Gln | Asn | Lys | Gly | Lys | Lys | Val | Ala | Met | Val | Gly | Asp | |
| | | | 900 | | | | | 905 | | | | | 910 | | | |
| GGG | GTC | AAT | GAC | TCC | CCG | GCC | TTG | GCC | CAG | GCA | GAC | ATG | GGT | GTG | GCC | 2784 |
| Gly | Val | Asn | Asp | Ser | Pro | Ala | Leu | Ala | Gln | Ala | Asp | Met | Gly | Val | Ala | |
| | | | 915 | | | | | 920 | | | | | 925 | | | |
| ATT | GGC | ACC | GGC | ACG | GAT | GTG | GCC | ATC | GAG | GCA | GCC | GAC | GTC | GTC | CTT | 2832 |
| Ile | Gly | Thr | Gly | Thr | Asp | Val | Ala | Ile | Glu | Ala | Ala | Asp | Val | Val | Leu | |
| | | | 930 | | | | | 935 | | | | | 940 | | | |
| ATC | AGA | AAT | GAT | TTG | CTG | GAT | GTG | GTG | GCT | AGC | ATT | CAC | CTT | TCC | AAG | 2880 |
| Ile | Arg | Asn | Asp | Leu | Leu | Asp | Val | Val | Ala | Ser | Ile | His | Leu | Ser | Lys | |
| 945 | | | | | 950 | | | | | 955 | | | | | 960 | |
| AGG | ACT | GTC | CGA | AGG | ATA | CGC | ATC | AAC | CTG | GTC | CTG | GCA | CTG | ATT | TAT | 2928 |
| Arg | Thr | Val | Arg | Arg | Ile | Arg | Ile | Asn | Leu | Val | Leu | Ala | Leu | Ile | Tyr | |
| | | | | 965 | | | | | 970 | | | | | 975 | | |
| AAC | CTG | GTT | GGG | ATA | CCC | ATT | GCA | GCA | GGT | GTC | TTC | ATG | CCC | ATC | GGC | 2976 |
| Asn | Leu | Val | Gly | Ile | Pro | Ile | Ala | Ala | Gly | Val | Phe | Met | Pro | Ile | Gly | |
| | | | 980 | | | | | 985 | | | | | 990 | | | |
| ATT | GTG | CTG | CAG | CCC | TGG | ATG | GGC | TCA | GCG | GCC | ATG | GCA | GCC | TCC | TCT | 3024 |
| Ile | Val | Leu | Gln | Pro | Trp | Met | Gly | Ser | Ala | Ala | Met | Ala | Ala | Ser | Ser | |
| | | | 995 | | | | | 1000 | | | | | 1005 | | | |
| GTG | TCT | GTG | GTG | CTC | TCA | TCC | CTG | CAG | CTC | AAG | TGC | TAT | AAG | AAG | CCT | 3072 |
| Val | Ser | Val | Val | Leu | Ser | Ser | Leu | Gln | Leu | Lys | Cys | Tyr | Lys | Lys | Pro | |
| | | | 1010 | | | | | 1015 | | | | | 1020 | | | |
| GAC | CTG | GAG | AGG | TAT | GAG | GCA | CAG | GCG | CAT | GGC | CAC | ATG | AAG | CCC | CTG | 3120 |
| Asp | Leu | Glu | Arg | Tyr | Glu | Ala | Gln | Ala | His | Gly | His | Met | Lys | Pro | Leu | |
| 1025 | | | | | 1030 | | | | | 1035 | | | | | 1040 | |
| ACG | GCA | TCC | CAG | GTC | AGT | GTG | CAC | ATA | GGC | ATG | GAT | GAC | AGG | TGG | CGG | 3168 |
| Thr | Ala | Ser | Gln | Val | Ser | Val | His | Ile | Gly | Met | Asp | Asp | Arg | Trp | Arg | |
| | | | | 1045 | | | | | 1050 | | | | | 1055 | | |
| GAC | TCC | CCC | AGG | GCC | ACA | CCA | TGG | GAC | CAG | GTC | AGC | TAT | GTC | AGC | CAG | 3216 |
| Asp | Ser | Pro | Arg | Ala | Thr | Pro | Trp | Asp | Gln | Val | Ser | Tyr | Val | Ser | Gln | |
| | | | 1060 | | | | | 1065 | | | | | 1070 | | | |
| GTG | TCG | CTG | TCC | TCC | CTG | ACG | TCC | GAC | AAG | CCA | TCT | CGG | CAC | AGC | GCT | 3264 |
| Val | Ser | Leu | Ser | Ser | Leu | Thr | Ser | Asp | Lys | Pro | Ser | Arg | His | Ser | Ala | |
| | | | 1075 | | | | | 1080 | | | | | 1085 | | | |
| GCA | GCA | GAC | GAT | GAT | GGG | GAC | AAG | TGG | TCT | CTG | CTC | CTG | AAT | GGC | AGG | 3312 |
| Ala | Ala | Asp | Asp | Asp | Gly | Asp | Lys | Trp | Ser | Leu | Leu | Leu | Asn | Gly | Arg | |
| | | | 1090 | | | | | 1095 | | | | | 1100 | | | |
| GAT | GAG | GAG | CAG | TAC | ATC | TGATGACTTC | AGGCAGGCGG | GCCGGGCAG | | | | | | | | 3360 |
| Asp | Glu | Glu | Gln | Tyr | Ile | | | | | | | | | | | |
| 1105 | | | | | 1110 | | | | | | | | | | | |

| | |
|---|---|
| GGACTTGCCT CCACTCACCA CAAGCTGAGC AGGACAGCCA GCAGCAGGAT GGGCTGAGCT | 3420 |
| AGCCTCCAGC TTTGGGGACT TCCGCTCCCT GGATATGTCC AGTCATCCTG CCCTGCAGCA | 3480 |
| CGCGGCCTTG TCTGGGTGCA GCTGGGCTTG GCCTGGAGAG GACGGCCCTG CCTGCCTCTT | 3540 |
| GGCCTCACGG GACCGTCAGC ATGGGCTTTG TCTTGGACTC TAGTCCTTGG CTGGACTGTA | 3600 |
| GAAGGTGAGA GGCGAGTCAC CCTCCTCACA GACCTCTGCT GGAGTATTT AGGATGACTG | 3660 |
| CTGTGAAATG GAGAACAGTT TCATCAGGAC CAAAAAACCT CACTGGGCCT TTCCAGAGAA | 3720 |
| CTGCAGACCT CACTGTCAGG GTCTTTCTGA TGACGCCTGT CTGTGTGCAT CATGTTTCTG | 3780 |
| AGACCACAGT TTACCTCAGG TGTGCCTGTT GCTTTCTTCC TGCATAGTCT GTTCCTTTCT | 3840 |
| TCGTACATAG TCTGTTCCTT TTCTCTCCTG TGTGCTTGTC AGTGGGGACC CCTCGCAACC | 3900 |

```
CTGCCTGTCA CCTGGGAGGG TGGGACCAAT GTCCTTGTGG TCTTTGCTGC TGCTCTCAGG    3960

CGCTTCTCCA ATGCTCTGGA GTGTGCATTT CAGCTTGAAC CTGCTTCCTG GCTCACACAT    4020

CCCCAGCCAG GGAGCTTGCC ACACTCTTCT TCAAGTTGAG GAGAGTTCTT TTTTGCTTAA    4080

AGCCCCCTTC TCCATGGAGT GTTGGCTTCT CAATAGAGTG TTGTTGCTGA CCAGCTGGAG    4140

TGAGGGCCTC AGAGCCTGAC CTGAGAGTCC GTACTCGGCT TCCTGTGGGG TGTAGGTTCT    4200

CGCGATTCAG GACGTCCTTC CATATCCCTG CCCAGCCTGT GGTGCTTGAA ACGTTTGCCC    4260

CATGGGAAAC GTATGTGTGC AGGAGCCTCC CTGCACGGCC CAAGGGGCTT CGTTTTCAGT    4320

CTTCTGACTG TCACCTCGTG GGGTTCAGTA GAGAATTCAA TTACTAGCGC CTGGCCTTGT    4380

GTGGCTTGGA GGAAATGGTA CTGCCCAAAT AGGAGGAAAA CACAGCCTCC CTGAGCCTGC    4440

ATTCTGCACG CTGCCCAGGG GCTTCAGAAA AGGAGTGGCC ACAGCACCCC GAAGGGAGCA    4500

TCTATTTACC TGGCAGTGGC TCTCAGAGCA GCAGAACGGG TTCAGTTTTA GACTCTGAAG    4560

TTGGTTGTGA TTGACAGAAC CCTTTGGGAG CAAACTAGTA GAGTTGGATT AAATTCTGGG    4620

TGAAACCCTT TTCTCCCACA CAAAATAGTT TTAGTGATTT TTTTCATTGT CCATTACTTG    4680

CCAGGGGCAG TTTTAGCAGC ACTTTTGATA GATTACGTCT AATCCTCCCA ACCAACCAGC    4740

AGGGTAGCTA TTACTGTCCA CATTTTACAG GCAAGGAAAC AGGCTCCAAG AGGCTGAGGA    4800

CTTTGCCCAG GATGACATAG CCAATGGACA AGCAGTGTCT GTCAGCTGTG AAGGCTTCAC    4860

TCTTATTGTC CTTCTACCTT GAATAGAAGT TTTCCTGATA AGAATAAACG AGGAAAAGGT    4920

CCTTGCCTCC TGGAAGAACA AATCTACCAG GTGATCTATT CATTGTTTCA ACTCAGAATG    4980

CACTTGATTC AGGAGGTCAT CTGACCTTCA CCTTGGATGG TTAGTTTCAC TTTTTACATA    5040

TAGTTTTTGC AGGGTTTTAT TTTATAAAAT CCAAGCGCGC TGTTGATTGT GTTTTCCTTG    5100

TTTTCAGCCC CCCGACTCCA GCCCGCAGCA CATTTCCGCT GTCCGTCAGT AATTGTGTCC    5160

TCTCTTTATG CTTGCTTGGG GAATGTTGTT TTCTGACTAG GCTGATCATT ATCTAAAGAA    5220

TCTAATTCTG TTGATTTTTA AAACTTTTAG GACCATAAAC GTTGTGTTCA TATATGGACA    5280

TGGAAATATT TATATAATTT TATAGAAAAT AACCTTTTAG ATGGTCAAAG TGTAAGGAGT    5340

TTTTTTGTCA GATAATCATT TCTACTTCAA AAACATTTCA TGCAATATTA GAATAAAGTT    5400

CCTGTCATTC CTCTAAAAAA A                                             5421
```

(2) INFORMATION FOR SEQ ID NO:29:

(i) SEQUENCE CHARACTERISTICS:
        (A) LENGTH: 1110 amino acids
        (B) TYPE: amino acid
        (D) TOPOLOGY: linear (ii) MOLECULE TYPE: protein (xi) SEQUENCE DESCRIPTION: SEQ ID NO:29:

```
Val Glu Gly Met Thr Cys Gln Ser Cys Val Ser Ser Ile Glu Gly Lys
 1               5                  10                  15

Val Arg Lys Leu Gln Gly Val Val Arg Val Lys Val Ser Leu Ser Asn
            20                  25                  30

Gln Glu Ala Val Ile Thr Tyr Gln Pro Tyr Leu Ile Gln Pro Glu Asp
        35                  40                  45

Leu Arg Asp His Val Asn Asp Met Gly Phe Glu Ala Ala Ile Lys Ser
    50                  55                  60

Lys Val Ala Pro Leu Ser Leu Gly Pro Ile Asp Ile Glu Arg Leu Gln
65                  70                  75                  80
```

```
Ser Thr Asn Pro Lys Arg Pro Leu Ser Ser Ala Asn Gln Asn Phe Asn
                85                  90                  95

Asn Ser Glu Thr Leu Gly His Gln Gly Ser His Val Val Thr Leu Gln
            100                 105                 110

Leu Arg Ile Asp Gly Met His Cys Lys Ser Cys Val Leu Asn Ile Glu
        115                 120                 125

Glu Asn Ile Gly Gln Leu Leu Gly Val Gln Ser Ile Gln Val Ser Leu
    130                 135                 140

Glu Asn Lys Thr Ala Gln Val Lys Tyr Asp Pro Ser Cys Thr Ser Pro
145                 150                 155                 160

Val Ala Leu Gln Arg Ala Ile Glu Ala Leu Pro Pro Gly Asn Phe Lys
                165                 170                 175

Val Ser Leu Pro Asp Gly Ala Glu Gly Ser Gly Thr Asp His Arg Ser
            180                 185                 190

Ser Ser His Ser Pro Gly Ser Pro Pro Arg Asn Gln Val Gln Gly
        195                 200                 205

Thr Cys Ser Thr Thr Leu Ile Ala Ile Ala Gly Met Thr Cys Ala Ser
    210                 215                 220

Cys Val His Ser Ile Glu Gly Met Ile Ser Gln Leu Glu Gly Val Gln
225                 230                 235                 240

Gln Ile Ser Val Ser Leu Ala Glu Gly Thr Ala Thr Val Leu Tyr Asn
                245                 250                 255

Pro Ser Val Ile Ser Pro Glu Glu Leu Arg Ala Ala Ile Glu Asp Met
            260                 265                 270

Gly Phe Glu Ala Ser Val Val Ser Glu Ser Cys Ser Thr Asn Pro Leu
        275                 280                 285

Gly Asn His Ser Ala Gly Asn Ser Met Val Gln Thr Thr Asp Gly Thr
    290                 295                 300

Pro Thr Ser Val Gln Glu Val Ala Pro His Thr Gly Arg Leu Pro Ala
305                 310                 315                 320

Asn His Ala Pro Asp Ile Leu Ala Lys Ser Pro Gln Ser Thr Arg Ala
                325                 330                 335

Val Ala Pro Gln Lys Cys Phe Leu Gln Ile Lys Gly Met Thr Cys Ala
            340                 345                 350

Ser Cys Val Ser Asn Ile Glu Arg Asn Leu Gln Lys Glu Ala Gly Val
        355                 360                 365

Leu Ser Val Leu Val Ala Leu Met Ala Gly Lys Ala Glu Ile Lys Tyr
    370                 375                 380

Asp Pro Glu Val Ile Gln Pro Leu Glu Ile Ala Gln Phe Ile Gln Asp
385                 390                 395                 400

Leu Gly Phe Glu Ala Ala Val Met Glu Asp Tyr Ala Gly Ser Asp Gly
                405                 410                 415

Asn Ile Glu Leu Thr Ile Thr Gly Met Thr Cys Ala Ser Cys Val His
            420                 425                 430

Asn Ile Glu Ser Lys Leu Thr Arg Thr Asn Gly Ile Thr Tyr Ala Ser
        435                 440                 445

Val Ala Leu Ala Thr Ser Lys Ala Leu Val Lys Phe Asp Pro Glu Ile
    450                 455                 460

Ile Gly Pro Arg Asp Ile Ile Lys Ile Ile Glu Ser Lys Thr Ser Glu
465                 470                 475                 480

Ala Leu Ala Lys Leu Met Ser Leu Gln Ala Thr Glu Ala Thr Val Val
                485                 490                 495
```

-continued

```
Thr Leu Gly Glu Asp Asn Leu Ile Ile Arg Glu Glu Gln Val Pro Met
            500                 505                 510

Glu Leu Val Gln Arg Gly Asp Ile Val Lys Val Pro Gly Gly Lys
        515                 520                 525

Phe Pro Val Asp Gly Lys Val Leu Glu Gly Asn Thr Met Ala Asp Glu
    530                 535                 540

Ser Leu Ile Thr Gly Glu Ala Met Pro Val Thr Lys Lys Pro Gly Ser
545                 550                 555                 560

Thr Val Ile Ala Arg Ser Ile Asn Ala His Gly Ser Val Leu Ile Lys
                565                 570                 575

Ala Thr His Val Gly Asn Asp Thr Thr Leu Ala Gln Ile Val Lys Leu
            580                 585                 590

Val Glu Glu Ala Gln Met Ser Lys Asn Pro Asn Lys His Ile Ser Gln
        595                 600                 605

Thr Glu Val Ile Ile Arg Phe Ala Phe Gln Thr Ser Ile Thr Val Leu
    610                 615                 620

Cys Ile Ala Cys Pro Cys Ser Leu Gly Leu Ala Thr Pro Thr Ala Val
625                 630                 635                 640

Met Val Gly Thr Gly Val Ala Ala Gln Asn Gly Ile Leu Ile Lys Gly
                645                 650                 655

Gly Lys Pro Leu Glu Met Ala His Lys Ile Lys Thr Val Met Phe Asp
            660                 665                 670

Lys Thr Gly Thr Ile Thr His Gly Val Pro Arg Val Met Arg Val Leu
        675                 680                 685

Leu Leu Gly Asp Val Ala Thr Leu Pro Leu Arg Lys Val Leu Ala Val
    690                 695                 700

Val Gly Thr Ala Glu Ala Ser Ser Glu His Pro Leu Gly Val Ala Val
705                 710                 715                 720

Thr Lys Tyr Cys Lys Glu Glu Leu Gly Thr Glu Thr Leu Gly Tyr Cys
                725                 730                 735

Thr Asp Phe Gln Ala Val Pro Gly Cys Gly Ile Gly Cys Lys Val Ser
            740                 745                 750

Asn Val Glu Gly Ile Leu Ala His Ser Glu Arg Pro Leu Ser Ala Pro
        755                 760                 765

Ala Ser His Leu Asn Glu Ala Gly Ser Leu Pro Ala Glu Lys Asp Ala
    770                 775                 780

Val Pro Gln Thr Phe Ser Val Leu Ile Gly Asn Arg Glu Trp Leu Arg
785                 790                 795                 800

Arg Asn Gly Leu Thr Ile Ser Ser Asp Val Ser Asp Ala Met Thr Asp
                805                 810                 815

His Glu Met Lys Gly Gln Thr Ala Ile Leu Val Ala Ile Asp Gly Val
            820                 825                 830

Leu Cys Gly Met Ile Ala Ile Ala Asp Ala Val Lys Gln Glu Ala Ala
        835                 840                 845

Leu Ala Val His Thr Leu Gln Ser Met Gly Val Asp Val Val Leu Ile
    850                 855                 860

Thr Gly Asp Asn Arg Lys Thr Ala Arg Ala Ile Ala Thr Gln Val Gly
865                 870                 875                 880

Ile Asn Lys Val Phe Ala Glu Val Leu Pro Ser His Lys Val Ala Lys
                885                 890                 895

Val Gln Glu Leu Gln Asn Lys Gly Lys Lys Val Ala Met Val Gly Asp
            900                 905                 910

Gly Val Asn Asp Ser Pro Ala Leu Ala Gln Ala Asp Met Gly Val Ala
```

-continued

```
                915                 920                 925
Ile Gly Thr Gly Thr Asp Val Ala Ile Glu Ala Ala Asp Val Val Leu
    930                 935                 940
Ile Arg Asn Asp Leu Leu Asp Val Val Ala Ser Ile His Leu Ser Lys
945                 950                 955                 960
Arg Thr Val Arg Arg Ile Arg Ile Asn Leu Val Leu Ala Leu Ile Tyr
                965                 970                 975
Asn Leu Val Gly Ile Pro Ile Ala Ala Gly Val Phe Met Pro Ile Gly
            980                 985                 990
Ile Val Leu Gln Pro Trp Met Gly Ser Ala Ala Met Ala Ala Ser Ser
                995                 1000                1005
Val Ser Val Val Leu Ser Ser Leu Gln Leu Lys Cys Tyr Lys Lys Pro
        1010                1015                1020
Asp Leu Glu Arg Tyr Glu Ala Gln Ala His Gly His Met Lys Pro Leu
1025                1030                1035                1040
Thr Ala Ser Gln Val Ser Val His Ile Gly Met Asp Asp Arg Trp Arg
                1045                1050                1055
Asp Ser Pro Arg Ala Thr Pro Trp Asp Gln Val Ser Tyr Val Ser Gln
                1060                1065                1070
Val Ser Leu Ser Ser Leu Thr Ser Asp Lys Pro Ser Arg His Ser Ala
                1075                1080                1085
Ala Ala Asp Asp Asp Gly Asp Lys Trp Ser Leu Leu Leu Asn Gly Arg
                1090                1095                1100
Asp Glu Glu Gln Tyr Ile
1105                1110

(2) INFORMATION FOR SEQ ID NO:30:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:30:

Asp Lys Thr Gly
1

(2) INFORMATION FOR SEQ ID NO:31:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:31:

Asp Met Val Gly Asp Gly
1               5
```

```
(2) INFORMATION FOR SEQ ID NO:32:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:32:

Gly Met Xaa Cys Xaa Ser Cys
1               5

(2) INFORMATION FOR SEQ ID NO:33:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:33:

Thr Gly Glu Ala
1

(2) INFORMATION FOR SEQ ID NO:34:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:34:

Ser Glu His Pro Leu
1               5

(2) INFORMATION FOR SEQ ID NO:35:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:35:

Asp Lys Thr Gly Thr Ile Thr
1               5
```

(2) INFORMATION FOR SEQ ID NO:36:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:36:

GGCTACCAGG TGCACCACCA GAAGCTGGTG TTCTTCGCCG AGGACGTG          48

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:37:

ANTTCTGCCT CAGGAGTGTG AC          22

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:38:

TTCCCGGACC CCTGTTTGCT          20

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:39:

AATCCTCCTG GTGGGAGTGA GCAC          24

(2) INFORMATION FOR SEQ ID NO:40:

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:40:

AGAAGCTGGG ATGTTGTAGA AAATATTAGG                              30

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:41:

CCTATACCAC CATCCAGGAG                                         20

(2) INFORMATION FOR SEQ ID NO:42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:42:

GCCCTGAAAC CTCTTGTTCT G                                       21

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:43:

CTACTGATAA ACACAGTTGC TGGG                                    24

(2) INFORMATION FOR SEQ ID NO:44:

(i) SEQUENCE CHARACTERISTICS:
        (A) LENGTH: 26 base pairs
        (B) TYPE: nucleic acid
```

(C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:44:

CTTTGTTCGG TTATATTGAC TGTGTC                                              26

(2) INFORMATION FOR SEQ ID NO:45:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:45:

CCGTTACGCA CCCACAGTA                                                      19

(2) INFORMATION FOR SEQ ID NO:46:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:46:

TTCCATGGGA AAAGTTGAAG AATT                                                24

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:47:

AGACTCCCTG GACTGGCTTT                                                     20

(2) INFORMATION FOR SEQ ID NO:48:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:48:

GCTTTCTGCC AATGCATATT TTAAC                                              25

(2) INFORMATION FOR SEQ ID NO:49:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:49:

AGAGTTGGGC CCAGGTAGAG                                                    20

(2) INFORMATION FOR SEQ ID NO:50:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:50:

AGGGGAGTGG CTTGTAATCC                                                    20

(2) INFORMATION FOR SEQ ID NO:51:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:51:

CTTAGCGGGC AGAATATCTG AG                                                 22

(2) INFORMATION FOR SEQ ID NO:52:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:52:

CGCTCATTGA ACTCTCCTCC                                                     20

(2) INFORMATION FOR SEQ ID NO:53:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:53:

AACATGGTGT TCAGAGGAAG TGAG                                                24

(2) INFORMATION FOR SEQ ID NO:54:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:54:

CAGCTGTCTC TAACACCACG C                                                   21

(2) INFORMATION FOR SEQ ID NO:55:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:55:

AAACCACATG GGCATCTGAT                                                     20

(2) INFORMATION FOR SEQ ID NO:56:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:56:

CTATTGTAAC AGCTGGCCTA GAACC                           25

(2) INFORMATION FOR SEQ ID NO:57:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:57:

CTGTCACTTG CTCAGCCCC                                  19

(2) INFORMATION FOR SEQ ID NO:58:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:58:

GCTGTCAGGT CACATGAGTG C                               21

(2) INFORMATION FOR SEQ ID NO:59:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:59:

CTGATTTCCC AGAACTCTTC ACAT                            24

(2) INFORMATION FOR SEQ ID NO:60:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:60:

TTCTTCATAG GTTGTAATTT CCCATG                          26

(2) INFORMATION FOR SEQ ID NO:61:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:61:

GGATCAATGT CAGTAGATTA TTTAAAACAC                                      30

(2) INFORMATION FOR SEQ ID NO:62:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:62:

CCCTGAAATG TCCTTATCTG ATTAG                                           25

(2) INFORMATION FOR SEQ ID NO:63:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:63:

TCTCAAGGCT TTTCTCTCAA TGTG                                            24

(2) INFORMATION FOR SEQ ID NO:64:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:64:

CAGCTAGGAG AGAAGGACAT GG                                              22

(2) INFORMATION FOR SEQ ID NO:65:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:65:

AGTTCTGCCT CAGGAGTGTG AC                                                 22

(2) INFORMATION FOR SEQ ID NO:66:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:66:

TCTTGGCTTA CAGTTTCCTC TTCC                                               24

(2) INFORMATION FOR SEQ ID NO:67:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:67:

TCTGTGGTTT GACCCACCTC                                                    20

(2) INFORMATION FOR SEQ ID NO:68:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:68:

GACTCTTTTG CCTGATATCT GCA                                                23

(2) INFORMATION FOR SEQ ID NO:69:

(i) SEQUENCE CHARACTERISTICS:
            (A) LENGTH: 23 base pairs

-continued

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:69:

TGCTGTTAAA AGGATTGCAT GGT                                             23

(2) INFORMATION FOR SEQ ID NO:70:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:70:

CATTGCAAGT GTGGTATCTT GGT                                             23

(2) INFORMATION FOR SEQ ID NO:71:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:71:

TACAGCTCAG TGCTGGGCC                                                  19

(2) INFORMATION FOR SEQ ID NO:72:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:72:

CAAGGGTAAC TTGAGGTTTC TGC                                             23

(2) INFORMATION FOR SEQ ID NO:73:

(i) SEQUENCE CHARACTERISTICS:
        (A) LENGTH: 22 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO:73:

TCATTCTGAT GGAGAGGAGC AC                                                  22

(2) INFORMATION FOR SEQ ID NO:74:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:74:

TGGGCAGACC CCTTCCTCAC                                                     20

(2) INFORMATION FOR SEQ ID NO:75:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:75:

AAGCCTTTCT GGGCGCAGCT                                                     20

(2) INFORMATION FOR SEQ ID NO:76:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:76:

GACCTAGGTG TGAGTGCGAG TT                                                  22

(2) INFORMATION FOR SEQ ID NO:77:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:77:

GTTTAGCCAG GGCTTCTGAG G                                                     21

(2) INFORMATION FOR SEQ ID NO:78:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:78:

GGATGAGAGG CCTTCACCAG                                                       20

(2) INFORMATION FOR SEQ ID NO:79:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:79:

CTCTCCAGGT CAGGCTTCTT AT                                                    22

(2) INFORMATION FOR SEQ ID NO:80:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:80:

AATGGAGCTG ACACAGGACT G                                                     21

(2) INFORMATION FOR SEQ ID NO:81:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:81:

GCAGGTCATG CCCTCCAC                                        18

(2) INFORMATION FOR SEQ ID NO:82:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:82:

CACAACATAG AGTCCAAACT CACG                                 24

(2) INFORMATION FOR SEQ ID NO:83:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:83:

AAACTGGTGG AAGAGGCTCA G                                    21

(2) INFORMATION FOR SEQ ID NO:84:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:84:

CAGTCACTAA GAAACCCGGA AG                                   22

(2) INFORMATION FOR SEQ ID NO:85:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:85:

```
TGTCCTCACC AAGGGTCACA                                                    20
```

(2) INFORMATION FOR SEQ ID NO:86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:86:

```
GATGAGGATG CCGTTCTGCG                                                    20
```

(2) INFORMATION FOR SEQ ID NO:87:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:87:

```
GCCCAAGGGG TGTTCACT                                                      18
```

(2) INFORMATION FOR SEQ ID NO:88:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:88:

```
Asp Lys Thr Gly Thr
1               5
```

(2) INFORMATION FOR SEQ ID NO:89:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:89:

```
Thr Gly Asp Asn
1
```

(2) INFORMATION FOR SEQ ID NO:90:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:90:

```
Ala Met Val Gly Asp Gly Val Asn Asp
1               5
```

(2) INFORMATION FOR SEQ ID NO:91:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:91:

```
Ile Thr Gly Glu Ala
1               5
```

(2) INFORMATION FOR SEQ ID NO:92:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:92:

```
Thr Gly Glu Ser
1
```

(2) INFORMATION FOR SEQ ID NO:93:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:93:

```
Asp Lys Thr Gly Thr Leu Thr
1               5
```

(2) INFORMATION FOR SEQ ID NO:94:

(i) SEQUENCE CHARACTERISTICS:
    (A) LENGTH: 609 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 163..609

(xi) SEQUENCE DESCRIPTION: SEQ ID NO:94:

```
TTCCCGGACC CCTGTTTGCT TTAGAGCCGA GCCGCGCCGC GCCGATGCCC TCACACTCTG      60

CGCCTCCTCT CCCGGGACTT TAACACCACG CTCTCCTCCA CCGACCAGGT GACCTTTTGC     120

TCTGAGCCAG ATCAGAGAAG AATTCGGTGT CCGTGCGGGA CG ATG CCT GAG CAG        174
                                              Met Pro Glu Gln
                                               1

GAG AGA CAG ATC ACA GCC AGA GAA GGG GCC AGT CGG AAA ATC TTA TCT       222
Glu Arg Gln Ile Thr Ala Arg Glu Gly Ala Ser Arg Lys Ile Leu Ser
  5              10                  15                  20

AAG CTT TCT TTG CCT ACC CGT GCC TGG GAA CCA GCA ATG AAG AAG AGT       270
Lys Leu Ser Leu Pro Thr Arg Ala Trp Glu Pro Ala Met Lys Lys Ser
              25                  30                  35

TTT GCT TTT GAC AAT GTT GGC TAT GAA GGT GGT CTG GAT GGC CTG GGC       318
Phe Ala Phe Asp Asn Val Gly Tyr Glu Gly Gly Leu Asp Gly Leu Gly
          40                  45                  50

CCT TCT TCT CAG GTG GCC ACC AGC ACA GTC AGG ATC TTG GGC ATG ACT       366
Pro Ser Ser Gln Val Ala Thr Ser Thr Val Arg Ile Leu Gly Met Thr
      55                  60                  65

TGC CAG TCA TGT GTG AAG TCC ATT GAG GAC AGG ATT TCC AAT TTG AAA       414
Cys Gln Ser Cys Val Lys Ser Ile Glu Asp Arg Ile Ser Asn Leu Lys
  70                  75                  80

GGC ATC ATC AGC ATG AAG GTT TCC CTG GAA CAA GAC AGT GCC ACT GTG       462
Gly Ile Ile Ser Met Lys Val Ser Leu Glu Gln Asp Ser Ala Thr Val
 85                  90                  95                 100

AAA TAT GTG CCA TCG GTT GTG TGC CTG CAA CAG GTT TGC CAT CAA ATT       510
Lys Tyr Val Pro Ser Val Val Cys Leu Gln Gln Val Cys His Gln Ile
             105                 110                 115

GGG GAC ATG GGC TTC GAG GCC AGC ATT GCA GAA GGA AAG GCA GCC TCC       558
Gly Asp Met Gly Phe Glu Ala Ser Ile Ala Glu Gly Lys Ala Ala Ser
         120                 125                 130

TGG CCC TCA AGG TCC TTG CCT GCC CAG GAG GCT GTG GTC AAG CTC CGG       606
Trp Pro Ser Arg Ser Leu Pro Ala Gln Glu Ala Val Val Lys Leu Arg
     135                 140                 145

GTG                                                                   609
Val
```

(2) INFORMATION FOR SEQ ID NO:95:

(i) SEQUENCE CHARACTERISTICS:
    (A) LENGTH: 149 amino acids
    (B) TYPE: amino acid
    (D) TOPOLOGY: linear (ii) MOLECULE TYPE: protein (xi) SEQUENCE DESCRIPTION: SEQ ID NO:95:

```
Met Pro Glu Gln Glu Arg Gln Ile Thr Ala Arg Glu Gly Ala Ser Arg
  1               5                  10                  15

Lys Ile Leu Ser Lys Leu Ser Leu Pro Thr Arg Ala Trp Glu Pro Ala
             20                  25                  30
```

```
Met Lys Lys Ser Phe Ala Phe Asp Asn Val Gly Tyr Glu Gly Gly Leu
        35                  40                  45

Asp Gly Leu Gly Pro Ser Ser Gln Val Ala Thr Ser Thr Val Arg Ile
    50                  55                  60

Leu Gly Met Thr Cys Gln Ser Cys Val Lys Ser Ile Glu Asp Arg Ile
65                  70                  75                  80

Ser Asn Leu Lys Gly Ile Ile Ser Met Lys Val Ser Leu Glu Gln Asp
                85                  90                  95

Ser Ala Thr Val Lys Tyr Val Pro Ser Val Val Cys Leu Gln Gln Val
                100                 105                 110

Cys His Gln Ile Gly Asp Met Gly Phe Glu Ala Ser Ile Ala Glu Gly
                115                 120                 125

Lys Ala Ala Ser Trp Pro Ser Arg Ser Leu Pro Ala Gln Glu Ala Val
    130                 135                 140

Val Lys Leu Arg Val
145

(2) INFORMATION FOR SEQ ID NO:96:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:96:

His Val Val Thr Leu Gln Leu Arg Ile Asp Gly Met His Cys Lys Ser
1               5                   10                  15

Cys Val Leu Asn Ile Glu Glu Asn Ile Gly Gln Leu Leu Gly Val Gln
                20                  25                  30

Ser Ile Gln Val Ser Leu Glu Asn Lys Thr Ala Gln Val Lys Tyr Asp
            35                  40                  45

Pro Ser Cys Thr Ser Pro Val Ala Leu Gln Arg Ala Ile Glu Ala Leu
    50                  55                  60

Pro Pro Gly Asn Phe Lys Val Ser
65                  70

(2) INFORMATION FOR SEQ ID NO:97:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:97:

Ala Pro Gln Lys Cys Phe Leu Gln Ile Lys Gly Met Ile Cys Ala Ser
1               5                   10                  15

Cys Val Ser Asn Ile Glu Arg Asn Leu Gln Lys Glu Ala Gly Val Leu
                20                  25                  30

Ser Val Leu Val Ala Leu Met Ala Gly Lys Ala Glu Ile Lys Tyr Asp
            35                  40                  45

Pro Glu Val Ile Gln Pro Leu Glu Ile Ala Gln Phe Ile Gln Asp Leu
    50                  55                  60

Gly Phe Glu Ala Ala Val Met Glu
```

65                  70

(2) INFORMATION FOR SEQ ID NO:98:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:98:

Ser Asp Gly Asn Ile Glu Leu Thr Ile Thr Gly Met Ile Cys Ala Ser
1               5                   10                  15

Cys Val His Asn Ile Glu Ser Lys Leu Thr Arg Thr Asn Gly Ile Thr
                20                  25                  30

Tyr Ala Ser Val Ala Leu Ala Thr Ser Lys Ala Leu Val Lys Phe Asp
            35                  40                  45

Pro Glu Ile Ile Gly Pro Arg Asp Ile Ile Lys Ile Ile Glu Glu Ile
        50                  55                  60

Gly Phe His Ala Ser Leu Ala Gln
65                  70

(2) INFORMATION FOR SEQ ID NO:99:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:99:

Gln Glu Ala Val Val Lys Leu Arg Val Glu Gly Met Ile Cys Gln Ser
1               5                   10                  15

Cys Val Ser Ser Ile Glu Gly Lys Val Arg Lys Leu Gln Gly Val Val
                20                  25                  30

Arg Val Lys Val Ser Leu Ser Asn Gln Glu Ala Val Ile Thr Tyr Gln
            35                  40                  45

Pro Tyr Leu Ile Gln Pro Glu Asp Leu Arg Asp His Val Asn Asp Met
        50                  55                  60

Gly Phe Glu Ala Ala Ile Lys Ser
65                  70

(2) INFORMATION FOR SEQ ID NO:100:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:100:

Thr Cys Ser Thr Thr Leu Ile Ala Ile Ala Gly Met Ile Cys Ala Ser
1               5                   10                  15

Cys Val His Ser Ile Glu Gly Met Ile Ser Gln Leu Glu Gly Val Gln
                20                  25                  30

Gln Ile Ser Val Ser Leu Ala Glu Gly Thr Ala Thr Val Leu Tyr Asn
            35                  40                  45

```
Pro Ser Val Ile Ser Pro Glu Glu Leu Arg Ala Ala Ile Glu Asp Met
    50                  55                  60

Gly Phe Glu Ala Ser Val Val Ser
65                  70

(2) INFORMATION FOR SEQ ID NO:101:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:101:

Gln Val Ala Thr Ser Thr Val Arg Ile Leu Gly Met Ile Cys Gln Ser
1               5                   10                  15

Cys Val Lys Ser Ile Glu Asp Arg Ile Ser Asn Leu Lys Gly Ile Ile
                20                  25                  30

Ser Met Lys Val Ser Leu Glu Gln Asp Ser Ala Thr Val Lys Tyr Val
            35                  40                  45

Pro Ser Val Val Cys Leu Gln Gln Val Cys His Gln Ile Gly Asp Met
    50                  55                  60

Gly Phe Glu Ala Ser Ile Ala Glu
65                  70

(2) INFORMATION FOR SEQ ID NO:102:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:102:

Gln Val Ala Thr Ser Thr Val Arg Ile Leu Gly Met Ile Cys Gln Ser
1               5                   10                  15

Cys Val Lys Ser Ile Glu Asp Arg Ile Ser Asn Leu Lys Gly Ile Ile
                20                  25                  30

Ser Met Lys Val Ser Leu Glu Gln Asp Ser Ala Ile Val Lys Tyr Val
            35                  40                  45

Pro Ser Val Val Cys Leu Gln Gln Val Cys His Gln Ile Gly Asp Met
    50                  55                  60

Gly Phe Glu Ala Ser Ile Ala Glu
65                  70

(2) INFORMATION FOR SEQ ID NO:103:

(i) SEQUENCE CHARACTERISTICS:
        (A) LENGTH: 71 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:103:

His Val Val Thr Leu Gln Leu Arg Ile Asp Gly Met His Cys Lys Ser
1               5                   10                  15
```

```
Cys Val Leu Asn Ile Glu Glu Asn Ile Gly Gln Leu Gly Val Gln Ser
            20                  25                  30

Ile Gln Val Ser Leu Glu Asn Lys Thr Ala Gln Val Lys Tyr Asp Pro
            35                  40                  45

Ser Cys Thr Ser Pro Val Ala Leu Gln Arg Ala Ile Glu Ala Leu Pro
            50                  55                  60

Pro Gly Asn Phe Lys Val Ser
 65              70
```

(2) INFORMATION FOR SEQ ID NO:104:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:104:

```
Gln Glu Ala Val Val Lys Leu Arg Val Glu Gly Met Thr Cys Gln Ser
 1               5                  10                  15

Cys Val Ser Ser Ile Glu Gly Lys Val Arg Lys Leu Gln Gly Val Val
            20                  25                  30

Arg Val Lys Val Ser Leu Ser Asn Gln Glu Ala Val Ile Thr Tyr Gln
            35                  40                  45

Pro Tyr Leu Ile Gln Pro Glu Asp Leu Arg Asp His Val Asn Asp Met
            50                  55                  60

Gly Phe Glu Ala Ala Ile Lys Ser
 65              70
```

(2) INFORMATION FOR SEQ ID NO:105:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

```
Thr Cys Ser Thr Thr Leu Ile Ala Ile Ala Gly Met Thr Cys Ala Ser
 1               5                  10                  15

Cys Val His Ser Ile Glu Gly Met Ile Ser Gln Leu Glu Gly Val Gln
            20                  25                  30

Gln Ile Ser Val Ser Leu Ala Glu Gly Thr Ala Thr Val Leu Tyr Asn
            35                  40                  45

Pro Ser Val Ile Ser Pro Glu Glu Leu Arg Ala Ala Ile Glu Asp Met
            50                  55                  60

Gly Phe Glu Ala Ser Val Val Ser
 65              70
```

(2) INFORMATION FOR SEQ ID NO:106:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:106:

Glu Val Lys Lys Tyr Arg Val Asn Val Gln Gly Met Thr Cys Ser Gly
1               5                   10                  15

Cys Glu Gln His Val Ala Val Ala Leu Glu Asn Met Gly Ala Lys Ala
            20                  25                  30

Ile Glu Val Asp Phe Arg Arg Gly Glu Ala Val Phe Glu Leu Pro Asp
        35                  40                  45

Asp Val Lys Val Glu Asp Ala Lys Asn Ala Ile Ala Asp Ala Asn Tyr
    50                  55                  60

His Pro Gly Glu Ala Glu Phe
65                  70

(2) INFORMATION FOR SEQ ID NO:107:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

Glu Val Lys Lys Tyr Arg Leu Asn Val Glu Gly Met Thr Cys Ile Gly
1               5                   10                  15

Cys Glu Glu His Ile Ala Val Ala Leu Glu Asn Ala Gly Ala Lys Gly
            20                  25                  30

Ile Glu Val Asp Phe Arg Arg Gly Glu Ala Leu Phe Glu Leu Pro Tyr
        35                  40                  45

Asp Val Asp Ile Asp Ile Ala Lys Ile Ala Ile Thr Asp Ala Gln Tyr
    50                  55                  60

Gln Pro Gly Glu Ala Glu Glu Ile
65                  70

ISOLATION AND USES OF A WILSON'S DISEASE GENE

This application is 371 of PCT/US94/09851, filed Sep. 1, 1994, which is a continuation-in-part of U.S. application Ser. No. 08/118,441, filed Sep. 1, 1993, now U.S. Pat. No. 5,578,493 the contents of which are hereby incorporated by reference.

The invention disclosed herein was made with Government support under NIH Grant No. NS28877 and HG00462 from the Department of Health and Human Services. Accordingly, the U.S. Government has certain rights in this invention.

BACKGROUND OF THE INVENTION

Throughout this application, various references are referred to within parenthesis. Disclosures of these publication in their entireties are hereby incorporated by reference into this application to more fully describe the state of the art to which this invention pertains. Full bibliographic citation for these references may be found at the end of each series of experiments in the Experimental Details section.

Wilson's disease (WD) is an autosomal recessive disorder of copper metabolism with a world-wide prevalence of 30 per million and a corresponding carrier frequency of 1 in 90. Biochemically it is characterized by abnormally high concentrations of copper in a number of organs and tissues, and deficiency of the plasma copper-protein, ceruloplasmin. The excess copper causes damage to the liver and brain. In the former, acute and chronic hepatic disease progresses to cirrhosis; in the latter motor and psychiatric disturbances reflect the cerebral pathology. Clinical onset may occur in the latter half of the first decade, is most frequent in adolescence, and was delayed in two patients until the seventh decade. Untreated, the disease is always fatal but pharmacologic removal or detoxification of the excess copper is prophylactic in the asymptomatic patient and can be dramatically effective therapy for patients with hepatic or cerebral symptomatology. The mechanism by which the abnormal gene disturbs copper homeostasis is unknown (1).

In 1985, genetic linkage studies showed that the Wilson's disease locus segregates with the red cell enzyme esterase-D (ESD) on chromosome 13 (2). Subsequent linkage analyses limited the disease locus to a genomic region bracketed by the DNA marker loci D13S31 and D13S59, although the odds for a disease locus in the adjacent interval between loci D13S31 and D13S25 were estimated to be only seven times less likely (3).

SUMMARY OF THE INVENTION

This invention provides an isolated, vertebrate nucleic acid molecule encoding the normal polypeptide which prevents development of Wilson's disease. This invention also provides the above-described isolated, vertebrate nucleic acid molecule operatively linked to a promoter of RNA transcription.

This invention also provides a nucleic acid molecule comprising a nucleic acid molecule of at least 15 nucleotides capable of specifically hybridizing with a sequence included within the sequence of the nucleic acid molecule encoding the normal polypeptide which prevents development of Wilson's disease.

This invention provides a host vector system for the production of a polypeptide which prevents the development of Wilson's disease.

This invention further provides the normal polypeptide which prevents development of Wilson's disease.

This invention also provides an antibody capable of binding to polypeptide encoded by an isolated, vertebrate nucleic acid molecule encoding the normal polypeptide which prevents development of Wilson's disease.

This invention further provides a method for diagnosing Wilson's disease in a subject comprising: (a) obtaining nucleic acid sample from the subject; (b) reverse-transcribing the RNA to cDNA if the obtained nucleic acid from step (a) is RNA; (c) cleave the DNA sample into fragments; (d) separating the DNA fragments by size fractionation; (e) hybridizing the DNA fragments with a nucleic acid molecule comprising a nucleic acid molecule of at least 15 nucleotides capable of specifically hybridizing with a sequence included within the sequence of the nucleic acid molecule encoding the normal polypeptide which prevents development of Wilson's disease; and (f) comparing the detected DNA fragment from (d) with the DNA fragment from a known normal subject, the difference in size of the fragments indicating the occurrence of Wilson's disease in the subject.

This invention provides a method for diagnosing Wilson's disease in a subject comprising: (a) obtaining RNA sample from the subject; (b) separating the RNA sample into different species by size fractionation; (c) hybridizin g the RNA species with a nucleic acid molecule comprising a nucleic acid molecule of at least 15 nucleotides capable of specifically hybridizing with a sequence included within the sequence of the nucleic acid molecule encoding the normal polypeptide which prevents development of Wilson's disease; and (d) comparing the detected RNA species from step (c) with the RNA species from a known normal subject, the difference in size of the species indicating the occurrence of Wilson's disease in the subject.

This invention provides a method for diagnosing Wilson's disease in a subject comprising: (a) obtaining nucleic acid sample from the subject; (b) amplifying the nucleic acids; (c) separating and analyzing the amplified nucleic acids obtained in step (b) by Single-Stranded Conformational Polymorphism Analysis to determine the occurrence of Wilson's disease in the subject.

This invention provides a pharmaceutical composition comprising the normal polypeptide which prevents the development of Wilson's disease effective to reduce the symptom of Wilson's disease and a pharmaceutically acceptable carrier.

This invention provides a method for reducing the symptom of Wilson's disease in a subject which comprises replacing the subject's Wilson's disease gene with the nucleic acid molecule encoding the normal polypeptide which prevents development of Wilson's disease so as to reduce the symptom of Wilson's disease.

This invention provides a transgenic nonhuman mammal which comprises the isolated nucleic acid molecule encoding the normal polypeptide which prevents development of Wilson's disease.

BRIEF DESCRIPTION OF THE FIGURES

FIG. 5 DNA sequence of pWD and translated amino-acid sequence (SEQ ID NOS: 28 and 29). Shadow regions correspond to the transmembrane helices. Square boxes represent consensus sequences found in related ATPase proteins, including: metal ending sites 1–5, phosphatase/transduction domain; phosphorylation site; and nucleotide binding site and hinge domain. Shadowed dinucleotide sequences correspond to sequences missing in the Mc1 (Menkes) gene, respectively 2, 4, 4, 3, 18 and 1 amino acid residue. Striped dinucleotide sequences correspond to additional sequences found in the Mc1 gene, respectively 179, 45, 11 and 6 residues.

FIG. 6 Consensus regions found in the most homologous proteins using the BLAST program (12 of the second series of experiments) (SEQ ID NOS: 33 and 91 (FIG. 6-1); SEQ ID NOS: 35 and 93 (FIG. 6-2); SEQ ID NO: 21 (FIG. 6-3); SEQ ID NO: 20 (FIG. 6-4). Shadow lines indicate conserved residues whereas stars indicate strongly homologous residues. Dots, above the sequences are plotted every ten residues. The database, protein name, and access numbers corresponding to proteins lited in the figure are as follows: SWISSPROT: K+ATPase (*E. Faecalis*). P05425; Cd ATPase, P20021; Fixl, P18398; K+ATPase (*E. Coli*), P03960; H+ATPase 1, P05030; E1–E2 ATPase 1A, P11718; H+ATPase2, P28876; Mg++ATPase, P22036; E1–E2 ATPase P07893; Hg++reductase, P08662; Hg++transport protein, P13113. GENBANK: Mc1, L06133; CopA, L13292; ATPaseS.C., J04421; Ca++ATPase, M83363; CadA, L10909; NR1 Hg++resistance, K03089; Hg++ resistance, L04303. PIR: H+/K+ATPase, D42707, Hypothetical protein 3, S18588.

FIG. 9 Site of the Wilson's disease mutation (SEQ ID NOS: 23–27). Sequence conservation unique to heavy-metal binding P-type ATPases is shown (34 of the second series of experiments). The H (histidine) residue at position 714 is transverted to glutamine in a predicted 25%–30% of WD chromosomes from the U.S. and Russian clinical samples (6). The CPC residues are located in the transmembrane region, 7 amino acid residues 5' to the single proline (P), which is likewise 34 amino acids 5' to the DKTG (SEQ ID No. 30) motif. The histidine is located another 39 amino acids 3' from the DKTG (SEQ ID No. 30) motif.

FIG. 10 Nucleotide sequence of the 5'-end of the WD cDNA (SEQ ID NOS: 94 and 95). An initiating methionine as well as the first methionine of the cDNA sequence presented in (4 of the third series of experiments) is underlined. The last GTG triplet of this sequence corresponds to the first triplet of the previously reported (2 of the third series of experiments) WD cDNA sequence.

FIG. 15 Determination of length of the metal-binding site by multiple amino acid sequence alignments. Shadowed boxes represent consensus sequences; isofunctional substitutions are shadowed. (A) Six 72 amino acid long fragments (SEQ ID NOS: 96–101) each containing GMXCXSC (SEQ ID No. 32) "copper-binding" motif were aligned starting 10 amino acids upstream of GMXCXSC (SEQ ID No. 32). Homologous residues were found to be spread along the 72 amino acid long fragment. (B) Amino acid (SEQ ID NOS: 102 and 103) and (C) carboxy terminal boundaries of metal-binding sites were determined by pair by pair alignment of WD protein copper-binding repeats (SEQ ID NOS: 104 and 105). Only two representative alignments are shown. (D) Alignment of two mercury binding regions from bacterial mercury reductase revealed the same length of metal-binding motifs as in the WD protein (SEQ ID NOS: 106 and 107).

DETAILED DESCRIPTION OF THE INVENTION

Figure 1:
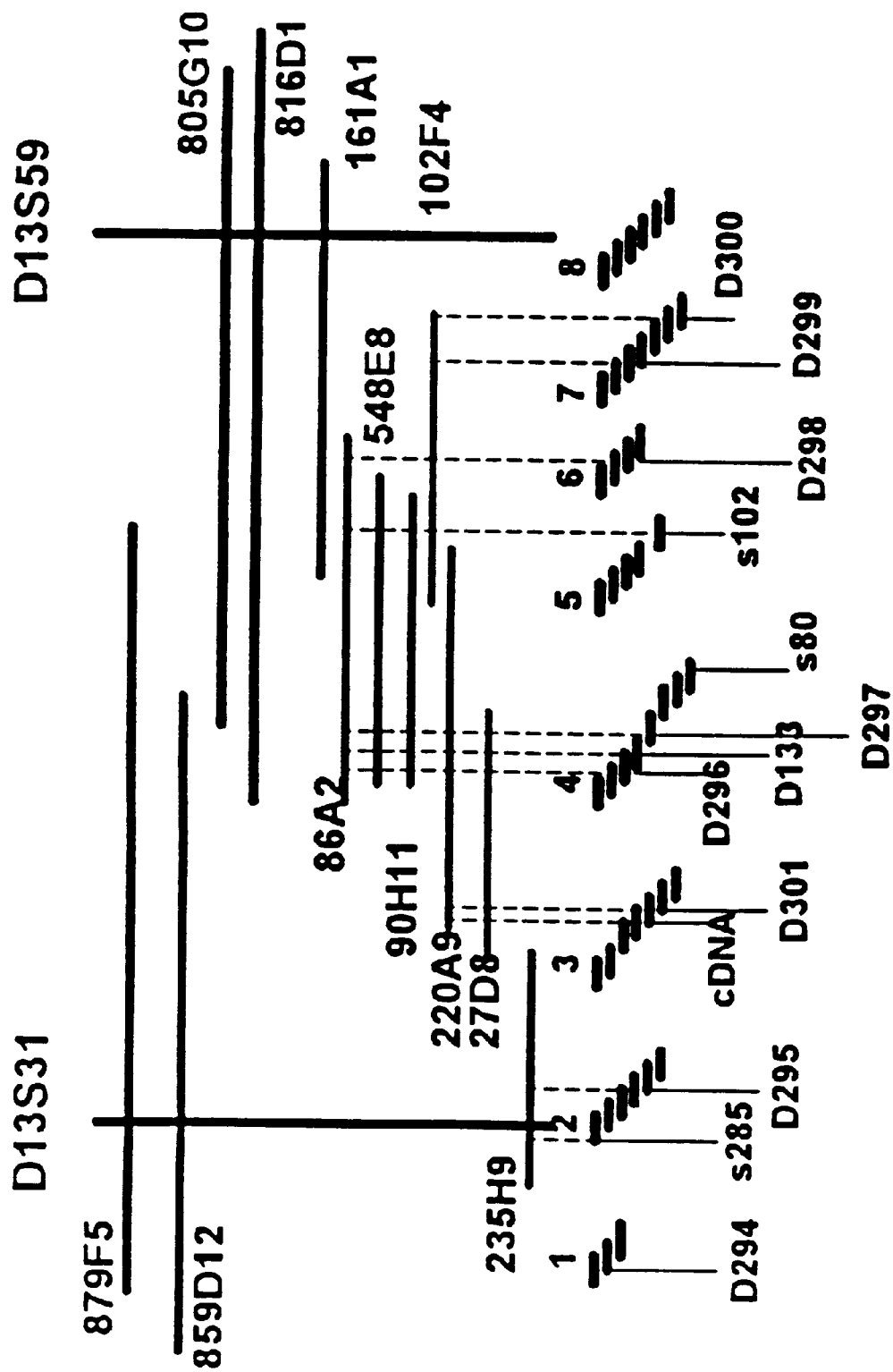
FIG. 1 Physical Map of the Wilson's disease region Loci D13S31 is the centromeric flanking marker and D13S59 the telomeric flanking marker for the WD locus (3). The top four horizontal lines represent large-insert YAC clones (15). The 8 mid-size YAC clones are from a chromosome 13-enriched sublibrary (5) selected from the CEPH I genomic YAC library (4). At the bottom of the figure are the minimum number of overlapping cosmid clones which span each island. Microsatellite markers are shown at the bottom of the figures along with several sequence tag site (STS) sequences and a WD candidate cDNA clone. Cosmid and YAC clones bearing he microsatellite and STS sequences are identified by the intersection of vertical and horizontal lines. The large-insert YAC clones (and 161A1) were not typed for the PCR markers. Clone nomenclature corresponds to the original libraries. Primer pairs and heterozygosity values for the new microsatellite markers are as follows: D13S294 (0.82)—CCCAGTGAGCAGCCTCTAAA (SEQ ID No. 3) and AACAGAAATCAGGCCAGTGTG (SEQ ID No. 4); D13S295 (0.68)—CTGCCACCTATTTTTGTAAATAAAG (SEQ ID No. 5) and TGATCTGGTGGTTCAACTGG (SEQ ID No. 6); D13S301 (0.77) —ATCATACCTGGTTGTG-CAACC (SEQ ID No. 7) and CCAGATGCT-TCTTTCTAAACACACA (SEQ ID No. 8); D13S296 (0.77) CAAACTTTTAGTATGAGTCTATCTCTCT (SEQ ID No. 9) and TCATTAAAGTGAGGAGTGAGGTAAATG (SEQ ID No. 10); D13S197 (0.69) —TTATGATG-AAAAAAGTAATATAAGAGGTCCC (SEQ ID No. 11) and AGCTGTATCTGGGGTTGG (SEQ ID No. 12); D13S298 (0.72) —AGTTTCTACATGAATAAAATCGT-ACTAGAAG (SEQ ID No. 13) and GGTATCTTG-TATAATACTACCTTCCATCA (SEQ ID No. 14); D13S299 (0.79) —TTTAACTGGCATGTTAATCTGGG (SEQ ID No. 15) and CTCCCCCTCCTTGCCTGCAACT (SEQ ID No. 16); D13S300 (0.76)—CCTGGAACTGGAAGATG-GCA (SEQ ID No. 17) and GGAGTTGGGGAGADCCA-CAAT (SEQ ID No. 18).
Figure 2A:
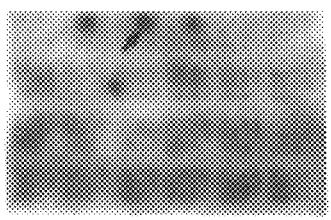
FIG. 2 Pattern hybridization to construct cosmid contigs. Each of the 283 "positive" cosmids was radiolabelled at both ends using the Riboprobe method (see Methods) and hybridized simultaneously to an ordered array blot containing the same 283 cosmids. For example, frame (A) shows the 3a3 cosmid end-clone mixture identifying itself (arrow) and clones 3a4, 2a2 and 5b3. The configuration of cosmid overlap is illustrated at the bottom of the figure. Order was determined in larger contigs with the assistance of a tree-building algorithm (5, 6).
Figure 2B:
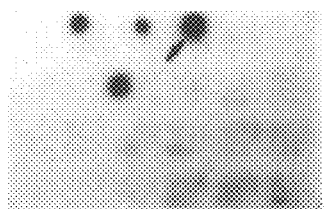
Figure 2C:
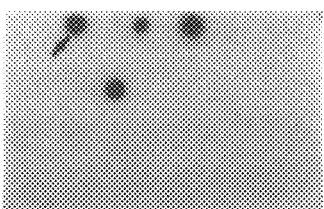
Figure 2D:
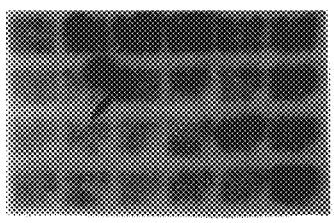
Figure 2E:
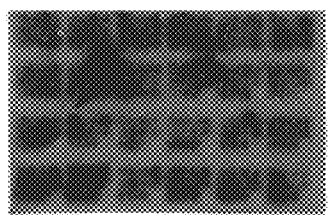
Figure 2F:
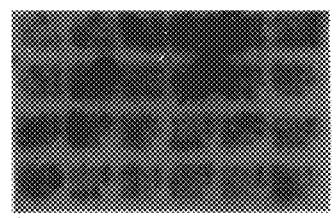
Figure 2G:
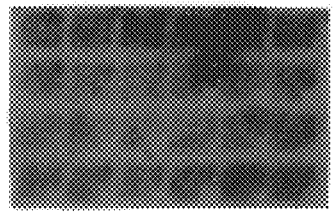
Figure 2H:
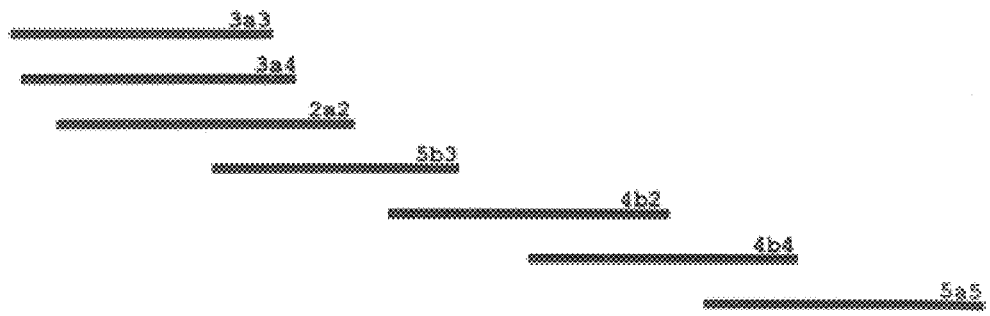

This invention provides an isolated, vertebrate nucleic acid molecule encoding the normal polypeptide which prevents development of Wilson's disease.

In an embodiment, the nucleic acid molecule is DNA. In a further embodiment, the DNA is a cDNA. In another further embodiment, the DNA is genomic DNA.

In another embodiment of this invention, the nucleic acid molecule is RNA.

In a preferred embodiment, the above described nucleic acid molecule is encoding a human polypeptide which prevents development of Wilson's disease.

This invention also encompasses DNAs and cDNAs which encode amino acid sequences which differ from the polypeptide which prevents development of Wilson's disease, but which should not produce phenotypic changes. Alternatively, this invention also encompasses DNAs and cDNAs which hybridize to the DNA and cDNA of the subject invention. Hybridization methods are well known to those of skill in the art.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

This invention also provides a nucleic acid molecule comprising a nucleic acid molecule of at least 15 nucleotides capable of specifically hybridizing with a sequence included within the sequence of the above-described nucleic acid molecule. This molecule may either be a DNA or RNA molecule.

This nucleic acid molecule produced can either be DNA or RNA. As used herein, the phrase "specifically hybridizing" means the ability of a nucleic acid molecule to recognize a nucleic acid sequence complementary to its own and to form double-helical segments through hydrogen bonding between complementary base pairs.

This nucleic acid molecule of at least 15 nucleotides capable of specifically hybridizing with a sequence of a nucleic acid molecule encoding the normal polypeptide which prevents the development of Wilson's disease can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes a polypeptide which prevents the development of Wilson's disease into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the above-described DNA molecule downstream of a bacteriophage promoter such as T3, T7 or SP6. Large amounts of RNA probe may be produced by incubating the labeled nucleotides with the linearized fragment where it contains an upstream promoter in the presence of the appropriate RNA polymerase.

These probes are useful for detecting the expression of Wilson's disease gene. These probes are also useful for "in situ" hybridization to locate tissues which express this gene, or for other hybridization assays for the presence of this gene or its mRNA in various biological tissues.

This invention further provides the above-described isolated, vertebrate nucleic acid molecule operatively linked to a promoter of RNA transcription.

The isolated above-described isolated nucleic acid molecule can be linked to different vector systems. Various vectors including plasmid vectors, cosmid vectors, bacteriophage vectors and other viruses are well known to ordinary skilled practitioners. This invention further provides a vector which comprises the isolated nucleic acid molecule encoding for the normal polypeptide which prevents the development of Wilson's disease.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

In an embodiment, the above-described molecule is cloned in a plasmid. This plasmid is designated pWD 5'-191 (See FIG. 3). An 0.85 kb insert can be cut ou t from the 2.9 kb vector by double digestion with Not1 and Sfi1. Plasmid pWD5'-191 was deposited on Sep. 1, 1993 with the American Type culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pWD 5'-191, has been accorded ATCC Accession Number 75544.

In another embodiment, the above-described molecule is cloned in a plasmid. This plasmid is designated pWD3'-1 (See FIG. 3). The size of the linear plasmid after cutting with NotI is 4.8 kb. This plasmid pWD3'-1 was deposited on Sep. 1, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid pWD3'-1 has been accorded ATCC Accession Number 75546.

In still another embodiment, the above-described molecule is cloned in a plasmid. This plasmid is designated pWD3'-3 (See FIG. 3). The size of the linear plasmid after cutting with NotI is 5.36 kb. Plasmid, pWD3'-3 was deposited on Sep. 1, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pWD3'-3, was accorded ATCC Accession Number 75545.

In an embodiment, the above-described molecule is cloned in a plasmid. This plasmid is designated pWD02 (See FIG. 3). A 3.5 kb insert can be cut out from the 2.9 kb vector by digestion with NotI. This plasmid pWD02 was deposited on Sep. 1, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid pWD02 was accorded ATCC Accession Number 75543.

This invention further provides a host vector system for the production of a polypeptide having the biological activity of the normal development polypeptide which prevents Wilson's disease. These vectors may be transformed into a suitable host cell to form a host cell vector system for the production of a polypeptide having the biological activity of the normal polypeptide which prevents the development of Wilson's disease.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the polypeptide which prevents the Wilson's disease.

This invention further provides an isolated DNA or cDNA molecule described hereinabove wherein the host cell is selected from the group consisting of bacterial cells (such as E.coli), yeast cells, fungal cells, insect cells and animal cells. Suitable animal cells include, but are not limited to Vero cells, HeLa cells, Cos cells, CV1 cells and various primary mammalian cells.

This invention provides a mammalian cell comprising a DNA molecule encoding a polypeptide which prevents Wilson's disease, such as a mammalian cell comprising a plasmid adapted for expression in a mammalian cell, which comprises a DNA molecule encoding a polypeptide which prevents Wilson's disease and the regulatory elements necessary for expression of the DNA in the mammalian cell so located relative to the DNA encoding a polypeptide which prevents Wilson's disease as to permit expression thereof.

Numerous mammalian cells may be used as hosts, including, but not limited to, liver stem cells, the mouse fibroblast cell NIH3T3, CHO cells, HeLa cells, Ltk⁻ cells, Cos cells, etc. Expression plasmids such as that described supra may be used to transfect mammalian cells by methods well known in the art such as calcium phosphate precipitation, electroporation or DNA encoding the polypeptide which prevents the development of Wilson's disease may be otherwise introduced into mammalian cells, e.g., by microinjection, to obtain mammalian cells which comprise DNA, e.g., cDNA or a plasmid, encoding a polypeptide which prevents the development of Wilson's disease.

This invention also provides a method of producing a polypeptide which prevents development of Wilson's disease which comprises growing the above-described host vector system under suitable conditions permitting production of the polypeptide and recovering the polypeptide so produced.

This invention also provides a polypeptide encoded by the above-described isolated, vertebrate nucleic acid molecule.

This invention also provides an antibody capable of binding to polypeptide encoded by the above-described nucleic acid molecule. In an embodiment, the antibody is a monoclonal antibody.

Polyclonal antibodies against the polypeptides may be produced by immunizing animals using the polypeptide which prevents development of Wilson's disease, produced by the above method. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of the polypeptide which prevents the Wilson's disease in living animals, in humans, or in biological tissues or fluids isolated from animals or humans.

Synthetic peptides corresponding to different region of the polypeptide which prevents development of Wilson's disease may be made and they may be used as antigens to generate both polyclonal and monoclonal antibodies capable of binding to the polypeptide.

This invention provides a method for diagnosing Wilson's disease in a subject comprising: (a) obtaining nucleic acid sample from the subject; (b) reverse-transcribing the RNA to cDNA if the obtained nucleic acid from step (a) is RNA; (c) cleave the DNA sample into fragments; (d) separating the DNA fragments by size fractionation; (e) hybridizing the DNA fragments with a nucleic acid molecule comprising a nucleic acid molecule of at least 15 nucleotides capable of specifically hybridizing with a sequence included within the sequence of the nucleic acid molecule encoding the normal polypeptide which prevents development of Wilson's disease, produced by the above method; and (f) comparing the detected DNA fragment from (d) with the DNA fragment from a known normal subject, the difference in size of the fragments indicating the occurrence of Wilson's disease in the subject.

One approach for performing molecular diagnosis is by allele-specific oligomer (ASO) hybridization (Kerem et al., (1989) *Science*, vol. 245:1073–1080). This approach can be used for molecular diagnosis of Wilson's disease because the Wilson's disease gene is now disclosed.

This invention also provides the above method for diagnosing Wilson's disease in a subject, further comprising amplification of the DNA obtained after step (b) by PCR technology.

PCR technology has been well-known to an ordinary skilled artisan. U.S. Pat. No. 4,683,202 by Mullis discloses a process for amplifying any desired specific nucleic acid sequence contained in a nucleic acid or mixture thereof using PCR technology. The content of U.S. Pat. No. 4,683,202 is incorporated in here by reference.

In an embodiment of the above method, the DNA sample is cleaved by restriction enzyme.

This invention further provide the above method, wherein the size fractionation is step (d) is effected by a polyacrylamide or agarose gel.

In an embodiment, the nucleic acid molecule is labeled with a detectable marker. In a further embodiment, the detectable marker is a radiolabelled molecule, a fluorescent molecule, an enzyme, or a ligand.

This invention further provides the above method further comprising transferring the DNA fragments into a solid matrix before step (e).

This invention also provides a method for diagnosing Wilson's disease in a subject comprising: (a) obtaining RNA sample from the subject; (b) separating the RNA sample into different species by size fractionation; (c) hybridizing the RNA species with a nucleic acid molecule comprising a nucleic acid molecule of at least 15 nucleotides capable of specifically hybridizing with a sequence included within the sequence of the nucleic acid molecule encoding the normal polypeptide which prevents development of Wilson's disease, produced by the above method; and (d) comparing the detected RNA species from step (c) with the RNA species from a known normal subject, the difference in size of the species indicating the occurrence of Wilson's disease in the subject.

In an embodiment, the size fractionation in step (b) is effected by a polyacrylamide or agarose gel. In another embodiment, in step (c), the nucleic acid molecule is labeled with a detectable marker. In a further embodiment, the detectable marker is a radiolabelled molecule, a fluorescent molecule, an enzyme, or a ligand.

This invention further provides the above method further comprising transferring the RNA species into a solid matrix before step (c).

This invention provides a method for diagnosing Wilson's disease in a subject comprising: (a) obtaining nucleic acid sample from the subject; (b) amplifying the nucleic acids; (c) separating and analyzed the amplified nucleic acids obtained in step (b) by single-stranded conformational analysis (SSCPA) to determine the occurrence of Wilson's disease in the subject.

Orita et al. reported that single base substitutions in short DNA segments (up to about 250 bp) can be detected as shifts in electrophoretic mobility (19, 20). The base substitution causes the DNA segment to assume a unique folded conformation, which alters its mobility on a non-denaturing gel compared to the corresponding unmutated DNA segment. The strategy is to amplify the desired segment of a gene by the PCR (21), and then to compare the migration pattern of the denatured DNA with that of a reference segment of known sequence. The "single strand conformational polymorphism" (SSCP) assay is simple, rapid, and sensitive, and has now been used for detection of point mutations in several studies (22, 23, 24, 25, 26). The SSCP can be applied to both DNA or RNA samples.

This invention provides the above method further comprising synthesizing cDNA copy of the nucleic acid if the nucleic acid sample is RNA.

In an embodiment, the nucleic acid is amplified by PCR technology.

This invention also provides a pharmaceutical composition comprising the polypeptide which is encoded by the above-described isolated, vertebrate nucleic acid molecule which encodes the normal protein that prevents development of Wilson's disease effective to reduce the symptom of Wilson's disease and a pharmaceutically acceptable carrier.

For the purpose of this invention, "Pharmaceutically acceptable carrier" means any of the standard pharmaceutical carriers. Examples of suitable carriers are well-known in the art and may include, but not limited to, any of the standard pharmaceutical vehicles such as a phosphate buffered saline solution, phosphate buffered saline containing Polysorb 80, water, emulsions such as oil/water emulsion and various types of wetting agents.

This invention provides a method for reducing the symptom of Wilson's disease in a subject which comprises replacing the subject's Wilson's disease gene with the above-described nucleic acid molecule which encodes the normal protein that prevents development of Wilson's disease so as to reduce the symptom of Wilson's disease.

"Gene therapy" approach is well known to people in the field. With the discovery of the normal Wilson's disease gene, the mutated disease gene can be replaced by this normal gene.

Finally, this invention also provides a transgenic nonhuman mammal which comprises the isolated nucleic acid molecule encoding a polypeptide which prevents development of Wilson's disease. This invention further provides a transgenic nonhuman mammal whose genome comprises antisense DNA complementary to DNA encoding a polypeptide which prevents development of Wilson's disease so placed as to be transcribed into antisense mRNA complementary to mRNA encoding the polypeptide which prevents development of Wilson's disease and which hybridizes to mRNA encoding the polypeptide which prevents development of Wilson's disease thereby reducing its translation.

One means available for producing a transgenic animal, with a mouse as an example, is as follows: Female mice are mated, and the resulting fertilized eggs are dissected out of their oviducts. The eggs are stored in an appropriate medium such as M2 medium (16). DNA or cDNA encoding a polypeptide which prevents development of Wilson's disease is purified from a vector by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Another approach is to generate "knock out" transgenic mouse where the Wilson's disease gene is rendered nonfunctional. DeChiara, T. M. et al. (1991), Cell, vol. 64:849–859, discloses this general approach via stem cells. First, the Wilson's disease gene of the mouse stem cell will be altered so that it will no longer be functional. Second, the stem cell with the "knock out" gene will be introduced to the blastocyte and the mouse developed will be a "knock out" mouse.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods
Library Screening Chromosome 13-specific Cosmid Library
A flow-sorted, arrayed chromosome 13 cosmid library was obtained from Los Alamos Laboratories (N. Brown, J. Longmire, and L. Deaven). The 16,896 clone library was arrayed on 11 Hybond N+ (Amersham) nylon membranes, each with 1536 clones.

Chromosome 13-specific CEPH I YAC Library
The 52,800 clone Centre d'Etude Polymorphism Humain (CEPH) I YAC library (4) (average insert size, 300–400 kb) was screened with hybridization probes prepared by inter-Alu PCR amplification (10) of the monochromosomal 13 cell hybrid, GM10898. 1421 clones were identified, 86% of which were shown by in situ hybridization to contain chromosome 13 DNA sequences (5).

Chromosome 13-specific CEPH II YAC Library
The large insert CEPH library (400–1200 kb) was likewise screened with inter-Alu PCR probe (I. Chumakov, unpublished; 5) to identify 819 CH13 enriched YAC clones. Replicate copies of the two YAC sublibraries were used to map the WD gene region. High density colony filters were prepared with a Biomek™ 1000 Automated Laboratory Workstation (Beckman). YAC and cosmid colony filters were grown and hybridized as described (5).

Inter-Alu PCR
Primers alu 1:5'-GGA TTA CAG GYR TGA GCC A (SEQ ID No. 1)-3' and alu 2:5'-RCC AYT GCA CTC CAG CCT G (SEQ ID No. 2) 3' (R=purines; Y=pyrimidines) were added to a final concentration of 1 $\mu$M each together with 1 ng/100 ul yeast (YAC) DNA as described (5). The PCR products were purified and concentrated to 50–100 ng/$\mu$l with a Cericon 100 microconcentrator (Amicon) or MagicPCR Prep Kit (Promega®).

Construction of Cosmid Contigs
Cosmid DNA was isolated from 5 ml overnight cultures as described (5). 1 ug of each cosmid DNA was incubated with T3 and T7 RNA polymerase, pre-annealed with denatured human placental DNA, and hybridized to cosmid colony filters as described (5). Clones identified by hybridization to cosmid riboprobe pairs were entered into a database and contigs were constructed by a tree-building algorithm (5, 6).

Identification of Microsatellite Markers
Dinucleotide repeat sequence markers were developed directly from cosmid clones as described previously (7). Allele frequencies were determined from the "normal chromosomes" identified in each of 128 parent-affected child combinations in three different populations.

Calculation of Linkage Disequilibrium
To test whether a single allele is significantly more frequent on "Wilson disease chromosomes" than on normal chromosomes, standardized linkage disequilibrium coefficient (D/DMax) (8) and Yule's association coefficient (9) were calculated for each allege detected by each microsatellite marker. Significance of association for the allele showing the largest disequilibrium coefficient was evaluated using a one-sided chi-square test corrected for multiple testing by multiplying the corresponding p value by the number of alleles observed in the microsatellite marker.

Clinical Sample
The Sardinian cohort, drawn from 42 unrelated and non-consanguineous families, consisted of 158 individuals comprised of 57 WD patients, 62 parents and 39 unaffected siblings. The Russian cohort, drawn from 18 unrelated families, consisted of 66 individuals comprised of 24 WD patients, 36 parents and 6 unaffected siblings. In one family, where parents were first cousins, only one WD chromosome was included in the marker allege and haplotype analyses. The American cohort, drawn from 50 unrelated families, consisted of 125 individuals comprised of 50 WD patients, 70 parents, and 5 unaffected siblings. Two sets of parents were first cousins. Families in the American sample were from 13 states, Puerto Rico (three), Greece (one) and India (one). In 13 families, both parents were Jewish. The number of WD chromosomes analyzed (by at least one marker) from the Sardinian, Russian, and American cohorts were 82, 35, and 110 respectively. Five families from Sicily were analyzed including 6 parents and 5 WD patients. Diagnosis of Wilson's disease in the American families was based upon the criteria described by Scheinberg and Sternlieb (1).

Experimental Results

Wilson's disease (WD) is an autosomal recessive disorder of copper metabolism with an estimated worldwide carrier frequency of 1 in 90. Genetic linkage analysis has defined a 1–2 cM region at 13q14.3 which contains the disease locus. A novel rapid physical mapping strategy was used to construct complete YAC contigs and islands of cosmid contigs across the disease gene region. Development of microsatellite markers directly from cosmid clones identified physically ordered, highlypolymorphic markers at approximately 10-fold higher resolution than is possible by genetic analysis. The dense collection of markers were used to analyze 50 American, 42 Sardinian, 18 Russian, and 5 Sicilian Wilson's disease families. Linkage disequilibrium analysis identified a DNA marker interval very likely to harbor the disease locus and haplotype analysis indicates a high degree of allelic heterogeneity among WD cases. In the American families, a few predominant haplotypes account for roughly half of all WD chromosomes, the remaining haplotypes occur with relatively low frequency. In the more homogeneous Sardinian population, three haplotypes account for approximately 80% of WD chromosomes. The data indicate that approximately 50% of WD mutations will occur with very low frequency in the American and Russian populations. The physical mapping protocol described here is well-suited for the rapid generation of microsatellite markers at approximately 100 kb intervals across a genomic region defined by flanking DNA markers. Such dense microsatellite maps provide a powerful tool for genetic analysis of heritable loci.

Physical Mapping and Cloning of the WD Gene Region

A 4.3 kb insert from the WD flanking marker D13S31 (probe pCR1324) was used to screen the large insert, CEPH II YAC sublibrary (see Methods; 5). Clones 879F5 (1.3 Mb) and 859D12 (1.4 Mb) were identified (FIG. 1). A chromosome "walk" was performed using radiolabeled inter-Alu PCR product (10) from both YAC clones to re-screen the CEPH II library. Among the positive clones identified, YACs 805G10 (1.2 Mb) and 816D1 (1.6 Mb) contain homologous sequence to the distal WD flanking marker, D13S59 (data not shown). A higher resolution YAC map was constructed using inter-Alu PCR product from the 4 large YAC clones shown in FIG. 1 to screen the 1431 colony CEPH I YAC sublibrary (see Methods). A total of 16 mid-size YACs were identified, eight of which are shown in FIG. 1. The pattern of mid-size YACs detected by each large YAC clone was used to order the smaller YAC clones relative to one another. Inter-Alu PCR "fingerprinting" of YAC clones further assisted the ordering process (data not shown). The YAC clones have not been characterized for the presence of chimeric (non-CH13) DNA sequence because they were used to screen a flow-sorted, CH13 enriched cosmid library. This strategy rendered the chimeric DNA "invisible" because these segments are not represented in the CH13-specific cosmid library.

Inter-Alu PCR probes from all 8 midsize YACs were combined to screen a CH13-specific cosmid library (see Methods). 283 "positive" cosmids were identified. To align the cosmids into contigs, 283 high density filters were prepared each containing a full array of the 283 positive cosmids. Radiolabelled RNA end-probes were generated from each of the 283 cosmids using the T3 and T7 promoters flanking the cosmid inserts and the "RIBOPROBE" labeling system (Stratagene®) (5). In a single experiment, 283 end-probe preparations were hybridized to 283 high density filters. FIG. 2 illustrates the contig building procedure. Each cosmid that forms part of a contig identifies itself and its overlapping neighbors. Somewhat less than 20% of clones hybridized only to themselves, indicating either that they were false positives, or form contigs of one. The seven cosmid contigs identified by this method, and verified by subsequent tests (excluding contig 3), consisted of 5–44 cosmids and are estimated to span 100 to 600 kb each. An eighth cosmid contig was identified using a candidate cDNA clone for the WD gene (11). PCR primers from the clone amplified regions of YACs 220A9 and 27D8, but did not amplify cosmids from the 7 contigs. The 3.5 kb cDNA clone was used to screen the entire cosmid library. A total of 16 overlapping cosmids were identified (a minimum of 7 cosmids span contig 3, FIG. 1).

Mid-size YAC DNAs were separated by pulsed filed gel electrophoresis (12), extracted from agarose, partially purified with GENECLEAN (Bio 101, Inc.), and radiolabelled to hybridize against cosmid arrays from the 8 cosmid contigs (data not shown). The pattern of cosmid hybridization was used to order cosmid islands across the disease gene region. Fluorescent in situ hybridization of individual cosmid clones was used to eliminate several "questionable" smaller cosmid islands (13). At least one cosmid from each contig was chosen to isolate microsatellite DNA markers (7) and STS sequences. PCR amplification of cosmid and mid-size YAC clones with oligonucleotide primers from the DNA markers and STS sequences verified the physical order of cosmid contig islands (FIG. 1). Eight new microsatellite markers and One previously mapped marker, D13S133 (7), are spaced at estimated distances of 100–200 kb across the disease gene region.

Linkage Disequilibrium Analysis

A total of 15 Wilson's disease families representing diverse ethnic and geographical populations were genotyped with the nine microsatellite markers described above. In each family, the two chromosomes (haplotypes) inherited by an affected child constitute the "WD" chromosomes, and the remaining two chromosomes (haplotypes) constitute the "normal" chromosomes. Table I summarizes the distribution of DNA marker alleles in each of the three clinical samples (S=Sardinian; R=Russian; A=American). Significant LD to the disease locus was detected with 7 of 9 DNA markers in the relatively homogeneous Sardinian sample. In the more heterogeneous American sample, the strongest evidence of LD was detected at loci D13S295 and D13S296. This result is interesting because these loci flank a candidate gene for Wilson's disease (11) ("cDNA" in FIG. 1). A single base pair C→A transversion within the candidate gene was not detected in over 100 normal chromosomes and associates preferentially with the most common WD haplotype (aA/rA; see discussion below) in the Russian and American families (11). Marker D13S301, located to the same cosmid clone as the cDNA clone, detects significant LD only in the Sardinian families presumably because the "5" allele is the most common allele on both normal and WD chromosomes. Thus, LD data strongly suggests the WD gene resides between loci D13S295 and D13S296, possibly at the candidate gene locus.

TABLE I

| Locus D13 | Pop[1] | #Chrom[2] WD | N | Alleles Total | WD[3] | N[4] | D/Amax | /A/[5] | p[6] |
|---|---|---|---|---|---|---|---|---|---|
| S294 | S | 78 | 59 | 10 | 6 | 4 | 0.43 | 0.51 | NS |
|  | R | 31 | 32 | 9 | 6 | 9 | 1 | 1 | NS |
|  | A | 93 | 62 | 13 | 13 | 4/9 | 0.50 | 0.52 | NS |
| S295 | S | 76 | 58 | 5 | 3 | 1 | 0.23 | 0.25 | NS |
|  | R | 32 | 33 | 4 | 2 | 4 | 0.44 | 0.53 | NS |
|  | A | 99 | 70 | 7 | 2 | 4 | 0.84 | 0.87 | *** |
| WDC[7] | A | 26 | 102 | 2 | A | C | 1.0 | 1.0 | *** |
| S301 | S | 82 | 61 | 10 | 5 | 5 | 0.30 | 0.55 | * |
|  | R | 33 | 32 | 10 | 5 | 5 | 0.30 | 0.46 | NS |
|  | A | 99 | 72 | 12 | 5 | 5 | 0.20 | 0.33 | NS |
| S296 | S | 80 | 61 | 6 | 10 | 5 | 0.39 | 0.65 | *** |
|  | R | 35 | 35 | 7 | 9 | 5 | 0.85 | 0.89 | * |
|  | A | 99 | 73 | 9 | 9 | 10 | 0.87 | 0.83 | *** |
| S133 | S | 82 | 61 | 14 | 14 | 14 | 0.34 | 0.58 | * |
|  | R | 33 | 34 | 12 | 14 | 14 | 0.32 | 0.53 | NS |
|  | A | 96 | 69 | 14 | 14 | 14 | 0.26 | 0.47 | NS |
| S297 | S | 82 | 58 | 6 | 3 | 4 | 0.82 | 0.92 | *** |
|  | R | 33 | 34 | 4 | 4 | 4 | 0.07 | 0.10 | NS |
|  | A | 97 | 68 | 9 | 4 | 4 | 0.23 | 0.39 | NS |
| S298 | S | 78 | 58 | 8 | 3 | 3 | 0.31 | 0.53 | ** |
|  | R | 35 | 36 | 8 | 7 | 3 | 0.11 | 0.16 | NS |
|  | A | 101 | 71 | 10 | 3 | 7 | 0.39 | 0.56 | ** |
| S299 | S | 78 | 61 | 10 | 8 | 16 | 0.61 | 0.81 | *** |
|  | R | 35 | 36 | 10 | 16 | 16 | 0.15 | 0.26 | NS |
|  | A | 95 | 66 | 12 | 16 | 16 | 0.28 | 0.44 | NS |
| S300 | S | 78 | 59 | 9 | 8 | 3 | 0.81 | 0.69 | *** |
|  | R | 31 | 30 | 6 | 2 | 9 | 0.35 | 0.54 | NS |
|  | A | 97 | 70 | 12 | 2 | 3 | 0.40 | 0.47 | NS |

Table I
Evaluation of allelic allocation in Wilson's disease families
1) The populations listed are: S=Sardinian; R=Russian; and A=American. 2) Number of Wilson's (WD) and normal (N) chromosomes genotyped. 3) allele with the largest positive deviation between observed frequency and frequency expected under the hypothesis of no association (8). 4) allele with the highest frequency in normal chromosomes. 5) Yules association coefficient (9). 6) p values for chi-square test of association with Yate's correction for continuity and correction for number of alleles; *=p<0.01; =p<0.001; *=p<0.0001.7) Wilson's disease candidate gene.

Table II shows the common haplotypes in each of the three large clinical samples. In the Sardinian population, a single 7-marker haplotype (sA) was found in 26 chromosomes (36% of all WD chromosomes). Another 21 chromosomes differed from sA at a single marker locus. Overall, 47 WD chromosomes (65%) carried a six-marker "sA" haplotype as shown in Table II. The same 6-marker haplotype was never found in 57 unambiguously genotyped normal chromosomes, and only three normal chromosomes carried a 5-marker haplotype "sA". Assuming that the 2 bp differences in a single microsatellite marker are due to microsatellite instability (14), the strong association between WD and the 6-marker "sA" haplotype (chi-square=55.75, p<0.000001) suggests that all 6-marker "sA" haplotype WD chromosomes carry the same WD mutation. This mutation presumably derived from a single mutation event which occurred on the haplotype "sA" chromosome. In the Sardinian population, two remaining haplotypes (sB, sC) account for an additional 11 WD chromosomes. All other WD haplotypes differ from each other at two or more marker loci.

TABLE II

| Locus D13 | Sardinian | | | Russian | | | American | | | | | |
|---|---|---|---|---|---|---|---|---|---|---|---|---|
|  | sA | sB | sC | rA | rB | rC | aA | aB | aC | aD | aE | aF |
| S294 | — | — | — | — | — | — | — | — | — | — | — | — |
| S295 | — | — | — | 2 | 3 | 3 | 2 | 1 | 1 | 4 | 4 | 4 |
| S301 | 5 | 10 | 2 | 5 | 4 | 6 | 5 | 5 | 6 | 5 | 5 | 6 |
| S296 | 10 | 5 | 5 | 9 | 5 | 5 | 9 | 10 | 10 | 10 | 9 | 10 |
| S133 | 14 | 5 | 4 | 14 | 5 | — | 14 | 14 | 14 | 14 | 14 | 14 |
| S297 | 3 | 7 | 4 | 4 | 7 | 7 | 4 | 4 | 3 | 3 | 3 | 4 |
| S298 | 3 | 7 | 3 | 3 | 7 | 7 | 3 | 3 | 7 | 5 | 3 | 4 |
| S299 | 8 | 5 | 16 | — | — | — | — | — | — | — | — | — |
| S300 | 8 | 9 | 9 | — | — | — | — | — | — | — | — | — |
| WD (#) | 47 | 8 | 3 | 8 | 4 | 2 | 22 | 5 | 3 | 4 | 2 | 2 |
| (%) | (65) | | | (26) | | | (29) | | | | | |
| N (#) | 0 | 2 | 2 | 1 | 2 | 0 | 0 | 3 | 1 | 0 | 2 | 0 |
|  | 81% | | | 52% | | | 50% | | | | | |

Table II

Common haplotypes detected in the Sardinian, Russian, and American samples. Total haplotypes for each column indicate all WD chromosomes from that clinical sample which match the haplotype exactly, or which differ by one marker genotype due to unknown phase, untyped marker, or 2 bp difference at one marker locus. Percent of total chromosomes indicates the percent of WD chromosomes in a particular clinical sample (Sardinian, Russian, or American). Markers which show no genotype were relatively more divergent from the other loci in that population, presumably reflecting historical recombination.

The predominant haplotype identified among the American and Russian samples was identical. In the American sample, 22 WD chromosomes had a 5-marker haplotype matching the 6-marker haplotype "aA". Haplotypes aB and aC differ from aA at two marker loci. An additional 8 WD chromosomes contain a subset of 5-marker haplotypes which match these 6-marker haplotypes. An additional 9.4% of all WD chromosomes from the American sample had a 5 or 6-marker haplotype matching aD, aE, or aF. The most common haplotypes in the American sample account for approximately 50% of WD mutations. The remaining chromosomes in the American sample, as well as the Russian and Sicilian (not shown) sample, display very divergent haplotypes.

Experimental Discussion

A rapid physical mapping scheme was used to generate a dense collection of physically mapped microsatellite markers across the genetically defined Wilson's disease region. The method relies upon inter-Alu PCR amplification to selectively amplify human DNA from monochromosomal cell hybrids. The PCR product is then used to screen genomic YAC libraries for chromosome-specific clones (5, 15). Next, the method is used to amplify overlapping YAC clones (including chimeras) to screen cell-sorted, chromosome specific cosmid libraries. Individual "islands" of cosmid contigs are ordered by their pattern of hybridization to overlapping YAC clones and by STS mapping. This scheme circumvents the time consuming characterization of chimeric YAC clones and minimizes individual "walk" steps. The protocol constructs microsatellite marker maps at approximately 10-fold greater resolution than is possible by conventional genetic linkage analysis.

The utility of a high resolution microsatellite marker map is demonstrated by the analysis of 115 Wilson's disease families. In the Sardinia population, the disease locus is in significant LD with most markers spanning the genetically defined region, suggesting a possible Founder effect. In the more heterogeneous American families, the most significant LD is detected by marker loci D13S295 and D13S296.

A cDNA clone localized to a cosmid contig bracketed by these two markers provides strong evidence for LD. Amino acid homology and structural predictions indicate the cDNA encodes a copper-transporting ATPase with strong homology to the gene for Menkes disease (Mc1) (16), another copper metabolism disorder in humans. The C→A transversion alters a highly conserved histidine residue at the transduction domain and is a presumptive causal mutation. This evidence strongly suggests the cDNA clone (pWD) is the WD gene (11).

Haplotype analysis of the WD families from three disparate populations is likewise revealing. The most common haplotype in the American families detects 29% of all WD chromosomes. The CA transversion detected by the WD candidate gene is detected only on the aA/rA haplotype (11), supporting the assumption that the various WD haplotypes reflect independent disease mutations. This data indicates that approximately half of all WD mutations in the ethnically diverse American population (as well as the Russian population) will be rare, although there are examples of identical cystic fibrosis mutations on chromosomes with different haplotypes, and vice versa (17). A single haplotype accounts for approximately 65% of all WD chromosomes in Sardinia, but approximately 20% of mutations will predictably be rare even in this relatively homogeneous population. To the extent that these genetic haplotypes correlate with individual mutational events which cause Wilson's disease, this analysis provides a qualitative estimate of allelic heterogeneity of this disorder. The haplotype analysis presented in this study indicates that molecular diagnosis of Wilson's disease will be complicated, as is the current situation with cystic fibrosis (18).

References of the First Series of Experiments and the Preceding Sections

1. Scheinberg, I. H., and Sternlieb, I., (1984) Wilson's disease. Volume XXIII; Major Problems in Internal Medicine. W D Saunders Co. Lloyd H. Smith, Jr., ed.
2. Frydman, M., Bonne-Tamir, B., Farrer, L. A., et al. (1985). Proc. Natl. Acad. Sci. U.S.A., 82:1819–1821.
3. Farrer, L. A., Bowcock, A. M., Hebert, J. M., et al. (1991), Neurology, 41:992–999.
4. Albertsen, H. M., Abderrahim, H., Cann, H. M., Dausset, J., LePaslier, D., and D. Cohen. (1990), Proc. Natl. Acad. Sci. U.S.A., 87:4256–4260.
5. Fischer, S. G., Cayanis, E., Russo, J., Sunjevaric, I., Boukhgalter, B., Li, X-L., Zhang, P., Rothstein, R., Yu, M-T., Warburton, D., Edelman, I. S., and A. Efstratiadis. Assembly of ordered contigs from YAC-selected cosmids of human chromosome 13. Submitted.
6. Zhang, P., Schon, E. A., Fischer, S. C., Cayanis, E., Weiss, T., Kitler, S., and Bourne, P. E., submitted.
7. Petrukhin, K. E., Speer, M. C., Cayanis, E., Bonaldo, M. F., Tantravahi, U., Soares, M. B., Fischer, S. G., Warburton, D., Gilliam, T. C., and Ott, J. (1993) Genomics, 15:76–85.
8. Chakravarti, A., Buetow, K. H., Antonarakis, S. E., Waber, P. G., Boehm, C. D., and Kazazian, H. H., (1984), Am. J. Hum. Genet., 36:1239–1258.
9. Kerem, B., Rommens, J. M., Buchanan, J. A., Markiewicz, D., Cox, T. K., Chakravarti, A., Buchwald, M., and Tsui, L. C., (1989), Science, 245:1073–1080.
10. Nelson, D. L., Ledbetter, S. A., Corbo, L., Victoria, M. F., Ramirez-Solis, R., Webster, T. D., Ledbetter, D. H., and Caskey, C. T. (1989), Proc. Natl. Acad. Sci. U.S.A., 86:6686–6690.
11. Tanzi, R. E., Petrukhin, K., Chernov, I., Pellequer, J. L., Wasco, W., Ross, B., Romano, D., Brzustowicz, L. M., Devoto, M., Peppercorn, J., Bush, A., Sternlieb, I., Pirastu, M., St. George-Hyslop, P. H., Gusella, J. F., Evgrafov, O., Honig, B., Penchaszadeh, G. K., Edelman, I. S., Soares, M. B., Scheinberg, I. H., and T. C. Gilliam, submitted.
12. Schwartz, D., and Cantor, C. (1984), Cell, 37:67–75.
13. Warburton, D., Yu, M. T., Tantravahi, U., Lee, C., Cayanis, E., Russo, J., Fischer, S. (1993), Genomics, 16:355–360.
14. Weber, J. L. and Wong, C., (1993), Hum. Mol. Genet., 2:1123–1128.
15. Chumakov, I., Rigault, P., Guillou, S., et al. (1992), Nature, 359:380–387.

16. Vulpe, C., Levinson, B., Whitney, S., Packman, S., and Gitschier, J. (1993) Nature Genetics, 3:7–13.
17. Morral, N., Nunes, V., Casals, T., Chillon, M., Gimenez, J., Bertranpetit, J., and Estivill, X., (1993), Hum. Mol. Genet., 2:1015–1022.
18. Fujimura, F. K., (1991), Clin. Biochem., 24:353–361.
19. Orita, M., Iwahana, H. Kanazawa, H., Hayashi, K. & Sekiya, T. (1989) Proc. Natl. Acad. Sci. USA, 86, 2766–2770.
20. Orita, M., Suzuki, Y., Sekiya, T. & Hayashi, K. (1989) Genomics 5, 874–879.
21. Saiki, R. K., Gelfand, D. H., Stoffel, S., Scharf, S. J., Higuchi, R., Horn, G. T., Mullis, K. B. & Erlich, H. A. (1988) Science 239, 487–491.
22. Demers, D. B., Odelberg, S. J. & Fischer, L. M. (1990) Nucleic Acids Res. 18, 5575.
23. Dean, M., White, M. B., Amos, J., Gerrard, B., Stewart, C., Khaw, K. T. & Leppart, M. (1990) Cell 61, 863–870.
24. Ainsworth, P. J., Surh, L. C. & Coulter-Mackie, M. B. Nucleic Acids Res. 19, 405–406.
25. Suzuki, Y., Orita, M., Shiraishi, M., Hayashi, K. and Sekiya, T. (1990) Ocogene 5, 1037–1053.
26. Cawthon, R. M., Weiss, R., Xu, G., Viskochil, D., Culver, M., Stevens, J., Robertson, M., Dunn, D., Gesteland, R., O'Connell, P. & White, R. (1990) Cell 62, 193–201.

Second Series of Experiments

Wilson's disease (WD) is an autosomal recessive disorder characterized by the toxic accumulation of copper in a number of organs, particularly the liver and brain. Genetic linkage studies have mapped the disease gene to 13q14.3. A partial cDNA clone (pWD) is described which maps to this region. Sequence analysis indicates the candidate gene is a copper-transporting ATPase with 62% amino acid identity to Mc1, the gene responsible for the X-linked copper metabolism disorder, Menkes disease. The predicted functional properties of the pWD gene together with its strong homology to Mc1, genetic mapping data, and population genetic evidence for identification of a disease-specific mutation, strongly imply that pWD is the Wilson's disease gene.

Wilson's disease (WD) is an autosomal recessive disorder of copper metabolism with a world-wide prevalence of 30 per million and a corresponding carrier frequency of 1 in 90. Biochemically, it is characterized by abnormally high concentrations of copper particularly in the liver and brain, and deficiency of the plasma copper-protein, ceruloplasmin. Affected individuals initially accumulate vast increases in hepatic copper-leading to the development of acute or chronic liver disease. Cooper subsequently also deposits in the brain, where it causes profound psychiatric and neurological symptoms that are the direct consequences of copper's toxicity. The disease is always fatal if untreated but pharmacologic removal of the excess copper can be dramatically effective therapy for patients with hepatic or cerebral symptomatology (1). X-linked Menkes' disease is likewise a lethal disorder of copper metabolism (2), but one in which deficiency of copper appears to be the fundamental cause of diverse clinical abnormalities resulting from the reduced activity of essential copper-dependent proteins. The principal pathology of both Wilson's disease and Menkes' disease appears to be a defective copper transport mechanism. Recently, several X-chromosome translocations associates with Menkes' disease were characterized to reveal the apparent disruption of a copper-transporting ATPase (Mc1) (3). The Mc1 gene is the first reported eukaryotic copper-transporter molecule and a convincing candidate for the Menkes' disease gene.

In 1985, genetic linkage studies showed that the Wilson's disease locus segregates with the red cell enzyme esterase-D (ESD) on chromosome 13 (4), and subsequent studies refined the disease locus considerably (5). Recently, the disease region was cloned, microsatellite markers were identified and ordered across the locus, and haplotype and linkage disequilibrium analysis was performed on 115 Wilson's disease families. A novel cDNA clone was mapped to the genetic interval demonstrating the strongest disequilibrium to the WD locus (6). We now report the characterization of this cDNA clone and of an associated mutation in Wilson's disease patients. We propose that pWD encodes the normal protein that prevents development of Wilson's disease.

Isolation of cDNA Clones

The 3.5 kb pWD02 cDNA clone was identified by hybridization of an oligo(dT)-primed brain cDNA library with a degenerate oligonucleotide to a novel heavy metal binding site situated on the A-β protein of the amyloid β-protein precursor (7). Preliminary evidence indicated that this clone mapped to chromosome 13q14 (unpublished observation) and DNA sequence of a 500 bp subclone revealed strong amino acid sequence homology to Mc1, the putative Menkes' disease gene (3). The cDNA clone was physically mapped to the genetically defined WD gene region (6). These data strongly implicated pWD02 as a candidate for the WD gene.

Figure 3:
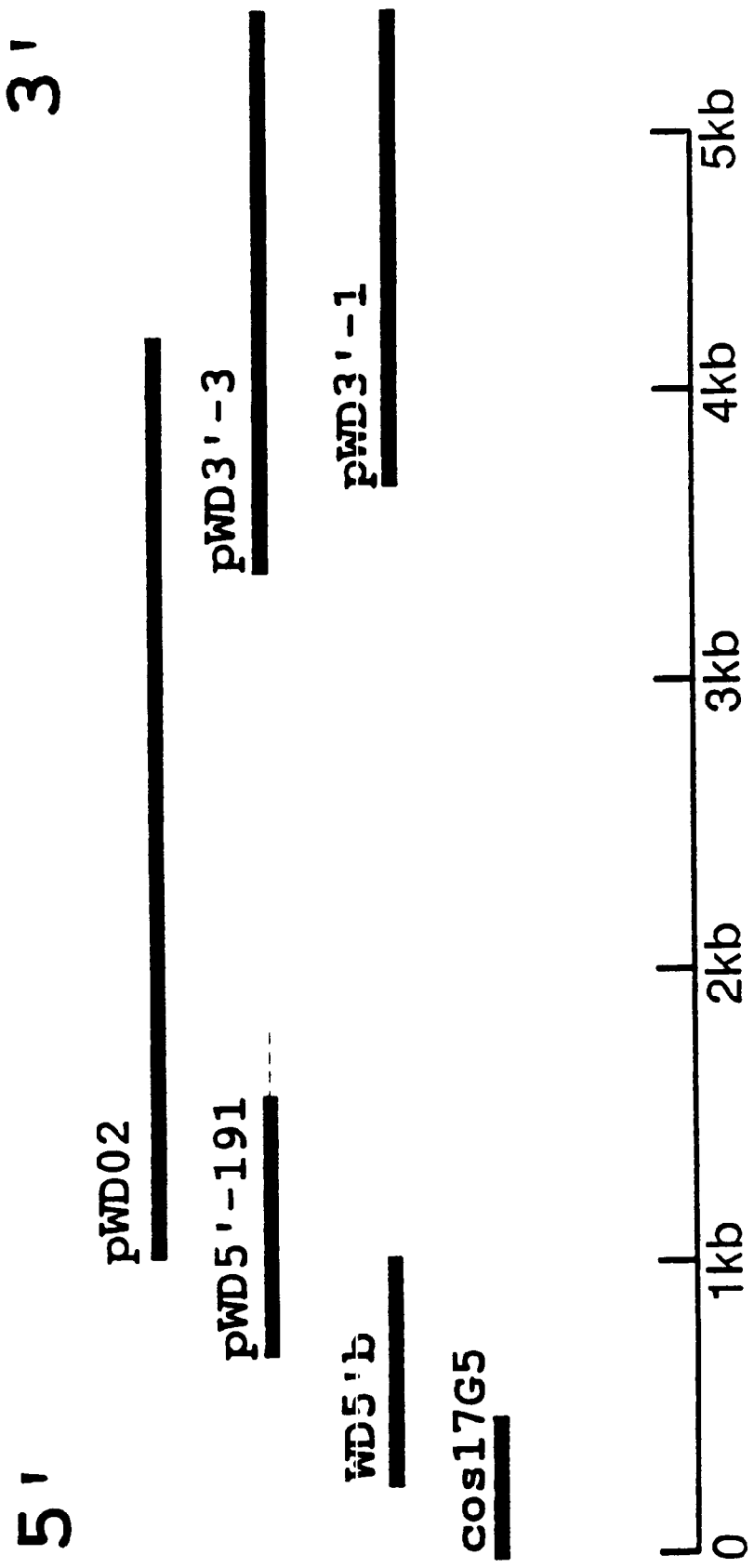
FIG. 3 Extension of the pWD02 cDNA clone. See text and (9 of the second series of experiments).

Clone pWD02 contained 3477 bp of DNA which was subsequently shown to include 2491 bp of coding sequence and 985 bp of 3' untranslated RNA. An oligonucleotide was synthesized from the 3'-most end of pWD02 and used to screen a "normalized" brain cDNA library (8). A 2.1 kb cDNA clone, pWD3'-3 and a 1.5 kb clone, pWD3'-1 were identified (FIG. 3). Both clones contained two AATAAA (SEQ ID NO: 19) polyadenylation consensus sites and poly A tracts. Additional sequence at the 5'-end of the pWD gene was identified by screening 5 cDNA libraries (9) in conjunction with genomic DNA sequencing from homologous cosmid clones. FIG. 1 illustrates the 5' extension of the clone through identification of 197 bp of new sequence from pWD5'-191, 520 base pairs from the PCR amplification product WD5'b, and 243 base pairs from a homologous cosmid clone (17G5). The 5'-terminus of the gene has not yet been identified. In total, 5422 base pairs of the pWD gene have been cloned which encode 1110 amino acids and 2042 base pairs of 3' untranslated region (10).

Expression of the pWD Gene

Figure 4:
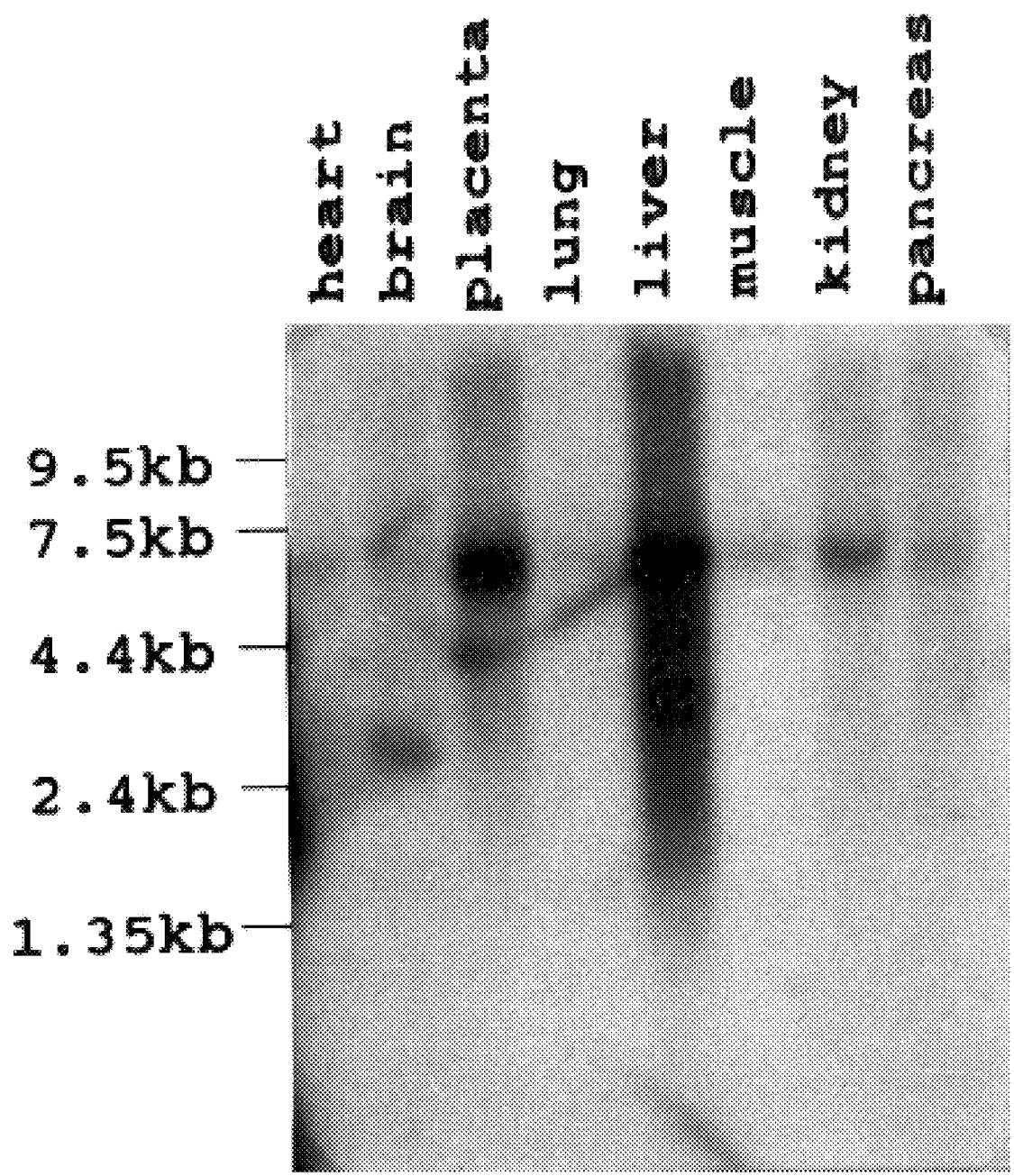
FIG. 4 Northern blot analysis of pWD02 cDNA clone. The Northern blot was purchased from Clonetech and hybridized with radiolabeled pWD02 DNA probe. Poly(a)+ RNA from various tissues is indicated at the top of each well.

Hybridization of clone pWD02 to a Northern blot (Clontech) containing polyA+ RNA showed expression of the WD gene in all tissues where it was tested, including heart, brain, placenta, lung, liver, skeletal muscle, kidney and pancreas. Expression was most pronounced in the liver and placenta (FIG. 4). The transcript size is estimated as approximately 5.9 kb. To date, applicants have not been successful in isolating intact RNA for Northern blot analysis from WD liver transplant samples or from WD liver biopsies. Applicants have, however, detected pWD gene expression by reverse transcriptase PCR of both WD liver biopsy RNA and WD lymphoblast RNA (data not shown).

Sequence Analysis of pWD

Both strands of the pWD cDNA were sequenced in at least 2 cDNA clones, and for much of the gene, multiple cDNA clones and/or genomic DNA was sequenced (11). One open reading frame of 3330 bp encoding 1110 amino acids is shown in FIG. 5. Two poly A consensus motifs (AATAAA) (SEQ ID NO: 19) are detected (4903–4908, 5392–5397), and a poly A tract is shown at the 3' terminus. The 5' terminus is not yet cloned as indicated by the open reading frame continuing to the first codon and the absence of an initiation codon and consensus sequence. The partial cDNA spans approximately 80 kb of genomic DNA (data not shown). Preliminary data indicates a total of 19 intron/exon junctions.

Searches of protein databases (12) revealed a strong homology with the ATPase family including the Mc1 protein (Menkes disease) (3), Enterococcus hirae Cu++ exporting ATPase (13) and prokaryotic cadmium transporter (14). The pWD protein has a metal binding site domain and three cytoplasmic ATPase domains (ATP binding domain, phosphorylation domain, and phosphatase domain). The last three domains are characteristic of P-type, or transducing, ATPases (15, 16). In addition to ATPase cytoplasmic domains, pWD appears to have a number of transmembrane helices. The presence of all these features suggest that the pWD protein is a metal transporting ATPase.

Metal Binding Site (1–481)

Figure 7:
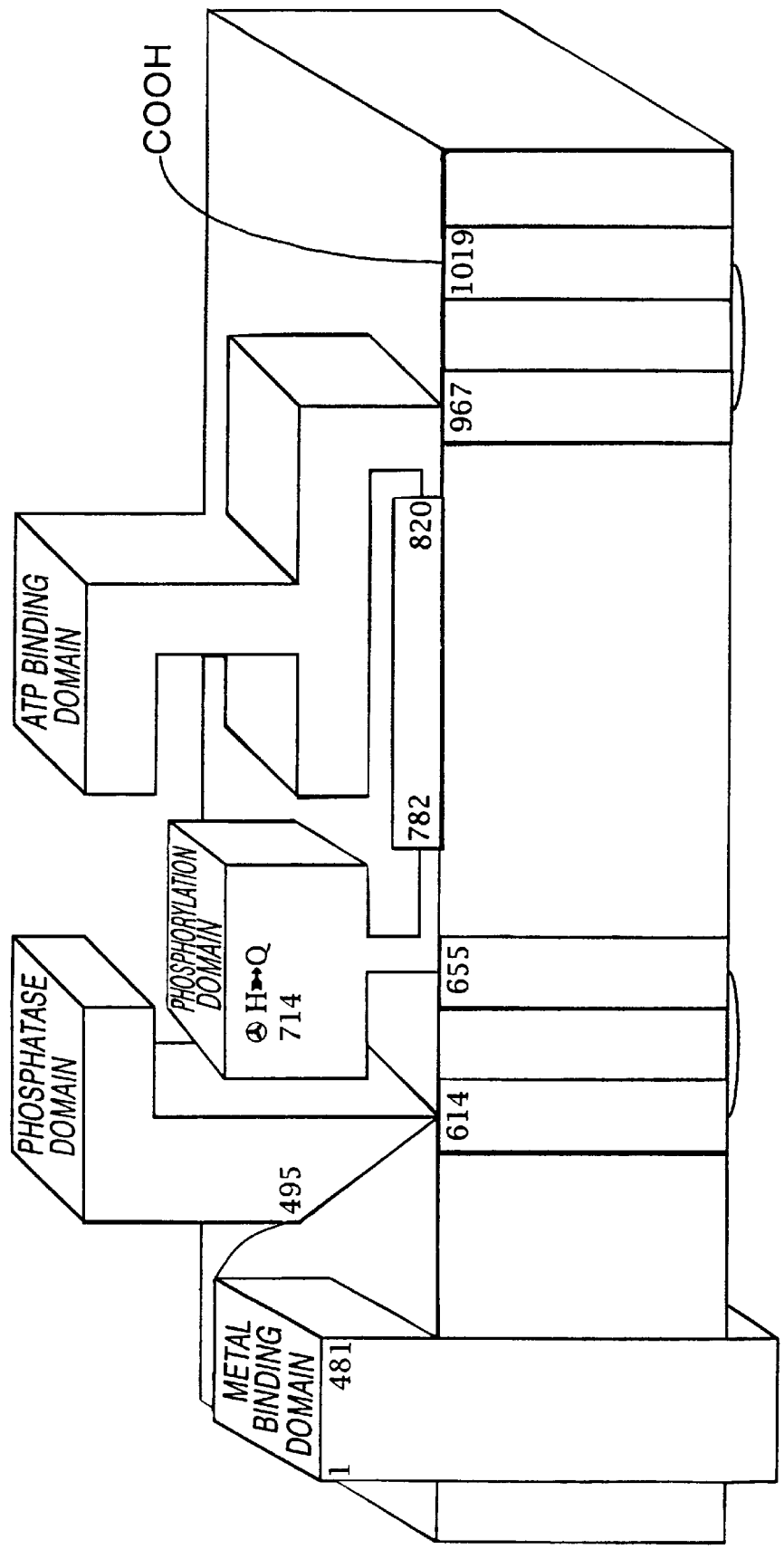
FIG. 7 Model of the architecture of the pWD protein. The model is based upon the observed consensus sequences (multi-alignment) and on the secondary structure predictions (18 of the second series of experiments). There are four transmembrane helices (see text). The rest of the molecule is intracellular since typical intracellular domains have been predicted (ATP binding site, phosphorylation site, etc.) except for a potential metal binding transmembrane domain. This model represents the expected interaction between the nucleotide binding domain, phosphorylation site and phosphatase/transduction domain.
Figure 8A:
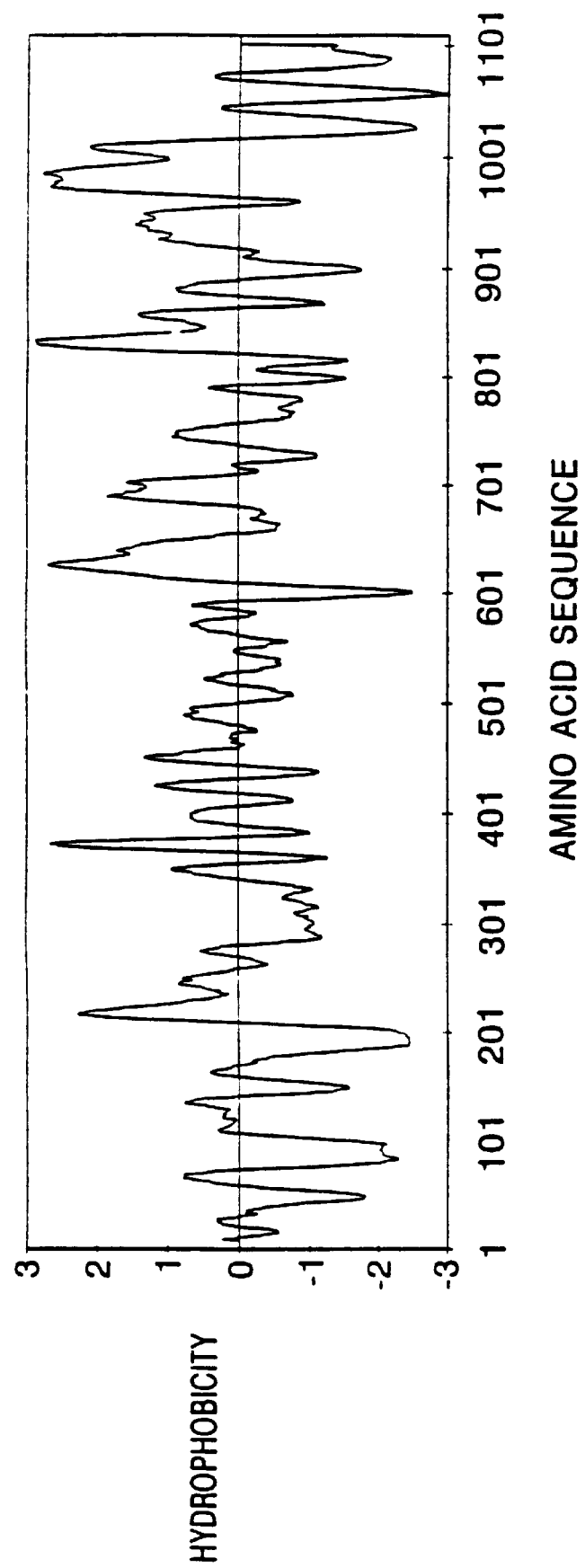
FIG. 8 Hydrophobicity and charge profiles of pWD. (A) Kyle and Doolittle hydrophobicity plot, and (b) Profile of positive and negative charges (see 18 of the second series of experiments).
Figure 8B:
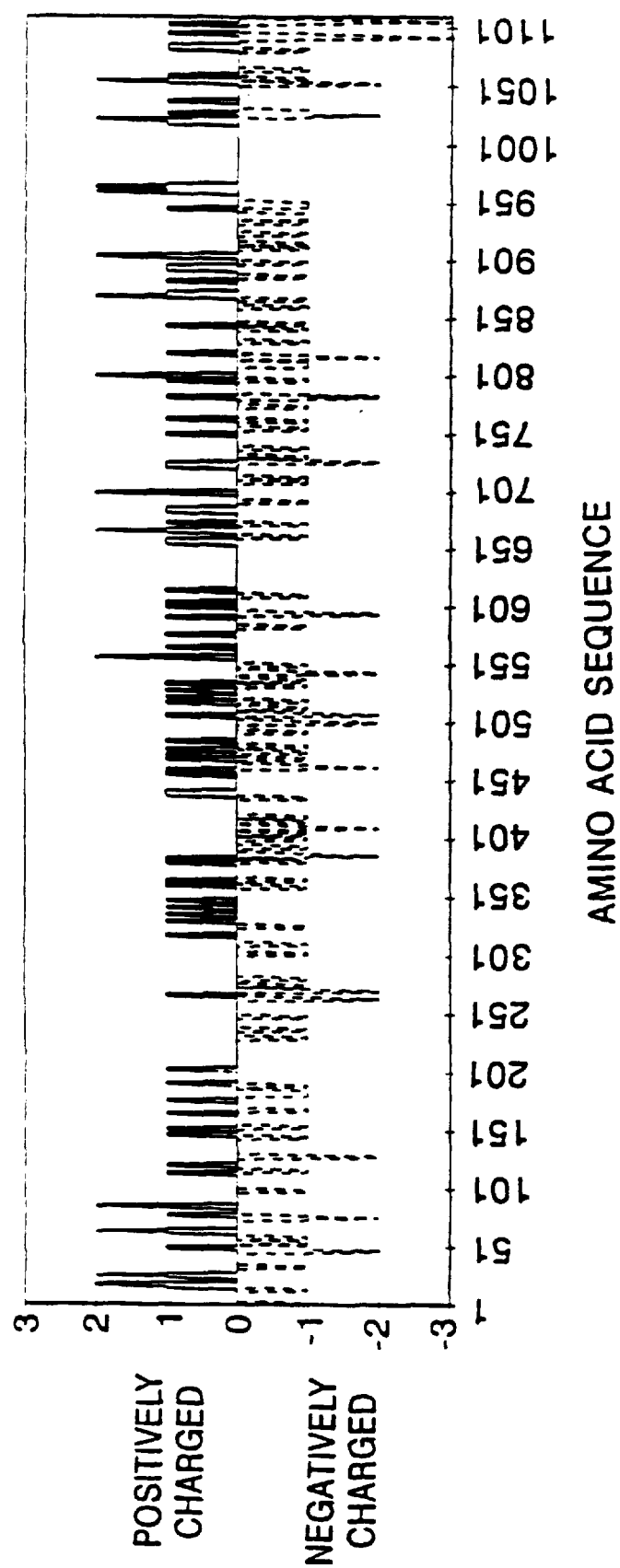

There are five metal binding regions, each about 50 residues long which contain a GXXCXXC (SEQ ID No. 20) motif (FIGS. 6, 7). This motif has been found in other proteins that bind or transport metals (13, 16). The five regions are highly homologous, however, the sequences connecting them are quite different. The presence of five metal binding sites in pWD and six in Mc1 is in contrast to the presence of one or two such motifs in other published sequences (17). FIG. 8A presents the hydrophobicity profile of pWD and FIG. 8B contains a profile of positive charges and few negative charges. There is a hydrophobic peak around the third metal binding site (210–258) which corresponds to a region of no positive charges and few negative charges. Moreover, there are a number of portable extracellular N-glycosylation sites between the first, second, third, and fourth metal binding sits (96–99, 146–149, 290–293). This evidence suggests that the metal binding domain contains transmembrane regions and may be the location of cation transport.

Phosphorylation Domain (656–782)

This domain contains an invariant aspartic acid and DKTGTIT (SEQ ID No. 35) sequence found in P-type ATPases (FIG. 6). In pWD, Ile is replaced by Leu. In calcium ATPase the conserved aspartic aid residue is believed to be phosphorylated as an integral part of the cation transport cycle. The ATP driven reaction to form phosphoenzyme at this site is central to the mechanism of energy transduction by ATPases. This domain contains the mutated amino acid found in a significant proportion of the Wilson's disease patients.

ATP Binding Domain (820–967)

This domain extends between the putative 4th and 5th transmembrane helices. It contains a lysine (820) followed by a glycine which may be related to an FITC binding lysine in other ATPases (16). The domain ends with a hinge region containing the consensus sequence GDGXNDXPL (SEQ ID No. 21) (FIG. 6; 16). Secondary structure prediction algorithms (18) assign a repeating (αβ) motif (19) which is found in ATP binding domains in proteins whose three dimensional structure is known (20).

Transmembrane Segments

Five hydrophobic segments can be clearly identified in the pWD sequence. Of these, two (614–655, 967–1019) correspond to regions with no positive and negative charges. Based on their length, each is assumed to contain a pair of transmembrane helices. The first transmembrane helix contains a cation binding site composed of two cysteines flanking a proline residue. This conserved proline may be involved in the transduction process in $Ca^{++}$ ATPases (21).

The peaks (823–864, 920–958) are unlikely to be transmembrane because they fall in the cytoplasmic ATPase domain. The peak (681–710) is not assigned to a transmembrane helix because it is not long enough to go through the membrane twice. Applicants have excluded the possibility that the peaks at (614–655) and (681–710) constitute a transmembrane pair because the phosphorylation site at 672 must be cytoplasmic. Based on hydrophobic moment calculation (22), applicants can identify a long amphophilic helix (782–820) but it is unclear whether it is a transmembrane helix.

The single most striking feature of the pWD protein is a 62% identity and 76% amino acid homology with the Mc1 protein of Menkes disease. The overall design of the two proteins is likewise strikingly similar, each with the requisite transducing ATPase moieties and multiple copper binding sites.

Applicants' sequence analysis has revealed remarkable structural similarities in two genes each of which prevents a unique lethal disorder of copper transport. The pWD protein appears to differ from the Mc1 protein in several ways. First, there are four segments of the Mc1 gene which are missing in the pWD gene in addition to 6 short segments which are unique to the pWD gene (FIG. 5). The largest missing segment corresponds to the fourth transmembrane helix in Mc1 and another deletion to the fifth transmembrane helix. These deletions imply a different pattern in the transmembrane segments between the two proteins. In the Menkes protein, there is a potential extracellular region between two consecutive transmembrane helices (including basic residues) whereas the sequences between transmembrane helices in the pWD protein are quite short and have no predicted extracellular region. In addition, no stalk is detected in the pWD protein, unlike the Mc1 protein. Moreover, in the Mc1 protein, eleven Asn-glycosylation sites are predicted by the program MOTIFS (23) in contrast to four in the pWD protein.

The pWD protein has five predicted metal binding sites as compared to six in Mc1. There may be a sixth site at the 5'-terminus of the pWD gene which is not yet cloned. In contrast to the suggestion made for the Menkes protein (3) applicants have postulated that the metal binding domain for both pWD and Mc1 contain a transmembrane region, which may be involved in the energy-linked translocation of copper.

Detection of a Disease-Specific Mutation

Applicants have shown that the most common "WD haplotype" (25% of all WD chromosomes) in the Russian and U.S. samples occurs in only ~2% of "normal" chromosomes (6). An individual homozygous for this haplotype was DNA sequenced (24) and compared to the sequence generated from the pWD cDNA clones. A CA transversation (2142) was detected which changes a histidine residue to glutamine (FIGS. 6, 9) (25). DNA sequence was determined for both strands across this region in 8 WD families (6 American and 2 Russian) where one or two affected children were homozygous for the common haplotype. In all 8 families, both parents were shown to be heterozygous C/A, while all 9 affected children were homozygous A/A (data not shown). Table I shows the microsatellite marker haplotypes at nine loci spanning the Wilson's disease locus (26). The aA haplotypes displayed in Table I are minor variations of the pattern (- - 2 5 9 14 4 3 - -) as described (6). Applicants have shown that WD chromosomes bearing the closely related aB (- - 1 5 10 14 4 3 - -) haplotype (6) encode the normal histidine residue, as do all other WD and normal haplotypes tested (data not shown). In all, 22 of 22 WD chromosomes bearing the most common WD haplotype carry the $A^{2142}$ residue. Only 2 of 109 normal chromosomes identified from the Wilson's disease families display this haplotype (6). These two individuals and their parents were sequences to reveal a $C^{2142}$ as shown in Table I. In addition, 100 presumptive normal (not haplotyped) chromosomes were DNA sequenced from unrelated individuals (non-Wilson's disease families) and all encoded the normal $C^{2142}$ residue. Thus, the C→A transversion appears to be a disease-specific mutation as opposed to a tightly associated polymorphism.

Heavy metal ion-transporting ATPases are characterized by a conserved CPC sequence located 41 amino acids downstream of the DKTG phosphorylation site. These sequences may play a role in cation binding and transport across the membrane (27). The histidine to glutamine transversion at his714 residues 39 amino acids C-terminal to the DKTG phosphorylation domain. The histidine and adjacent proline residues are highly conserved among heavy metal-transporting ATPases (FIGS. 6, 9) suggesting that disruption of the histidine residue would be critical to the ability of the protein to transfer copper ions across the membrane into the luminal space. It is proposed that mutational replacement of the highly conserved histidine residue with glutamine accounts for illness from copper toxicity in 25%–30% of WD patients from the U.S. and Russian clinical samples. It is further proposed that the S/X/H/P.L-I/G-A/X/A/I motif is essential to ATPase function as indicated by the pWD mutation.

Several lines of evidence make it very likely that pWD is the gene responsible for Wilson's disease: (i) the gene maps to the genetically defined disease gene region and demonstrates strong linkage disequilibrium with the disease phenotype (6); (ii) the derived amino acid sequence predicts a protein with copper-transporting ATPase activity. Loss of this function is consistent with the disease phenotype; (iii) the derived amino acid sequence is 62% identical and 76% homologous to the Menkes disease gene, Mc1. Much evidence suggests that both Menkes disease and Wilson's disease result from improper cellular transport of copper; (iv) a CA transversion at position 2142 disrupts a highly conserved histidine residue believed to be involved in cation-coordination and transport across the membrane. The transversion appears to be disease-specific; and (v) the pWD transcript is heavily expressed in liver tissue.

The similarities between the two most prominent disorders of copper metabolism in humans has led several investigators to speculate that the disorders will share a common molecular basis. Most recently, the discovery of a putative copper-transporting ATPase as the protein which mutates to cause Menkes disease prompted investigators to predict that Wilson's disease would result from mutation of a similar protein (3). The accuracy of this prediction would seem to be borne out by the structure and predicted function of pWD. The differences in the pWD and Mc1 proteins may reflect the opposite life-preserving role each plays in the metabolism of copper. Mc1 appears to regulate the distribution of dietary copper to sites of copper-dependent protein synthesis. Several investigators have suggested that Mc1 acts principally at the basal-lateral surface of intestinal mucosal cells where its role is to transport dietary copper into the blood stream. Since pWD has all the characteristics of a copper transporting ATPase, it seems reasonable that the protein may reside on the apical pole of hepatocytes and functions to export excess copper from the liver via the bile canaliculi. Although compatible with the structure and predicted function of pWD, this mechanism leaves unexplained the significance of the deficiency of ceruloplasmin, which is seen in 95% of patients with Wilson's disease (27).

TABLE III

|     | Locus D13S | | | | | | | | | Disease | |
|     | 294 | 295 | 301 | 296 | 133 | 297 | 298 | 299 | 300 | Status | Genotype |
|---|---|---|---|---|---|---|---|---|---|---|---|
| aA | 13 | 2 | 5 | 9 | 14 | 4 | 3 | 16 | 2 | aWD | A |
|    | 13 | 2 | 5 | 9 | 14 | 4 | 3 | 16 | 3 | aWD | A |
|    | 4  | 2 | 5 | 9 | 14 | 4 | 3 | 16 | 2 | aWD | A |
|    | 3  | 2 | 5 | 9 | 14 | 4 | 3 | 16 | 3 | aWD | A |
|    | 13 | 2 | 5 | 8 | 14 | 4 | 3 | 16 | 2 | aWD | A |
|    | 13 | 2 | 5 | 9 | 14 | 4 | 3 | 16 | 2 | aWD | A |
|    | 4/5 | 2 | 5 | 9 | 14 | 4 | 3 | 16 | 2 | aWD | A |
|    | 13 | 2 | 5 | 9 | 14 | 4 | 3 | 16 | 2 | aWD | A |
|    | 13 | 2 | 5 | 9 | 14 | 4 | 3 | 16 | 2/3 | aWD | A |
|    | 6 | 2 | 5 | 9 | 14 | 4 | — | 16 | 2 | aWD | A |
|    | 4 | 1/2 | 5 | 9 | 14 | 4 | 3 | 16 | 2 | aWD | A |
|    | 7 | 2 | 5 | 9 | 14 | 4 | 3 | 16 | 2 | rWD | A |
|    | 4 | 2 | 5 | 9 | 13 | 4 | 3 | 16 | 2 | aWD | A |
|    | 13 | 2 | 10 | 9 | 14 | 4 | 3 | 16 | 2 | aWD | A |
|    | 13 | 2 | 5 | 9 | 3/14 | 4 | 1 | 16 | 2/3 | aWD | A |
|    | — | 1 | 5 | — | 14 | 4 | 3 | — | — | aWD | A |
|    | 4 | 1 | 5 | 9 | 14 | 4 | 3 | 16 | 2 | rWD | A |
|    | 4 | 1 | 5 | 9 | 14 | 4 | 3 | 16 | 2 | rWD | A |
|    | 6 | 1 | 5 | 9 | 14 | 4 | 3 | 16 | 2 | rWD | A |
|    | — | 3 | 5 | 9 | 14 | 4 | 3 | — | 2 | aWD | A |
|    | 4/5 | 3 | 5 | 9 | 14 | 4 | 3 | 16 | 2 | aWD | A |
|    | 4 | 3 | 5 | 9 | 14 | 4 | 3 | 16 | 2 | rWD | A |
|    | 4 | 3 | 5 | 9 | 14 | 1 | 4 | 16 | 3 | aN | C |
|    | 6 | 4 | 5 | 9 | 14 | 4 | 3 | 16 | 2 | aN | C |
| aB | — | — | 5 | 10 | 14 | 4 | 3 | 16 | 1 | aWD | C |
|    | — | — | 6 | 10 | 14 | 4 | 3 | 16 | 9 | aWD | C |
|    | 6 | 1 | 6 | 10 | 14 | 4 | 3 | 16 | 9 | aWD | C |
|    | 4 | 1 | 5/6 | 10 | 14 | 4 | 3 | 7 | 2 | aWD | C |
| aC | 11 | 1 | 7 | 10 | 14 | 3 | 7 | 4 | 3 | aWD | C |

Table III

Correlation of haplotypes with the putative disease-specific mutation. Genotypes are shown for each of 9 microsatellite markers spanning the WD gene region (6). The WD candidate gene maps between loci D13S295 and D13S296, on the same cosmid clone as locus D13S301 (26). "aWD" refers to affected individuals from the American sample, and "rWD" to affected individuals from the Russian sample.

References and Notes of the Second Series of Experiments

1. Scheinberg, I. H. and Sternlieb, I., (1984) Wilson's Disease. Volume XXIII; Major Problems in Internal Medicine, W. B. Saunders Co., Lloyd H. Smith, Jr., ed.
2. Menkes, J. H., Alter, M., Steigleder, G. K., Weakley, D. R. and Sung, J. H., (1962), Pediatrics, 29:764–779.
3. Vulpe, C., Levinson, B., Whitney, S., Packman, S. and Gitschier, J., (1993), Nature Genetics, 3:7, Chelly, J., et al., ibid, 3:14, Mercer, J. F. B., et al., ibid 3:20.
4. Frydman, M., Bonne-Tamir, B., Farrer, L. A., et al., (1985) Proc. Natl. Acad. Sci. U.S.A., 82:1819.
5. Bonne-Tamir, B., Farrer, L. A., Frydman, M., Kannaane, L. H., (1986) Genet. Epidemiol., 3:201; Bowcock, A. M., Farrer, L. A., Cavalli-Sforza, L. L., et al., (1987), 41:27; Farrer, L. A., Bowcock, A. M. and Herbert, J. M., et al. (1991).
6. Petrukhin, K., Fischer, S. G., Pirastu, M., Tanzi, R. E., Chernov, I., Devoto, M., Brzustowicz, L. M., Cayanis, E., Vitale, E., Russo, J. J., Matseoane, D., Boukhgalter, B., Wasco, W., Figus, A. L., Loudianos, J., Cao, A., Sternlieb, I., Evgrafov, O., Parano, E., Pavone, L., Warburton, D., Ott, J., Penchaszadeh, G. K., Scheinberg, I. H., and Gilliam, T. C., (1993) Mapping, cloning and genetic characterization of the region containing the Wilson disease gene. *Nature Genet.* 5:338–343.
7. The DNA sequence of the oligonucleotide is: GGC TAC CAG GTG CAC CAC CAG AAG CTG GTG TTC TTC GCC GAG GAC GTG (SEQ ID No. 36). A description of the novel binding site is described in Al Bush, et al., in press.
8. Adams, M. D., et al. (1993) Nature Genetics, 4:373–380.
9. Two liver/spleen cDNA libraries were constructed from 20 week post-conceptus fetal material. The libraries were constructed in pT7T3 vector (Pharmacia®) modified to contain a Pac I site. The normalized infant brain cDNA library was constructed from a three month post natal infant in the LAFMID BA vector using the cloning sites HindIII and Not I. The directionally cloned infant brain cDNA library was normalized by a kinetic approach involving priming of single-stranded circles with a Not I-(dT)15 oligonucleotide and controlled extensions (150–200 nt) with Klenow enzyme in the presence of dNTPs and ddNTPs. After purification of the partial duplexes over hydroxyapatite (HAP), melting and reannealing to a moderate Cot, unhybridized (normalized) single-stranded circles were purified over HAP and electroporated into bacteria. The oligo(dT)-primed brain cDNA library used to isolate pWD02 and a Clonetech fetal liver cDNA library were likewise screened.
10. The pWD02 cDNA clone was used to screen a 16,896 clone, chromosome 13-specific cosmid library (Brown, N., Longmire, J. and Deaven, L.). Eleven cosmid clones were identified. Two "walk-steps" were performed using the riboprobe labelling method (6) which extended the cosmid contig to a total of 16 cosmids. A 5' pWD02 oligonucleotide (961–980) was used to prime the DNA synthesis (10) of 50 additional bp of coding sequence from homologous cosmid clones (17G5, 15F1), and a 100 bp PCR fragment including this new sequence was synthesized. 5 cDNA libraries were screened with PCR primers for this fragment (9), two fetal liver/spleen libraries were positive, and one positive clone (pWD5'-191) was identified by screening the libraries with radiolabelled 110 bp fragment. pWD5'-191 was incompletely spliced and contained only 197 bp of new sequence. 5' oligonucleotides were generated (765–789) and used in conjunction with vector primers to amplify the two fetal liver/spleen cDNA libraries. A 550 bp PCR fragment (WD5'b) (253–278), applicants sequenced cosmid 17G5 and obtained 243 bp of additional sequence (FIG. 1). The entire 5414 bp of pWD cDNA is localized to two overlapping clones which span approximately 80 kb.
11. DNA sequencing was performed using the Taw DyeDeoxy Terminator Cycle Sequencing Kit (ABI) as recommended by the supplier. The reactions were analyzed on a ABI model 373A automated sequencer. The forward and reverse primers of pUC18 were used to prime the synthesis of about 300 bp from either end of pWD02. A new set of oligonucleotide primers were generated from the 3'-most end of each new extension and used to prime the next extension as well as to re-sequence the previous sequence for verification. All primers were used in subsequent reactions to sequence first strand cDNA generated from WD polyA+ RNA.
12. A sequence homology search with the WD protein sequence was performed using the BLAST Network Service (Altschul, S. F., Gish, W., Miller, W., Myers, E. W. and Lipman, D. J., (1990), J. Mol. Biol., 215:403.
13. Oedermatt, A., Suter, H., Kraps, R. and Solioz, M., J. Biol. Chem., 268:12775–12779.
14. Ivy, D. M., et al. (1992) J. Bacteriol., 174:4878–4882.
15. Silver, S. and Walderhaug, M., (1992), Microbiol. Rev., 56:195.
16. Silver, S., Nucifora, G., Chu, L. and Misra, T. K., (1989), Trands Biochem. Sci., 14:76–80.
17. Nucifora, G., Chu, L., Misra, T. K. and Silver, S., (1989), Proc. Natl. Acad. Sci. U.S.A., 86:3544–3548.
18. Transmembrane segments have been identified with a hydrophobicity plot and a profile of charged amino acids. The former was based on the hydrophobicity scale of Kyte and Doolittle (28) using a window length of 19 residues. The charge profile for positive charges is generated by assigning a value of +3 to all arginines and lysines, and zero for all other residues. A window of three amino acids is used with the value plotted for residue is corresponding to the average of i−1, i, and i+1. An identical procedure is sued for negative charges except that a value of −3 is now assigned to glutamic and aspartic acids. The amphipathic profile of pWD was calculated by the PREDITOP software (29) according to the hydrophobic moment of Eisenberg, et al., (22) and the hydrophobicity scale of Cornette et al., (30). Secondary structure prediction was carried out with the GCC package using both the Chou-Fasimer (31) and Carnier (32) algorithms. x
19. αβ nucleotide binding domain: B1α1B2 α2B3α3: 825–831; 836–855; 858–883; 885–901; 906–911; 919–929.
20. Branden, C. and Tooze, J., (1991), Introduction to protein structure (Garland Publishing, Inc. New York.
21. Vilsen, B., Andersen, J. P., Clarke, D. M. and Macennan, D. H., (1989), J. Biol. Chem., 264:21024–21030.
22. Eisenberg, D., Weiss, R. M. and Terwilliger, T. C., (1984), Proc. Natl. Acad. Sci. U.S.A., 81:140–144.

23. Devereau, J., Haeberli, P. and Smithies, O., (1984), Nucl. Acid. Res., 12:387–395.
24. Total RNA was extracted by the guanidinium thiocyanate-phenol-chloroform method (Chomczunsky, P J. and Sachi, N., Anal. Biochem., (1987), 162:156–159). Poly (A)+ RNA was isolated (Maniatis, T., Fritsch, E. F. and Sambrook, J., (1989) A laboratory manual. Cold Spring Harbor, Cold Spring Harbor Laboratories) from lymphoblast cell cultures, followed by synthesis of first strand cNDA using reverse transcriptase (Clontech RT-PCR kit), and PCR amplification using nested oligonucleotide primers obtained from the sequence of the "normal" cDNA strand. PCR amplification products were electrophoresed through 1.5% agarose (low melting point, Boehringer) and the DNA fragment was recovered after melting the agarose and passing through a QUIAGEN TIP 20 (Quiagen Inc.). DNA sequence was verified for every base pair by a second, independent PCR amplification and sequencing. Portion of pWD gene sequences were determined by PCR amplification of genomic exonic sequence using oligonucleotide primers for intronic sequence spaced about 50 bp from the exon/intron junction. The pWD cDNA was divided into 14 overlapping regions of 200–500 bp in size. Not all 14 regions were successfully amplified in the lymphoblast samples, possibly due to low level of WD mRNA expression.
25. The only other sequence difference detected was a AG transversion at 1565 giving rise to a conservative lysine to arginine transition. The polymorphism showed allelic association with the WD locus, but was detected as a homozygote two normal individuals (data not shown). It is thus unlikely that this transversion is a causal mutation. This polymorphism was detected by isolation of poly(A)+ RNA from a WD liver biopsy sample, followed by first strand cDNA synthesis (24). The region from nucleotide 882 to 4359 was sequenced using nested primers constructed from the synthesis of the pWD02 cDNA clone (11).
26. The pWD gene was physically mapped to a group of overlapping cosmid clones bracketed by the adjacent microsatellite markers D13S295 and D13S296. These two markers provided the strongest evidence for linkage disequilibrium in a study of 115 WD families from several diverse populations. Applicants have shown by pulsed filed gel electrophoresis that pWD resides less than 80 kb from D13S296 (unpublished observation). pWD is located on the same cosmid clone as D13S301 (6).
27. Gibbs, K., Walshe, J. M., (1979), Quart. J. Med., Sass-Kortsak, A, Bearn, A. G., in The Metabolic Basis of Inherited Disease, 4th ed. Ed. by J. B. Stanbury, et al., McGraw-Hill, New York, 1978, pp. 1098–1126; Scheinberg, I. H., Sternlieb, I., Wilson's Disease, Saunders, W. B., Philadelphia, 1984, page 19.
28. Kyte, J., Doolittle, R. F., (1982), J. Mol. Biol., 157:105–132.
29. Pellequer, J-L., Westhof, E., Van Regenmortal, M. H. V., (1993), Immunol. Lett., 36:83–100.
30. Cornette, J. L., et al. (1987), J. Mol. Biol. 195:659–685.
31. Chou, P. Y., Fasman, G. D., (1974), Biochemistry, 13:222–245.
32. Garnier, J., Osguthorpe, D. J., Robson, B., (1978), J. Mol. Biol., 120:97–120.
33. 500 ng of genomic DNA was amplified using the primers flanking the exon containing the CA transversion. A 337 bp PCR product was purified as described (24) and sequenced using the same primers used for amplification. The sequence of the primers is as follows: 3348=CAG CTA CCA GAG AAG GAC ATG G (SEQ ID No. 22); 3349=AFT TCT GCC TCA GGA GTG TGA C (SEQ ID No. 37). DNA sequence was analyzed with an ABI model 373A automated sequencer. Heterozygotes were reliably detected by manual inspection of characteristic "double peaks" at nucleotide 2142.
34. Mc1 refers to the putative disease gene for Menkes disease (3). CopA is a copper-transporting ATPase from Enterococcus hirai (13). Fix1 is an unknown cation-transporting ATPase from Rhizobium meliloti (Kahn, D., et al. (1989) J. Bact., 171:929). CadA is a cadmium afflux ATPase from Staphylococcus aureus (17).

Third Series of Experiments

Wilson disease is an autosomal recessive disorder of copper transport. Disease symptoms develop from the toxic build-up of copper primarily in the liver, and subsequently in the brain, kidney, cornea and other tissues. A candidate gene for Wilson Disease (WD) (ATP7B) has recently been identified based upon apparent disease-specific mutations and a striking amino acid homology to the gene (ATP7A) responsible for another human copper transport disorder, X-linked Menkes disease (MNK). The cloning of WD and MNK genes provides the first opportunity to study copper homeostasis in human. A preliminary analysis of the WD gene is presented which includes: isolation and characterization of the 5' end of the gene; construction of a genomic restriction map; identification of all 21 exon/intron boundaries; characterization of extensive alternative splicing in brain; prediction of structure/function features of the WD and MNK proteins which are unique to the subset of heavy metal-transporting P-type ATPases; and comparative analysis of the six metal-binding domains. The analysis indicates that WD and MNK proteins belong to a subset of transporting ATPases with several unique features presumably reflecting their specific regulation and function. It appears that the mechanism of alternative splicing serves to regulate the amount of functional WD protein produced in brain, kidney, placenta, and possibly in liver.

Copper is an essential trace element in procaryotic and eukaryotic cells (1) where over thirty proteins, including the electron transport enzymes, are known to require its specific oxidative capacity to perform their normal biological roles. When copper homeostasis is disrupted this same oxidative potential can induce the production of highly reactive free radicals with concomitant extensive cellular damage. The lethal effects of copper imbalance are dramatically illustrated in two human genetic disorders, autosomal recessive Wilson disease (WD) and X-linked Menkes disease (MNK). Clinical features of the X-linked lethal Menkes disease can be explained by copper deficiency resulting from abnormal transport of dietary copper from intestinal cells to cells involved in the synthesis of copper-dependent proteins. Autosomal recessive WD is characterized by copper toxicity believed to result from the loss of ability to i) export copper from liver to bile and ii) incorporate copper into ceruloplasmin in the liver. Copper builds to toxic levels in the liver and other tissues including brain, kidney and cornea. The resulting liver cirrhosis and/or neurological damage are fatal if not treated with copper chelating agents. The genes responsible for both diseases of copper metabolism have recently been identified (2–4, 6). Their protein products are 54% identical and belong to the group of cation transporting P-type ATPases. Menkes and Wilson disease proteins are the only eukaryotic P-type ATPases currently known that are involved in the transport of heavy metals. Detailed structural analysis of these new eukaryotic ATPases is a first step towards understanding their function and regulation. In this study, applicants report the complete exon/intron structure of the WD gene (ATP7B), 162 base pairs of 5'-untranslated region and 96 base pairs of 5'-coding sequence. Applicants provide evidence which suggests that alternative splicing patterns in human brain and liver represents a regulatory mechanism controlling the amount of functionally active copper transporting ATPase. Comparative structural analysis of the full length WD gene product reveals a pair of highly hydrophobic segments N-terminal to the transduction domain that characterizes all heavy metal-binding ATPases. The six heavy metal binding motifs in both Menkes and Wilson disease proteins are shown to resemble copper, cadmium and mercury binding domains of bacterial ATPases. Evolution of the human heavy metal binding motifs is discussed in light of comparative structural analyses.

Materials and Methods

Screening of Genomic Library

A five fold coverage chromosome 13 cosmid library (Los Alamos Laboratories) was gridded onto 11 HYBOND N+ membranes (Amersham®) each with 1536 colonies. DNA probes were radiolabelled to a specific activity of $10^8$ cpm/µg by hexamer priming using a GIBCO BRL oligolabelling kit. Hybridization was performed overnight at 68° C. in 6×SSC, 5×Denhardt's solution, 10% Dextran sulfate, 20 mM sodium phosphate buffer, pH 7.2, 100 µg/ml salon sperm DNA and 0.2% SDS. The filters were washed twice in 2×SSC, 0.2% SDS for 30 minutes at 68° C. and then in 0.2×SSC, 0.2% SDS at 68° C.

Mapping of Cosmid Clones

Cosmid DNAs was prepared using Qiagen columns (Qiagen Inc.) 0.5 µg of cosmid DNA was digested with EcoRI, HindIII or both, analyzed on a 1% agarose gel and transfected onto nylon membrane (HYBOND® N+). Cosmid DNA filters were hybridized to labelled PCR fragments amplified from total human DNA using pairs of primers flanking each of the 21 WD gene exons. Intronic primers used for amplification were:

5'-TTCCCGGACCCCTGTTTGCT-3' (SEQ ID No. 38) and
5'-AATCCTCCTGGTGGGAGTGAGCAC-3' (SEQ ID No. 39) for exon 1;
5'-AGAAGCTGGGATCTTGTAGAAAATATTAGG-3' (SEQ ID No. 40) and
5'-CCTATACCACCATCCAGGAG-3' (SEQ ID No. 41) for exon 2;
5'-GCCCTGAAACCTCTTGTTCTG-3' (SEQ ID No. 42) and
5'-CTACTGATAAACACAGTTGCTGGG (SEQ ID No. 43) for exon 3;
5'-CTTTGTTCGGTTATATTGACTGTGTC-3' (SEQ ID No. 44) and
5'-CCGTTACGCACCCACAGTA-3' (SEQ ID No. 45) for exon 4;
5'-TTCCATGGGAAAAGTTGAAGAATT-3' (SEQ ID No. 46) and
5'-AGACTCCCTGGACTGGCTTT-3' (SEQ ID No. 47) for exon 5;
5'-GCTTTCTGCCAATGCATATTTAAC-3' (SEQ ID No. 48) and
5'-AGAGTTGGGCCCAGGTAGAG-3' (SEQ ID No. 49) for exon 6;
5'-AGGGGAGTGGCTTGTAATCC-3' (SEQ ID No. 50) and
5'-CTTAGCGGGCAGAATATCTGAG-3' (SEQ ID No. 51) for exon 7;
5'-CGCTCATTGAACTCTCCTCC-3' (SEQ ID No. 52) and
5'-AACATGGTGTTCAGAGGAAGTGAG-3' (SEQ ID No. 53) for exon 8;

5'-CAGCTGTCTCTAACACCACGC-3' (SEQ ID No. 54) and
5'-AAACCACATGGGCATCTGAT-3' (SEQ ID No. 55) for exon 9;
5'-CTATTGTAACAGCTGGCCTAGAACC-3' (SEQ ID No. 56) and
5'-CTGTCACTTGCTCAGCCCC-3' (SEQ ID No. 57) for exon 10;
5'-GCTGTCAGGTCACATGAGTGC-3' (SEQ ID No. 58) and
5'-CTGATTTCCCAGAACTCTTCACAT-3' (SEQ ID No. 59) for exon 11;
5'-TTCTTCATAGGTTGTAATTTCCCATG-3' (SEQ ID No. 60) and
5'-GGATCAATGTCAGTAGATTATTTAAAACAC-3' (SEQ ID No. 61) for exon 12;
5'-CCCTGAAATGTCCTTATCTGATTAG-3' (SEQ ID No. 62) and
5'-TCTCAAGGCTTTTCTCTCAATGTG (SEQ ID No. 63) for exon 13;
5'-CAGCTAGGAGAGAAGGACATGG-3' (SEQ ID No. 64) and
5'-AGTTCTGCCTCAGGAGTGTGAC-3' (SEQ ID No. 65) for exon 14;
5'-TCTTGGCTTACAGTTTCCTCTTCC-3' (SEQ ID No. 66) and
5'-TCTGTGGTTTGACCCACCTC-3' (SEQ ID No. 67) for exon 15;
5'-GACTCTTTTGCCTGATATCTGCA-3' (SEQ ID No. 68) and
5'-TGCTGTTAAAAGGATTGCATGGT-3' (SEQ ID No. 69) for exon 16;
5'-CATTGCAAGTGTGGTATCTTGGT-3' (SEQ ID No. 70) and
5'-TACAGCTCAGTGCTGGGCC-3' (SEQ ID No. 71) for exon 17;
5'-CAAGGGTAACTTGAGGTTTCTGC-3' (SEQ ID No. 72) and
5'-TCATTCTGATGGAGAGGAGCAC-3' (SEQ ID No. 73) for exon 18;
5'-TGGGCAGACCCCTTCCTCAC-3' (SEQ ID No. 74) and
5'-AAGCCTTTCTGGGCGCAGCT-3' (SEQ ID No. 75) for exon 19;
5'-GACCTAGGTGTGAGTGCGAGTT-3' (SEQ ID No. 76) and
5'-GTTTAGCCAGGGCTTCTGAGG-3' (SEQ ID No. 77) for exon 20;
5'-GGATGAGAGGCCTTCACCAG-3' (SEQ ID No. 78) and
5'-CTCTCCAGGTCAGGCTTCTTAT-3' (SEQ ID No. 79) for the protein coding part of exon 21.

A restriction map was constructed by calculating and compiling the migration distances of hybridization-positive restriction fragments.

Amplification and Cloning of the 5' End of WD cDNA

The reverse transcriptase reaction was performed with a 0.5 µg of human liver poly(A+)-RNA (Clontech), first strand cDNA synthesis kit (Clontech), and 50 picomoles of a 21-mer anti-sense primer 5'-AATGGAGCTGACACAGGACTG-3' (SEQ ID No. 80) deduced from the 5' end of the clone p5'WDb (2). The single stranded cDNA was polycytydilated with terminal deoxynucleotidyl transferase Boehringer Mannheim®) and dCTP for 1 to 15 minutes. A nested anti-sense primer (5'-GCAGGTCATGCCCTCCAC-3' SEQ ID No. 81) and dG$_{18}$ oligonucleotide, both containing NotI recognition sequences at their 5' end, were used to amplify the 5' WD cDNA. The PCR product was cloned into NotI-digested pUCBM 20 vector (Boehringer Mannheim®). The longest cDNA clone (pKP 101) contained a 625 bp insert.

Reverse Transcription and Polymerase Chain Reaction

The reverse transcriptase reaction was performed using first strand cDNA synthesis kit (Clontech), random hexamers as primers, and 0.5 µg of poly(A+)-RNA from human brain, liver, placenta, and kidney (Clontech). The reverse transcriptase cDNA mixture was subjected to 30 amplification cycles. Sense primers used in the amplification were:

5'-CACAACATAGAGTCCAAACTCACG-3' (SEQ ID No. 82) (#3309, exon 5),

5'-AAACTGGTGGAAGAGGCTCAG-3' (SEQ ID No. 83) (#3354, exon 11) and

5'-CAGTCACTAAGAAACCCGGAAG-3' (SEQ ID No. 84) (#3313, exon 11).

Anti-sense primers used in amplification were:

5'-TGTCCTCACCAAGGGTCACA-3' (SEQ ID No. 85) (#3312, exon 9),

5'-GATGAGGATGCCGTTCTGCG-3' (SEQ ID No. 86) (#2, exon 13), and

5'-GCCCAAGGGGTGTTCACT-3' (SEQ ID No. 87) (#3327, exon 14).

PCR fragments from the above reactions were purified according to (32) and sequenced.

DNA Sequencing

DNA sequencing was performed using the Taq DyeDeoxy Terminator Cycle Sequencing Kit (ABI) as recommended by the supplier. Modified sequencing reactions included 20% DMSO as described in (16). The reactions were analyzed on a ABI model 373A automated sequencer.

Protein Structure Analysis

Analysis of the WD protein sequence (multiple alignments, construction of hydropathy profiles of P-type ATPases and evolutionary tree for metal-binding sites) was performed using the GENEWORKS program package (IntelliGenetics).

Experimental Results

Cloning the 5' End of the WD Gene (ATP7B)

Applicants and others (2, 4) recently reported a partial WD cDNA sequence lacking the 5'-end region of ATP7B which encodes the amino-terminal portion of the protein. To clone the entire WD cDNA, applicants used a 5'-RACE protocol (see Materials and Methods). The longest cDNA clone that applicants identified (pKP-101) contained 162 base pairs of the 5'-untranslated region as well as 463 nucleotides encoding the $NH_2$-terminal portion of the WD protein. FIG. 10 shows the predicted functional AUG start codon 96 nucleotides upstream of the previously reported start site (4). The functional AUG suggested here matches the consensus sequence required for optimum translation (5) and it makes the longest possible open reading frame (i.e. it satisfies the first AUG rule (5)). Thus, in comparison to the two previous reports of WD DNA sequence (2, 4), applicants present an additional 222 base pairs at the 5'-end of the gene. The two previous reports also differ in the region of cDNA encoding the carboxyl-terminal part of the protein starting from position 3133 (2) which corresponds to position 4141 (4). The divergence begins 73 nucleotides from the 5' boundary of exon 21 and thus cannot be attributed to the presence of an alternatively spliced exon. This portion of the cDNA sequence is verified in applicants' laboratory by three independent cDNA clones (2) as well as sequence derived from the homologous cosmid clone cos177F8 (Lawrence Livermore National Laboratories). Furthermore, the sequence applicants' reported (2) is highly homologous to the corresponding region from the Menkes cDNA clone (6), whereas that reported by Bull et al. (4), is completely divergent in this region. Since the part of the sequence reported by Bull et al. (4) does not map to the set of overlapping cosmids spanning the WD gene, applicants suggest that the last 247 nucleotides of the cDNA published in (4) are the result of a cloning artifact.

Organization of the WD Gene

Figure 11:
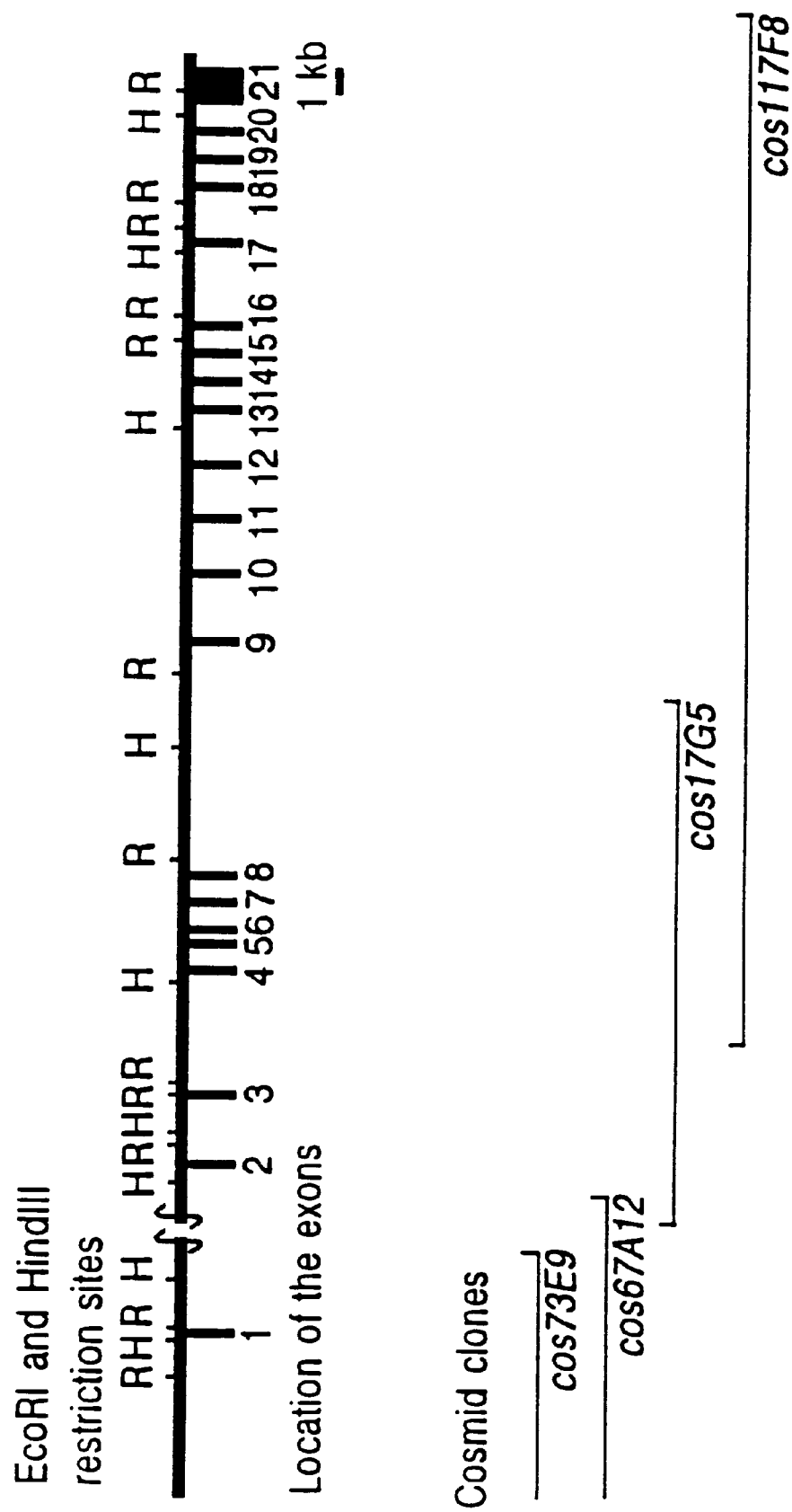
FIG. 11 Organization and physical map of the human WD gene. Upper part: EcoRI (R) and HindIII (H) map of the WD gene locus and location of the 21 exons. Lower part: overlapping cosmid clones are shown relative to the restriction map.

A CH13-specific cosmid library (16,896 clones) was screened with the 4 kb WD cDNA clone, pWD02 (2). Eleven homologous cosmids were identified and ordered by dot-blot hybridization to WD cDNA specific oligonucleotide probes. Two overlapping cosmids (cos17G5, cos117F8) contained this entire portion of the WD gene but not the 5'-most sequences identified by the 5'-RACE protocol. The library was re-screened with a 213 bp probe from pKP-101 and cosmid clones 73E9 and 67A12 (FIG. 11) were shown to span the 5'-end of the gene. A large intron of approximately 20 kb was identified between exons 1 and 2. Thus, the WD gene appears to span at least 80 kb of genomic DNA which has been completely subcloned in three overlapping cosmids. To determine the exon/intron structure of the WD gene, applicants synthesized 24 oligonucleotide primers which are distributed uniformly throughout the cDNA sequence. This primer set was used to sequence exonic DNA and contiguous intronic DNA in the three overlapping cosmid clones. Comparison of the cDNA and genomic DNA sequence revealed the exon organization of the WD gene as well as sequences of exon/intron boundaries and adjacent introns. This analysis revealed a total of 21 exons including 4 exons (exons 6, 7, 8 and 12) not present in the predominantly brain cDNA sequence which applicants previously reported (2). The exons range in size from 77 bp (exon 6) to 2,355 bp (exon 21) (Table IV). The splice signals in all 20 introns conform to published consensus sequences (7). Until the transcription initiation site(s) is identified the possibility of additional exon(s) upstream of exon 1 cannot be excluded.

TABLE IV

| Exon | Length | Coordinates | Splice Acceptor | Splice Donor |
|---|---|---|---|---|
| 1 | Unknown | 1–213[a] | Unknown | GCC AGT CGG AAA/gtgagttttgtt<br>Ala Ser Arg Lys |
| 2 | 1212 bp | 214–606[a]<br>plus<br>1–841[b] | ttttctttttag/ATC TTA TCT AAG . .<br>Ile Leu Ser Lys | . GTC GTT TCT G/gtacgtagtgtg<br>Val Val Ser G-lu |
| 3 | 258 bp | 842–1099[b] | attttatcctag/AA AGC TGT TCT .<br>G-lu Ser Cys Ser | . AAA GAA GCT G/gtaagagatgaa<br>Lys Glu Ala G-ly |
| 4 | 164 bp | 1100–1263[b] | atggttgccag/GT GTT CTC TCC . .<br>G-ly Val Leu Ser | . ATT GAG CTG ACA/gtaagtactgggtg<br>Ile Glu Leu Thr |

TABLE IV-continued

| Exon | Length | Coordi-nates | Splice Acceptor | Splice Donor |
|------|--------|--------------|-----------------|--------------|
| 5 | 162 bp | 1264–1425[b] | cctgtgttgcag/ATC ACA GGG ATG . .<br>　　　　　　　　Ile Thr Gly Met | AAA ATT ATT GAG/gtaagtaattca<br>Lys Ile Ile Glu |
| 6 | 77 bp | 1813–1889[c] | tttaatgacaaag/GAA ATT GGC TTT .<br>　　　　　　　　Glu Ile Gly Phe | GAA ATA AAG CA/gtaggtagaaca<br>Glu Ile Lys Gl-n |
| 7 | 175 bp | 1890–2064[c] | tttgctttccag/G TGG AAG AAG . . .<br>　　　　　　　Gl-n Trp Lys Lys | ACC TTT GTC CAG/gtatatatgaga<br>Thr Phe Val Gln |
| 8 | 234 bp | 2065–2298[c] | cttgtctttcag/CTC CTC GGT GGG . .<br>　　　　　　　Leu Leu Gly Gly | CAC TTG GCA AAG/gtaacagcagct<br>His Leu Ala Lys |
| 9 | 92 bp | 1426–1517[b] | gttatttcctag/AGC AAA ACC TCA . . .<br>　　　　　　　Ser Lys Thr Ser | TTA ATC ATC AG/gtgagttatggt<br>Leu Ile Ile Ar-g |
| 10 | 128 bp | 1518–1645[b] | cgtttgttgcag/G GAG GAG CAA . . .<br>　　　　　　　Ar-g Glu Glu Gln | CTC ATC ACA G/gtgagatggctt<br>Leu Ile Thr G-ly |
| 11 | 155 bp | 1646–1800[b] | tcctacgtctag/GA GAA GCC ATG . .<br>　　　　　　　G-ly Glu Ala Met | CAG ATG TCA AAG/gtaatgaagaaa<br>Gln Met Ser Lys |
| 12 | 135 bp | 2674–2808[c] | ttattttcatag/GCA CCC ATT CAG . .<br>　　　　　　　Ala Pro Ile Gln | AAA TAC TTT CCT/gtaagttgaatg<br>Lys Tyr Phe Pro |
| 13 | 195 bp | 1801–1995[b] | tcctgttttcag/AAC CCC AAC AAG . .<br>　　　　　　　Asn Pro Asn Lys | ATG GCG CAC AAG/gtcagcctgtag<br>Met Ala His Lys |
| 14 | 183 bp | 1996–2178[b] | tgtttttggcag/ATA AAG ACT GTG . .<br>　　　　　　　Ile Lys Thr Val | TAC TGT AAA GAG/gtacgtggactt<br>Tyr Cys Lys glu |
| 15 | 169 bp | 2179–2347[b] | ccaccttcccag/GAA CTT GGA ACA . .<br>　　　　　　　Glu Leu Gly Thr | GCA GAA AAA G/gtattgctggct<br>Ala Glu Lys A-sp |
| 16 | 144 bp | 2348–2491[b] | tcttttgaatag/AT GCA GTC CCC . .<br>　　　　　　　A-sp Ala Val Pro | GCT ATT GAC G/gtatcttctgct<br>Ala Ile Asp G-ly |
| 17 | 143 bp | 2492–2634[b] | ggttcgctccag/GT GTG CTC TGT . .<br>　　　　　　　G-ly Val Leu Cys | ATT GCC ACC CAG/gtacagccttt<br>Ile Ala Thr Gln |
| 18 | 204 bp | 2635–2838[b] | cttttgtcttag/GTT GGC ATC AAC . .<br>　　　　　　　Val Gly Ile Asn | GTC CTT ATC AGA/gtgagtgtggct<br>Val Leu Ile Arg |
| 19 | 118 bp | 2839–2956[b] | cctctccatcag/AAT GAT TTG CTG . .<br>　　　　　　　Asn Asp Leu Leu | ATT GCA GCA G/gtaggcagctct<br>Ile Ala Ala G-ly |
| 20 | 103 bp | 2957–3059[b] | tttcttccccag/GT GTC TTC ATG . .<br>　　　　　　　G-ly Val Phe Met | CAG CTC AAG TG/gtgagtcccctc<br>Gln Leu Lys Cy-s |
| 21 | 2,355 bp | 3060–5414[b] | cctgctttccag/C TAT AAG AAG . . .<br>　　　　　　　Cy-s Tyr Lys Lys | Polyadenylation |

Exon 1 = Seq. ID Nos. 38, 39.
Exon 2 = Seq. ID Nos. 40, 41.
Exon 3 = Seq. ID Nos. 42, 43.
Exon 4 = Seq. ID Nos. 44, 45.
Exon 5 = Seq. ID Nos. 46, 47.
Exon 6 = Seq. ID Nos. 48, 49.
Exon 7 = Seq. ID Nos. 50, 51.
Exon 8 = Seq. ID Nos. 52, 53.
Exon 9 = Seq. ID Nos. 54, 55.
Exon 10 = Seq. ID Nos. 56, 57.
Exon 11 = Seq. ID Nos. 58, 59.
Exon 12 = Seq. ID Nos. 60, 61.
Exon 13 = Seq. ID Nos. 62, 63.
Exon 14 = Seq. ID Nos. 64, 65.
Exon 15 = Seq. ID Nos. 66, 67.
Exon 16 = Seq. ID Nos. 68, 69.
Exon 17 = Seq. ID Nos. 70, 71.
Exon 18 = Seq. ID Nos. 72, 73.
Exon 19 = Seq. ID Nos. 74, 75.
Exon 20 = Seq. ID Nos. 76, 77.
Exon 21 = Seq. ID Nos. 78, 79.

Table IV

The nucleotide sequence of exon/intron boundaries of the human WD gene.

Exon sequences are shown in upper case letters and intron sequences in lower case. The coordinates of splice junctions are given relative to their position in cDNA sequences presented in FIG. 10[(a)] and published in (2) and (4)[b] and [c], respectively.

The three overlapping cosmids were digested with restriction endonucleases and analyzed by electrophoresis and Southern blot hybridization with exon-specific probes. A restriction endonuclease map of the WD gene with corresponding exon positions is presented FIG. 11.

Evidence for Tissue-specific Splicing of Wilson Disease Gene Transcripts

Figure 12A:
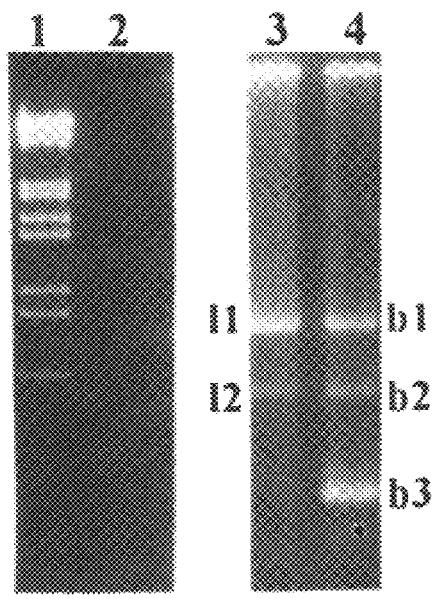
FIG. 12 Detection of alternative splicing between exons 5 and 9 of the WD mRNA by RT-PCR. RT-PCR was performed as described in Materials and Methods with primers #3313 and #3327 on human brain (lane 4), liver (lane 3) and water as a negative control (lane 2). The PCR products were separated on a 2.0% agarose gel and stained with ethidium bromide. Markers (lane 1) is a λ DNA HindIII/EcoRI digest. The diagram on the right depicts the schematic membrane folding of the WD protein encoded by exons 5–9.
Figure 12B:
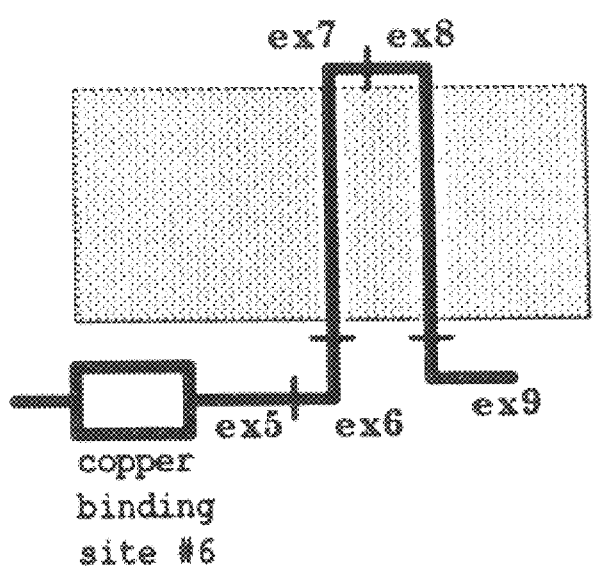
Figure 13A:
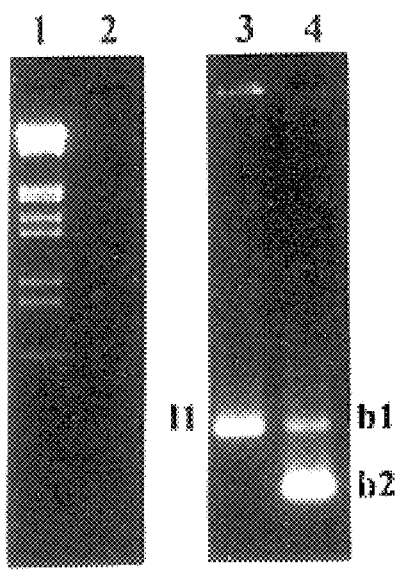
FIG. 13 PCR analysis of alternative splicing patterns of WD gene exons 11–13 (A) and 11–14 (B). PCR analysis of first strand cDNA from human brain (lane 4) and liver (lane 3) as well as with water (negative control, lane 2) was performed with primers #3354 and #2 (A) and #3313 and #3327 (B) followed by separation on a 2% agarose gel. The diagram depicts the membrane folding of the WD protein encoded by exons 11–14.
Figure 13B:
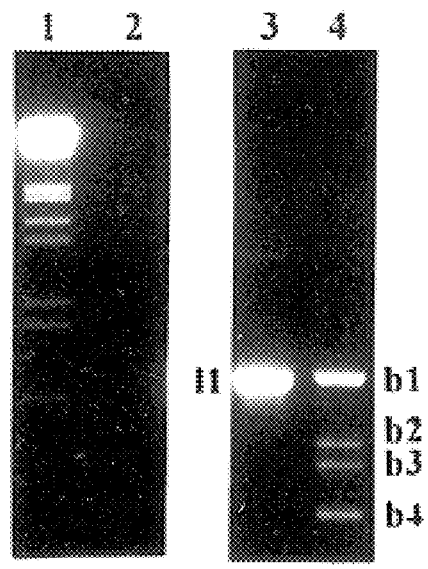
Figure 13C:
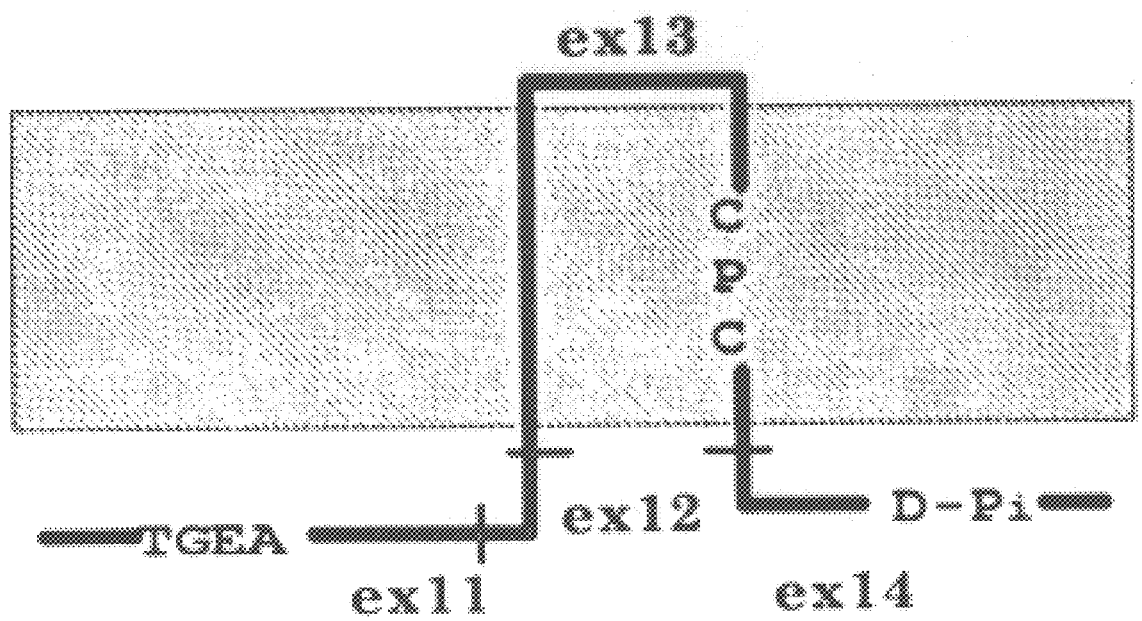
Figure 14A:
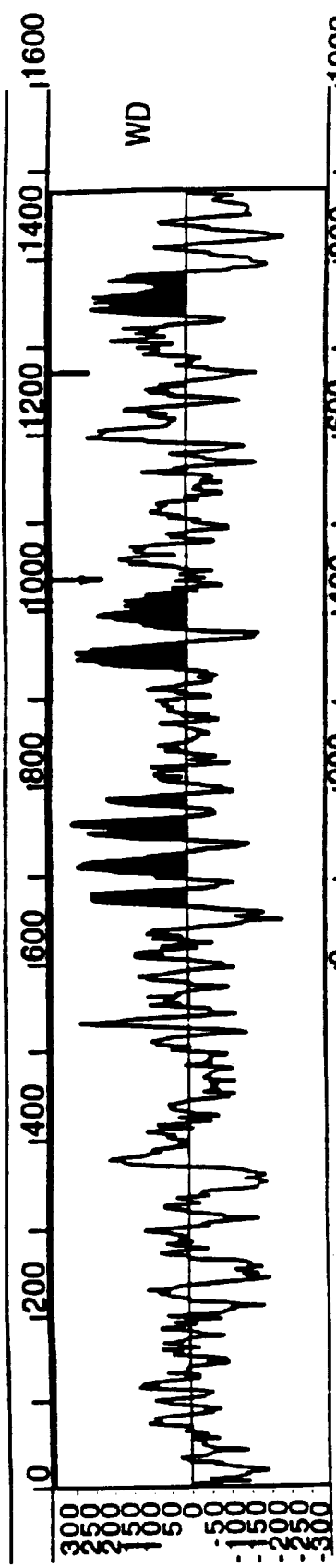
FIG. 14 Comparison of hydropathy profiles of heavy metal transporting P-type ATPases (WD, Wilson disease protein; CopA, copper transporting ATPase from *E.hirae*; Cd-ATPase, cadmium transporting ATPase from *S.aureus*) and non-heavy metal transporting P-type APTases (Mg-ATPase, magnesium transporting ATPase from *S.typhiurium*; ATCA-RABIT, rabbit calcium transporting ATPase). The abscissa indicates amino acid position and ordinate indicates degree of hydrophobicity. Hydropathy profiles are aligned by position of the phosphorylation site indicated by an arrow; the vertical line marks the position of the hinge motif DMVGDG (SEQ ID No. 31). Filled-in peak regions are predicted to span the membrane according to the algorithm of Kyte and Doolittle (39 of the third series of experiments).
Figure 14B:
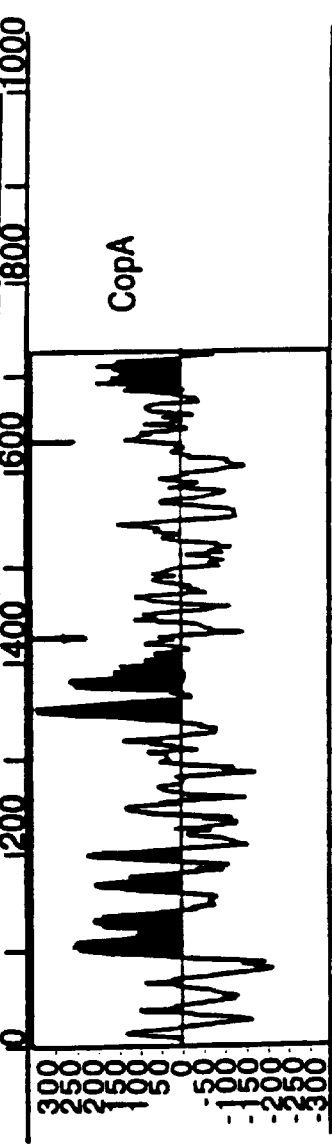
Figure 14C:
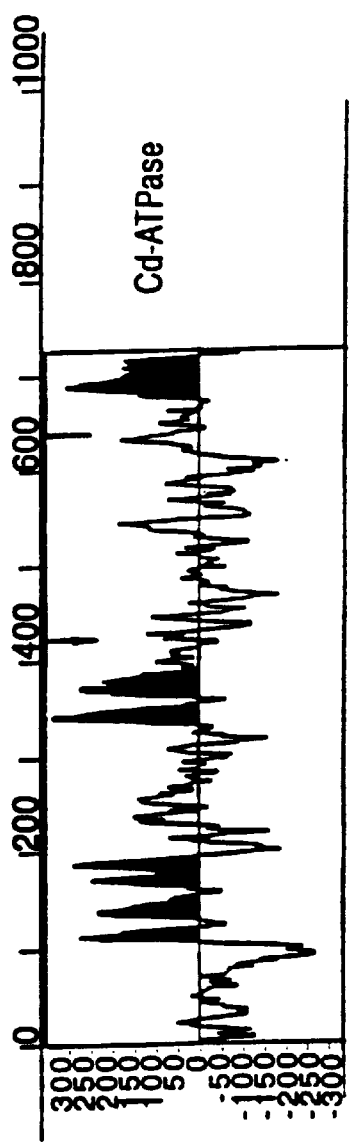
Figures 14D, 14E:
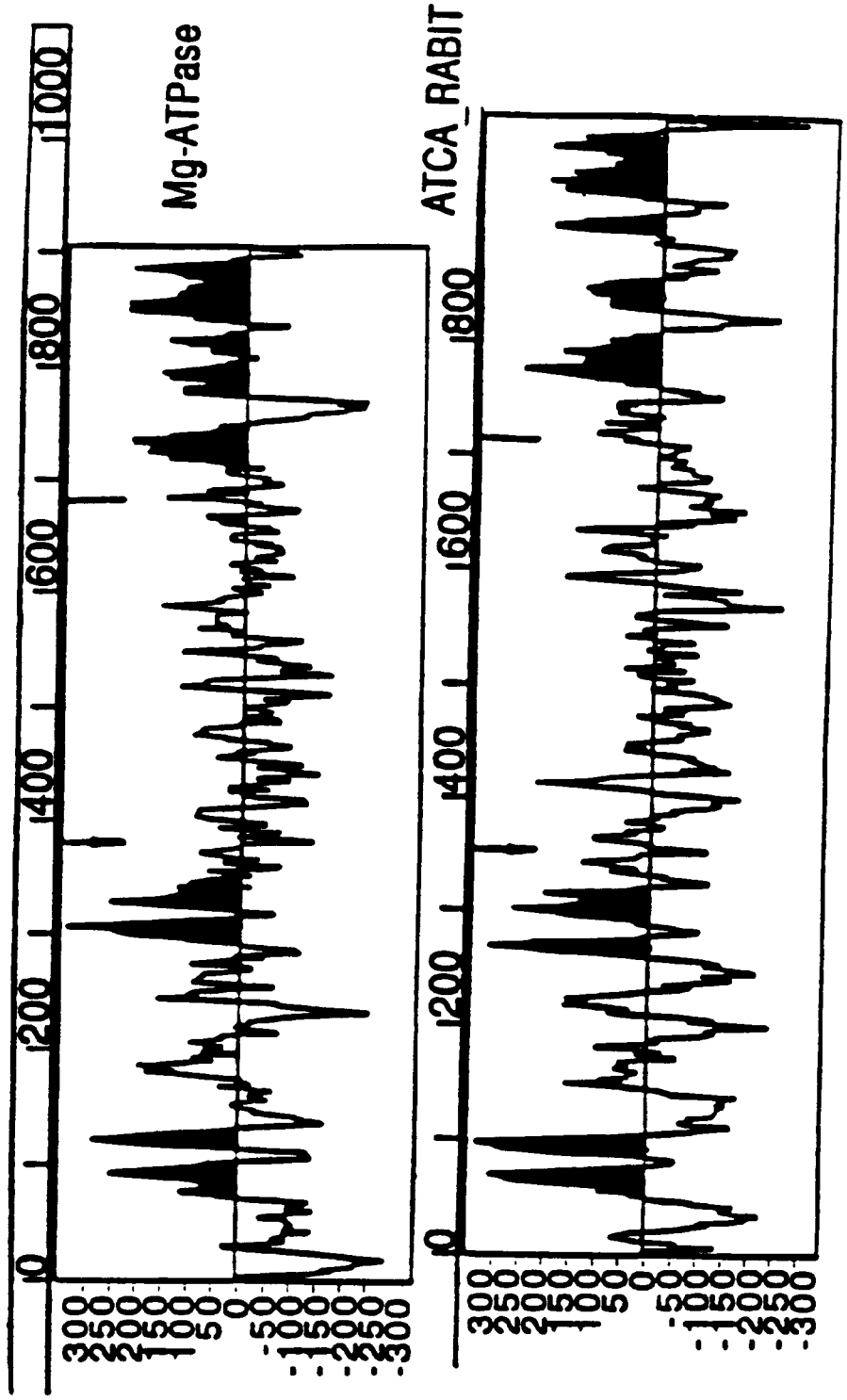
Figure 16:
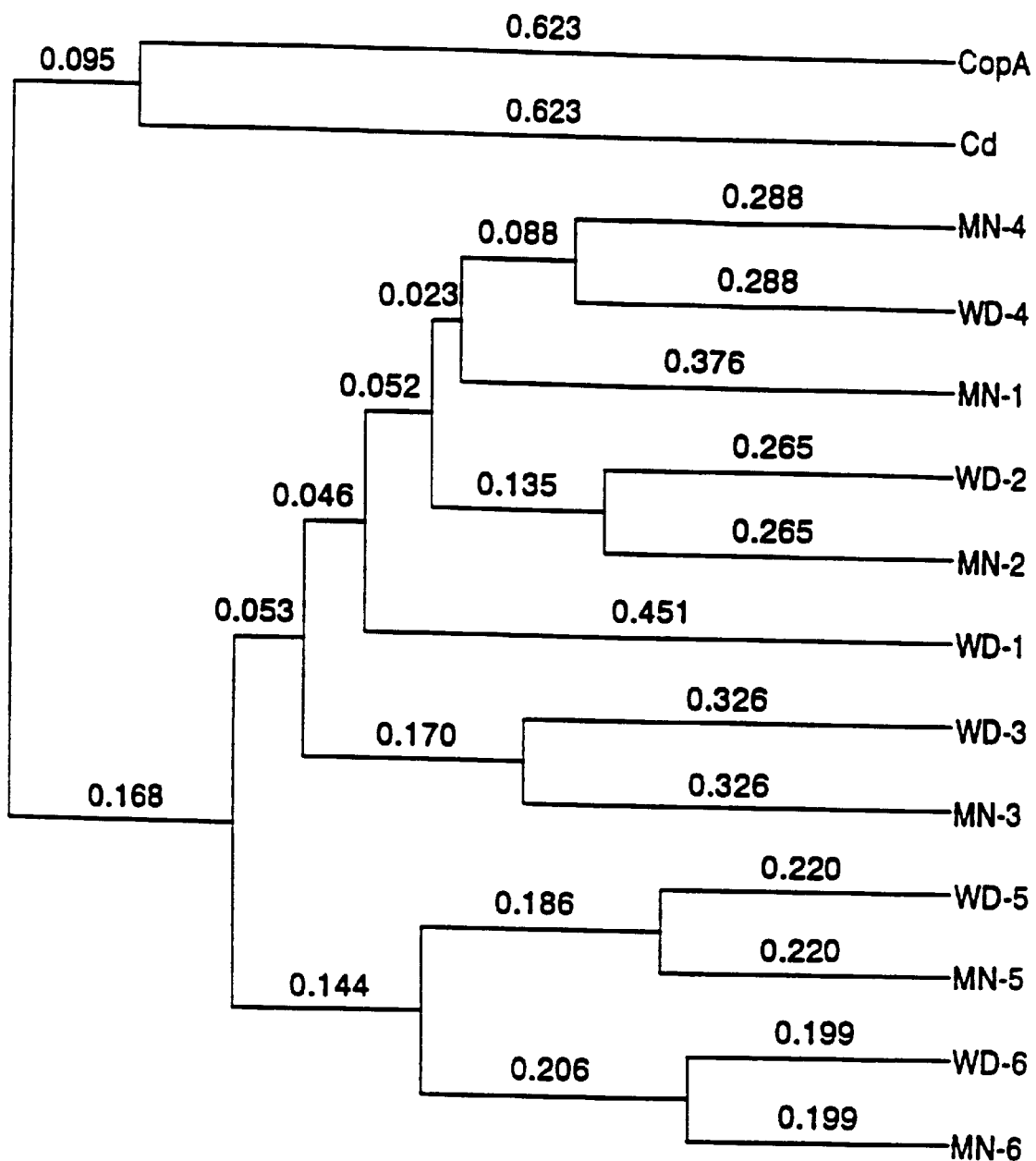
FIG. 16 Graphic representation of the sequence relationships between metal-binding sites of the most similar heavy metal transporting ATPase. The tree is an output of the UPGMA Tree program (IntelliGenetics Inc.) that calculates evolutionary relationship of the sequences in alignment. The length of the horizontal lines is proportional to the evolutionary distance between the sequences. Scores above the horizonal lines represent a number of mismatches between the sequences connected by vertical lines divided by the length of a shorter sequence; lower score indicates higher similarity. WD1-6 and NM1-6 are metal-binding repeats of the WD gene and Menkes disease gene products, respectively; CopA and Cd are the metal-binding sites of copper transporting ATPase from *E.hirae* (8 of the third series of experiments) and cadmium transporting ATPase from *S.aureus* (10 of the third series of experiments), respectively.

Applicants had previously noted (2) that WD cDNA sequence prepared from brain mRNA was lacking two segments of DNA sequence which were present in both the highly homologous Menkes disease cDNA sequence (6) and in the liver cDNA version of the WD gene sequence (4). The segments missing from the brain cDNA clones align precisely with the ends of exons 5 and 11 indicating a mechanism of alternative splicing in brain versus liver tissue. To evaluate the possibility of alternative splicing in the WD gene, applicants used a sensitive and selective PCR-based mRNA amplification method. Poly(A+)-RNA from either liver or brain tissue was primed with random oligonucleotides and reverse transcribed. The resultant cDNAs were PCR amplified with primers flanking the sites of suspected alternative splicing and PCR products were purified by agarose gel electrophoresis and sequenced. RT-PCR amplification with primers flanking the region spanned by exons 5 and 9 (see Materials and Methods and FIG. 12) detected two bands in liver and three bands in brain (FIG. 12). Sequence analysis revealed that the smallest PCR band in brain, which was not detected in liver (band b3 on FIG. 12), is identical to the corresponding segment of the pWD02 clone previously reported in (2). The largest bands in both liver and brain (bands 11 an b1, respectively in FIG. 12) contained three additional exons (ex6, ex7, ex8) not found in the brain cDNA clone pWD02 (2) but which were present in the liver cDNA clones reported previously (4) and in the cDNA sequence reported in this study. Sequencing of PCR bands b2 and 12 revealed that their exon composition is ex5-ex6-ex7-ex9 and ex5-ex8-ex9, respectively. The consequences of exon skipping in this region of the WD gene is illustrated in the right panel of FIG. 12 where the exon structure of the gene is superimposed on the model of protein folding within the membrane. The absence of the protein regions encoded by exons 7 and 8 would predictably lead to gross topological changes in the membrane-spanning portion of the protein which would presumably render the protein incapable of transporting heavy metal ions across the membrane (see Discussion). Analogous experiments were performed to detect splice variants in the region of exons 11 and 13 where the second gap in homology between brain WD cDNA and the Menkes disease gene as been detected. RT-PCR with primers spanning exons 11 and 13 (see Materials and Methods and FIG. 13). DNA sequence analysis shows that bands 11 and b1 are identical and consist of exons 11–12–13, while band b2 does not contain exon 12 and corresponds to the DNA sequence reported previously for the brain cDNA clone, pWD02 (2). Because exons 11 and 13 encode functionally important parts of the protein, applicants performed similar experiments spanning this segment of cDNA. Primers were generated which span the region encompassed by exons 11 through 14 (see Materials and Methods and FIG. 13) and the PCR amplification products are shown in FIG. 13. A single product is seen from liver while multiple splicing forms are produced from the brain mRNA. DNA sequencing revealed the presence of a full-length transcript represented by bands 11 and b1 as well as three truncated variants. Exon compositions have been determined for bands b2 (ex11-ex12-ex14) and b4 (ex11-ex14); band b3 has not been sequenced. Both b2 and b4 truncated forms lack exon 13 (FIG. 13) which encodes the transmembrane stretch containing the Cys-Pro-Cys motif, which is invariant in all heavy metal ion transporting ATPases (6, 8–10). This proline residue is highly conserved in all P-type ATPases and was shown to be essential for the formation of high affinity calcium binding sites in Ca-ATPase of sarcoplasmic reticulum (11). Once again, it appears that the brain produces alternative transcripts of the WD gene which would not be expected to encode a functionally active copper transporting ATPase. This conclusion was supported by a check of the remaining exons for splicing variants in brain. The single additional variant detected was a transcript lacking exon 17, the region encoding the ATP-binding domain of the WD protein (data not shown). All these data support the contention that splicing of the WD gene is differentially regulated in adult human tissues, and that in the brain (as well as in kidney and placenta—data not shown) exon skipping produces truncated forms of mRNA which predictably would not be translated to functionally active transmembrane ATPase molecules.

Amino Acid Sequence Analysis of the WD Gene Product

Amino acid sequence comparison of the WD gene product to characteristic P-type ATPases reveals the canonical primary structural motifs defined in (41) including: transduction domain (TGEA (SEQ ID No. 33), residues 548–551; all amino acid coordinates are as in reference 2); phosphorylation domain (DKTGT [SEQ ID No. 88], 672–675); ATP-binding domain (TGDN (SEQ ID No. 89), 865–868); and the sequence AMVGDGVND (SEQ ID No. 90) (908–916) which is highly homologous to the "hinge" region—a flexible loop, connecting the ATP binding domain with the transmembrane portion of the molecule (2). The hydropathy profile of the WD gene predicts four putative transmembrane fragments (first shaded peaks in FIG. 14) in the region N-terminal to the TGEA/S (SEQ ID Nos. 91, 92) motif, while most of the topological models of P-type ATPases depict two transmembrane segments in this part of the molecule. The topological model for the bacterial Cu-transporting ATPase, CopB (8), is an exception with four putative transmembrane segments N-terminal to TGES, suggesting that the additional transmembrane hairpin loop in this region may be a characteristic feature of the heavy metal transporting ATPases. To test this possibility, the WD hydropathy profile was compared with similar profiles from prokaryotic and eukaryotic ATPases known to transport different cations (FIG. 14). This analysis led to the following interesting findings: a) The hydropathy profile of the predominant WD gene product expressed in liver is almost identical to the hydropathy profile of Menkes disease gene product (not shown); b) Hydropathy profiles of other heavy metal-transporting ATPases including the bacterial ATPases CopA (8), CopB (8), Cd-ATPase (10) and the FixI gene product (9) also have four putative transmembrane segments in this region (exemplified by CopA and Cd-ATPase in FIG. 14), whereas all known non-heavy metal ion eukaryotic ATPases and bacterial ATPases have two transmembrane segments (exemplified by Mg-ATPase and Ca-ATPase in FIG. 14).

Applicants propose that the presence of two transmembrane helical hairpins at the N-terminal domain is a characteristic feature of heavy metal-transporting P-type ATPases, as is the presence of the CPC and SEHPL motifs. A feature shared in common with other ATPases including human Na, K-ATPase, plant H-ATPase, and bacterial Cd-ATPase, is the presence of a hydrophobic peak around the 1200th residue (FIG. 14) which includes the ATP-binding domain. This stretch of hydrophobic amino acid residues may be involved in the formation of a hydrophobic pocket as part of the ATP-binding domain and may interact tightly with the membrane without crossing it. In fact, the interaction between this region and the membrane bound portion was recently directly demonstrated for Na, K-ATPase (12).

Metal-binding Sites; Size, Similarity, Evolution

In the N-terminal segment of the WD gene product there are six copper-binding motifs, GMXCXSC, which are repeated with 70–80 amino acid residue spacings. Noting that this is approximately the same size as the N-terminal domain that contains the putative copper-binding motif in the bacterial CopA ATPase (8), applicants compared with CD, MNK, CopA, and Cd-ATPase sequences over a 70 amino acid region beginning 8 residues N-terminal to the "copper-binding" GMXCXSC motif. As shown in FIG. 15, it is clear that the size of the conserved region, 65–70 residues, is longer than that previously proposed for the copper binding sites of both Wilson and Menkes disease gene products (2, 4, 6). Applicants propose that this longer segment represents the copper-binding unit and that is likely arose from bacterial precursors through a process of duplication. Several recent reports (2, 6, 13, 14) describing the sequence similarity between copper and mercury-binding reductase (MerA) gene contains 2 repetitive sequences, that are thought to be involved in mercury binding (15). They are 72 amino acid residues long (see FIG. 15) and curiously more similar to the first binding motif of the WD gene product than to the corresponding sequence of CopA. As shown in FIG. 15, the most conserved region of copper binding is about 12 amino acid residues. When the CopA terminal domain was compared with each of the WD repeats, it was found that sequence similarity gradually increases from 11% identity with the C-terminal most repeat WD6/CopA (the percent of identical amino acid residues varies from 35% to 49% among different pairs of WD repeats (data not shown). The construction of the evolutionary tree revealed that the highest degree of amino acid similarity within the metal binding motifs was detected between analogous sites of the MNK and WD gene products (see FIG. 15) 67% amino acid identities were detected between WD 6 and MNK 6. In fact, identity is higher between analogous intergenic motifs than among intragenic motifs excepting WD 1 which has a higher similarity to WD 4 (47%) than to corresponding MNK 1 (only 28%).

In summary, the greater similarity between corresponding domains of the WD and Menkes disease proteins (especially for the domains 5 and 6), together with the increasing identity between the CopA domain and WD/MNK domains 1 to 6 (N-terminal to C-terminal) argues that evolution of the N-terminal binding domain was formed by gene duplication (5 and 6 being the latest addition) and that this fragment of approximately 600 amino acids was subsequently "spliced" with the ATPase "core". According to this hypothesis, the resultant product was the common ancestor for both the WD and Menkes disease ATPases.

Experimental Discussion

Applicants have extended the 5'-end of the WD gene (ATP7B) to include the fragment encoding an additional 32 amino acids of protein sequence (2, 4) and a partial 5'-untranslated region. The current WD cDNA sequence includes at least 162 base pairs of 5'-UTR, 4,395 base pairs of protein coding sequence and 2,084 base pairs of 3'-UTR (GenBank accession number U11700). Further studies are needed to identify the promoter region of the WD gene as well as to determine if there are additional exons upstream of the 5'-most sequence. Efforts to date have apparently been stymied by unusual secondary structure in the 5'-UTR. Comparison of genomic and cDNA sequence reveals 21 exons ranging in size from 2,355 base pairs to 77 base pairs. The description of intronic sequence flanking each of the exons will permit rapid PCR-based screening protocols to identify Wilson disease mutations (oligonucleotide primers which were used to amplify all 21 WD gene exons are listed in Materials and Methods). Applicants' previous report of the WD cDNA sequence generated primarily from brain cDNA clones (2) indicated that the brain transcript was lacking several exons which were present both in the predominant liver WD transcript (4), and also in the highly homologous Menkes disease cDNA sequence (6). RT-PCR experiments performed on poly(A+)-RNA isolated from liver and brain tissue indicate that the most abundant liver transcript contains all the exons found in the genomic DNA, while brain splicing variants consist of several combinations of skipped exons including: exon 17 encoding the ATP-binding site; exon 13 encoding the transmembrane helical hairpin containing an invariant Cys-Pro-Cys; exons 6, 7 and 8 which encode a predicted transmembrane helical hairpin N-terminal to the transduction domain; and exon 12 which has an unknown function. Skipping of exons 6, 7, 8, 12 and 13 maintains the open reading frame of the gene while the skipping of exon 17 creates a frameshift that produces a stop codon downstream. Assuming this splicing form is translated, it would generate a truncated protein product. Some of these splicing forms have also been found in human kidney and placenta (data not shown). At this point, applicants can only speculate how alternative splicing changes the function of the WD protein, although applicants predict that some of these splicing forms, if translated, would not produce a functionally active copper transporting ATPase. Ultimately, gene expression studies will be required to answer these questions. It has been proposed that alternative splicing can be involved in the on/off regulation of a particular gene product or it can produce alternative products with distinct functions (17). In the case of Ca-ATPase, alternative splicing can provide a fine tuning for regulation of this complex molecule by adding or removing a cAMP-dependent protein kinase site as well as small protein fragments involved in interactions with phospholipids and calmodulin (18, 19). In the case of the WD protein alternative splicing may represent a tissue-specific mechanism to regulate the amount of mRNA encoding the full-length, functionally active protein. This mechanism could supplement the apparent tissue-specific transcriptional regulation of the WD gene expression (2, 4). Alternatively, the variant transcripts could encode proteins with distinct cellular functions; for example, the truncated forms of the WD protein with intact metal-binding sites might serve as copper-storage proteins which shuttle copper ions inside the cell.

The exonic structure of the WD gene is similar to some P-type ATPases (20–23) with separate exons encoding all putative transmembrane segments, the highly conserved phosphorylation and hinge domains (21, 24) and the carboxy-terminal hydrophilic domain. In contrast, the WD gene contains a total of 5 exons comprising the central portion of the protein including the phosphorylacion and hinge domains compared with 6–8 exons in other P-type ATPases. This disparity is correlated with a large cytoplasmic loop located between these functional domains in other eukaryotic P-type ATPases, which is abbreviated in the WD protein. It is interesting that the WD protein is also missing a C-terminal membrane-bound segment characteristic of many P-type ATPases (see below) since several ATPase studies indicate an interaction between this region and the cytoplasmic loop portion of the protein (12, 25). Overall, the structure of the WD protein is consistent with the idea that exons tend to preserve functional modules from their ancestral protein predecessors (26).

Recent data indicates that the WD-gene product belongs to a subfamily of eukaryotic P-type ATPases and is closely related to bacterial heavy metal ATPases (2, 4). Two unique amino acid motifs, CPC (628–630, ref. 2) and SEHPL (712–715, ref. 2) as well as an additional transmembrane helical hairpin in the N-terminus of the molecule (FIGS. 15 and 17), were shown to be present in both procaryotic and eucaryotic ATPases involved in Cu-transport (2–4, 6, 14), but not in other P-type ATPases transporting non-heavy metal ions. Of particular interest is the SEHPL motif identified in (3) which is absolutely conserved in WD, MNK, and CopA ATPases (2, 3, 8). Striking similarity between evolutionarily remote bacterial heavy metal ATPases and the human WD and MNK genes suggests the functional importance of this motif. Moreover, applicants recently provided population genetic evidence that homozygous mutation of Histidine to Serine within this motif produces the Wilson disease phenotype (3). Although no specific function has been correlated with this region, studies of the sodium, potassium and calcium ATPases provide some clues to the role of this element. Located between the phosphorylation site and the ATP-binding domain (see FIG. 17), the analogous region of Ca-ATPase in the sarcoplasmic reticulum is the site of interaction with phospholamban (27, 28). It is very interesting that phospholamban interacts only with the Ca-free conformation of Ca-ATPase, thereby lowering the apparent affinity for $Ca^{2+}$; as $Ca^{2+}$ concentrations are increased and the ATPase is converted to the $Ca^{2+}$-bound state, phospholamban is released. In the plasma membrane Ca-ATPases the analogous region was shown to be the primary site for interaction with a synthetic calmodulin-binding domain (33). The interaction of calmodulin with the plasma membrane Ca-ATPase results in a 20-fold increase in affinity for calcium (29, 30). In the Na, K-ATPases the analogous region is protected against proteolytic digestion in the presence of sodium, and exposed to hydrolysis when potassium is present (34). In light of these data, it is tempting to speculate that conformational changes at this site represent an essential link between the binding of a cation which stimulates phosphorylation and phosphorylation itself.

Figure 17:
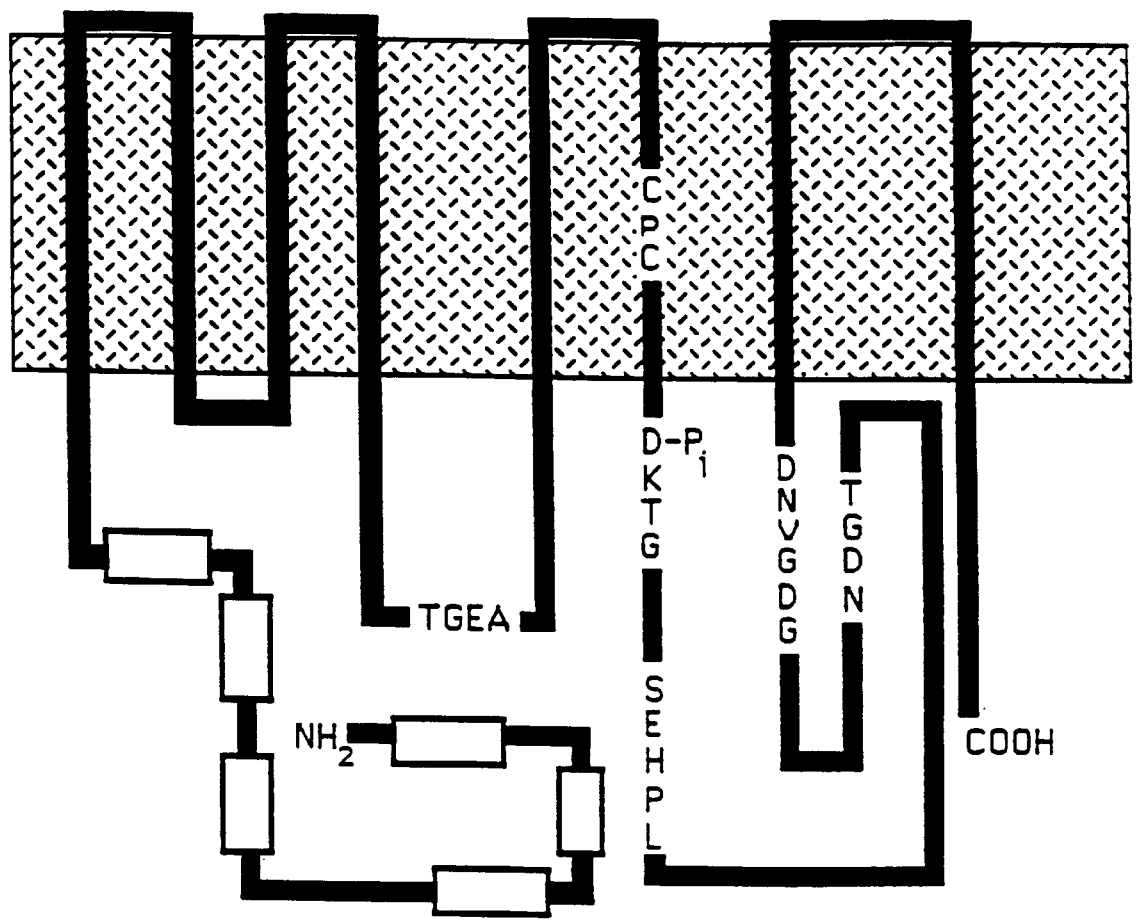
FIG. 17 Schematic model of the WD protein outlining its essential structural features; eight transmembrane crossings, six metal-binding sites (boxes) and characteristic sequences (TGEA (SEQ ID No. 33) represents a transduction domain, D-Pi indicates the putative phosphorylated aspartic acid residue, SEHPL (SEQ ID No. 34) is a novel motif unique to heavy metal transporting ATPases and the site for a frequent disease mutation (3 of the third series of experiments), DNVGDG is a hinge region).

The WD and Menkes disease gene products appear to have only one transmembrane hairpin in the region C-terminal to the hinge domain which contains the sequence DNVGDG (FIG. 17). This is in contrast to other eukaryotic ATPases and some bacterial ATPases (Mg-ATPase of Salmonella for example) which have two or three hairpins in this region of the protein. The structural integrity of these transmembrane segments is essential for the binding of potassium ions by Na,K-ATPase (35) and H,K-ATPase (36). Site-directed mutagenesis of glutamic acid 908 located in the 8th transmembrane fragment of the Ca-ATPase of sarcoplasmic reticulum resulted in complete loss of Ca-transport function and of Ca-dependent phosphorylation (37). These and other data indicate the important role of at least part of the C-terminal domain in formation of the cation transport pathway. It is also interesting to note that KdpB-ATPase of *E. coli* lacks these C-terminal transmembrane fragments and requires other subunits to form a fully functional complex. These data raise the possibility that the WD and Menkes disease genes function in concert with another subunit. The WD gene has been confined to a very restricted genetically defined region by pedigree analysis (3), thus, if there is a second subunit required for normal function and if mutations in this putative subunit were also causal of WD, then its locus would presumably reside in close physical proximity to the WD (ATP7B) locus. In contrast to KdpB-ATPase, cadmium resistance in Staphylococcus aureus relies upon two plasmid-borne determinants, cadA and cadb, although cadA (a cation transporting ATPase) is necessary and sufficient for expression of cadmium resistance (10). Whereas cadB may protect the cell by binding cadmium, cadA alone is sufficient to export excess intracellular $Cd^{2+}$. By comparison, the WD gene product may function independently to transport excess copper, while possibly interacting with other proteins to maintain copper homeostasis. A prime candidate for interaction, either directly or indirectly, is ceruloplasmin. Plasma ceruloplasmin levels are dramatically reduced in 95% of patients with Wilson disease (40), and to a lesser extent in patients with Menkes disease.

Comparison of the WD and MNK gene products with other closely related bacterial heavy metal transporting ATPases reveals several structural differences. First, WD and MNK proteins contain six metal-binding repeats in the N-terminal region as opposed to 1 or 2 in prokaryotic ATPases (2, 4). Second, the WD and MNK gene products encode a rather long (about 100 amino acids) hydrophilic fragment in the very C-terminus of the protein similar to the human Ca-ATPase of plasma membrane and H-ATPase of plants (31). Finally, the length of the sequence from the phosphorylation site to the hinge domain is about 70–80 amino acid residues longer than the corresponding bacterial ATPases, although significantly shorter than the corresponding bacterial ATPases, although significantly shorter than the corresponding region of other eukaryotic ATPases. The amino acid sequence alignment of WD, MNK and CopA ATPases shows that this difference is due to presence of an additional segment immediately following the SEHPH motif. As described above, the region between the phosphorylation and the ATP-binding domains in the Ca-ATPases was shown to be the site for interaction with phospholamban as well as calmodulin, both interactions leading to an increased affinity for calcium. Parasite Ca-ATPases, by contrast, appear to be missing this so-called "phospholamban-binding" sequence (38). In its place the malarial calcium pump has an additional 10–200 amino acids not found in vertebrates, leading to speculation that these molecules might have their own regulatory protein (38). By analogy with these ATPases, applicants suggest that the 70 amino-acid difference between human Cu-ATPase and CopA immediately C-terminal to the SEHPL motif may reflect the unique regulatory requirements of this eukaryotic pump.

References of the Third Series of Experiments

1. Sakar, B. (1981) Transport of copper. In Sigel, H. (ed.), Metal ions in biological systems. Marcel Dekker, New York, pp. 233–281.
2. Tanzi, R, E., Petrukhin, K. Chernov, I., Pellequer, J. L., Wasco, W., Ross, B., Romano, D. M., Parano, E. Pavone, L., Brzustowicz, L. M., Devoto, M., Peppercorn, J., Bush, A. I., Sternlieb, I., Pirastu, M., Gusella, J. F., Ebgrafov, O., Penchaszadeh, G. K., Honig, B., Edelman, I. S., Soares, M. B., Scheinberg, I. H., and Gilliam, T. C. (1993) The Wilson disease gene is a copper transporting ATPase with homology to the Menkes disease gene. *Nature Genet.*, 5:344–350.

3. Petrukhin, K., Fischer, S. G., Pirastu, M., Tanzi, R. E., Chernov, I., Devoto, M., Brzustowicz, L. M., Cayanis, E., Vitale, E., Russo, J. J., Matseoane, D., Boukhgalter, B., Wasco, W., Figus, A. L., Loudianos, J., Cao, A., Sternlieb, I., Evgrafov, O., Parano, E., Pavone, L., Warburton, D., Ott, J., Penchaszadeh, G. K., Scheinberg, I. H., and Gilliam, T. C., (1993) Mapping, cloning and genetic characterization of the region containing the Wilson disease gene. *Nature Genet.* 5:338–343.

4. Bull, P. C., Thomas G. R., Rommens, J. M., Forbes, J. R., and Cox, D. W. (1993) The Wilson disease gene is a putative copper transporting P-type ATPase similar to the Menkes gene. *Nature Genet.*, 5:327–336.

5. Kozak, M. (1991) An analysis of vertebrate mRNA sequences; intimations of translational control *J. Cell Biol.*, 115:887–903.

6. Vulpe, C., Levinson, B., Whitney, S., Packman, S., and Gitschier, J. (1993) Isolation of a candidate gene for Menkes disease and evidence that it encodes a copper-transporting ATPase. *Nature Genet.*, 3:7–13.

7. Breathnach, R., and Chambon, P. (1981) Organization and expression of eucaryotic split genes coding for proteins, *Annu. Rev. Biochem.*, 50:349–383.

8. Odermatt, A., Suter, H., Krapf, R., and Solioz, M. (1993) Primary structure of two P-type ATPases involved in copper homeostasis in Enterococcus hirae. *J. Biol. Chem.*, 268:12775–12777.

9. Kahn, D., David, M., Domergue, O., Daveran, M. -L., Ghai, J., Hirsch, P. R., and Batut, J. (1989) Rhizobium meliloti fixGHI sequence predicts involvement of a specific cation pump in symbiotic nitrogen fixation. *J. Bacteriol.*, 171:929–939.

10. Nucifora, G., Chu, L., Mistra, T. K., and Silver, S. (1989) Cadmium resistance from Staphylococcus aureus plasmid pI258 cadA gene results from a cadmium-effux ATPase. *Proc. Natl Acad. Sci USA*, 86:3544–3548.

11. Vilsen, B., Andersen, J. P., Clarke, D. M., and MacLennan, D. H. (1989) Functional consequences of praline mutations in the cytoplasmic and transmembrane sectors of the $Ca^{2-}$-ATPase of sarcoplasmic reticulum. *J. Biol Chem.*, 264:21024–21030.

12. Lutsenko, S. and Kaplan, J. H. (1994) Molecular events in close proximity to the membrane associated with binding of ligands to the Na,K-ATPase. *J. Biol Chem.*, 269:4555–4565.

13. Mercer, J. F. B., Livingston, J., Hall, B., Paynter, J. A., Begy, C., Chandrasekharappa, S., Lockhart, P., Grimes, A., Bhave, M., Siemieniak, D., and Glover, T. W. (1993) Isolation of a partial candidate gene for Menkes disease by positional cloning. *Nature Genet.*, 3:20–25.

14. Silver, S., Nucifora, G., and Phung, L. T. (1993) Human Menkes X-chromosome disease and the staphylococcal cadmium resistance ATPase: a remarkable similarity in protein sequences. *Mol. Microbiol.*, 10:7–12.

15. Wang, Y., Moore, M., Levinson, H. S., Silver, S., Walsh, C., and Mahler, I. (1989) Nucleotide sequence of a chromosomal mercury resistance determinant from a Bacillus sp. with broad-spectrum mercury resistance. *J. Bacteriol.*, 171:83–92.

16. Burgett, S. G., and Rosteck Jr., P. R. (1994) In Venter, J. C., Adams, M., and Fields, C. (Eds.), (1994) Automated DNA sequencing and Analysis. Academic Press, New York. In press.

17. McKeown, M. (1992) Alternative mRNA splicing. *Annu. Rev. Cell Biol.*, 8:133–155.

18. Bark, S. E., and Shull, G. E. (1992) Structure of the rat plasma membrane $Ca^{2+}$-ATPase isoform 3 gene and characterization of alternative splicing and transcription products. *J. Biol. Chem.*, 267:19683–19690.

19. Strehler, E. E. (1991) Recent advances in the molecular characterization of plasma membrane $Ca^{2+}$ pumps. *J. Membrane Biol.*, 120:1–15.

20. Ovchinnikov, Y. A., Monastyrskaya, G. S., Broude, N. E., Allikments, R. L., Ushkarev, Y. A., Melkov, A. M., Smirnov, Y. V., Malyshev, I. V., Dulubova, I. E., Petrukhin, K. E., Grishin, A. V., Sverdlov, V. E., Kiyatkin, N. I., Kostina, M. B., Modyanov, N. N., and Sverdlov, E. D. (1987) The family of human Na,K-ATPase genes. A partial nucleotide sequence related to the α-subunit. *FEBS Lett.*, 213:73–80.

21. Shull, M. M. Fugh, D. G., and Lingrel, J. B. (1989) Characterization of the human Na,K-ATPase α2 gene and identification of intragenic restriction fragment length polymorphisms. *J. Biol. Chem.*, 264:17532–17543.

22. Newman, P. R., Greeb, J., Keeton, T. P., Reyes, A., and Shull, G. E. (1990) Structure of the human gastric H,K-ATPase gene and comparison of the 5'-flanking sequences of the human and rat genes. *DNA Cell Biol.*, 9:749–762.

23. Zarain-Herzberg, A., MacLennan, D. H. and Perisasamy, M. (1990) Characterization of rabbit cardiac sarco(endo) plasmic reticulum $Ca^{2-}$-ATPase gene. *J. Biol Chem.*, 265:4670–4677.

24. Korezak, B., Zarain-Herzberg, A., Brandl, C. J., Ingles, C. J., Green, N. M., and MacLennan, D. H. (1988) Structure of the rabbit fast-twitch skeletal muscle Ca-ATPase gene. *J. Biol Chem.*, 263:4813–4819.

25. Toyofuku, T., Kurzydlowski, K., Lytton, J., and MacLennan, D. H. (1992) The nucleotide binding/hinge domain plays a crucial role in determining isoform-specific $Ca^{2+}$-dependence of organellar Ca-ATPase. *J. Biol Chem.*, 267:14490–14496.

26. Traut, T. W. (1988) Do exons code for structural or functional units in proteins? *Proc. Natl Acad. Sci. USA*, 84:4767–4771.

27. James, P. Inui, M., Tada, M., Chiesi, M., and Carafoli, E. (1989) Nature and site of phospholamban regulation of the $Ca^{2+}$ pump of sarcoplasmic reticulum. *Nature*, 342:90–92.

28. Toyofuku, T., Kurzydlowski, K., Tada, M., and MacLennan, D. H. (1993) Identification of regions in the Ca-ATPase of sarcoplasmic reticulum that affect functional association with phospholamban. *J. Biol Chem.*, 268:2809–2815.

29. Larsen, F. L. and Vincenzi, (1979) Calcium transport across the plasma membrane: stimulation by calmodulin. *Science*, 204:306–308.

30. Larsen, F. L., Katz, S., and Roufogalis, G. D. (1981) Calmodulin regulation of $Ca^{2+}$ transport in human crythrocytes. *Biochem J.*, 200:185–191.

31. Pardo, J. M., and Serrano, R. (1989) Structure of a plasma membrane $H^+$-ATPase gene from the plant Arabidopsis thaliana. *J. Biol. Chem.*, 264:8557–8562.

32. Lisitsyn, N., Lisitsyn, N. and Wigler, M. (1993) Cloning the differences between two complex genomes. *Science*, 259:946–951.

33. Falchetto, R., Vorherr, T., Brunner J., and Carafoli, E. (1991) The plasma membrane $Ca^{2+}$-pump contains a site that interacts both with calmodulin and with another part of the pump. *J. Biol Chem.*, 266:2930–2936.

34. Jorgensen, P. L. and Farley, R. A. (1988) Proteolytic cleavage as a tool for studying structure and conformation of pure membrane-bound Na,K-ATPase. *Meth Enzymol.*, 156:291–301.

35. Karlish, S. J. D., Goldshleger, R., and Stein, W. D. (1990) A 19 kD C-terminal fragment of the α-chain of Na,K-ATPase is essential for occlusion and transport of cations. *Proc. Natl Acad. Sci.*, 87:4566–4570.
36. Besancon, M., Shin, S. M., Mercier, F., Munson K., Miller, M., Hersey, S., and Sachs, G. (1993) Membrane topology and omeprazole labelling of the gastric H,K-Adenosinetriphosphotase. *Biochemistry*, 32:2345–2355.
37. Clarke, D. M., Loo, T. W., Inesi, G., and MacLennan, D.H. (1989) Location of high affinity $Ca^{2+}$-binding sites within the predicted transmembrane domain of the sarcoplasmic reticulum Ca-ATPase. *Nature*, 339:476–478.
38. Kimura, M., Yamaguchi, Y., Takada, S., and Tanabe, K. (1993) Cloning of a Ca-ATPase gene of Plasmodium falciparum and comparison with vertebrate Ca-ATPase. *J. Cell Sci.*, 104:1129–1136.
39. Kyte, J., and Doolittle, R. F. (1982) A simple method for displaying the hydropathic character of a protein. *J. Mol. Biol.*, 157:105–132.
40. Scheinberg, I. H., and Sternlieb, I. (1984) Wilson's Disease. In Smith Jr., Lloyd H. (ed.), Major Problems in Internal Medicine. Vol. XXIII. W. B. Saunders Company, Philadelphia.
41. MacLennan, D. H., Brandle, C. J., Korezak, B., and Green, N. M. (1985) Amino-acid sequence of a $Ca^{2+}$+ $Mg^{2+}$-dependent ATPase from rabbit muscle sarcoplasmic reticulum, deduced from its complementary DNA sequence. *Nature*, 316:696–700.

What is claimed is:

1. An isolated nucleic acid molecule comprising at least 15 nucleotides which specifically hybridizes to a fragment of a gene which encodes a polypeptide which prevents the development of Wilson's disease, wherein said fragment of a gene has a sequence selected from the group consisting of SEQ ID NOS: 38–78 and SEQ ID NO:79, and wherein hybridization is carried out at 68° C. in 6×SSC, 5× Denhart's solution, 10% dextran sulfate, 20 mM sodium phosphate buffer, pH 7.2, 100 micrograms/ml salmon sperm DNA and 0.2% SDS.

2. A DNA molecule of claim 1.

3. An RNA molecule of claim 1.

4. A host vector system, comprising a vector which comprises the isolated nucleic acid molecule of claim 1 in a host.

5. A vector which comprises the isolated nucleic acid molecule of claim 1.

6. The vector of claim 5, wherein the isolated nucleic acid molecule is linked to a plasmid.

7. An isolated, vertebrate nucleic acid molecule encoding the polypeptide which prevents development of Wilson's disease operatively linked to a promoter of RNA transcription.

8. A host vector system for the production of a polypeptide, comprising a vector which comprises the nucleic acid molecule of claim 7 in a host.

9. A method of producing a polypeptide which comprises growing the host vector system of claim 8 under conditions permitting production of the polypeptide and recovering the polypeptide so produced.

10. An isolated, vertebrate nucleic acid molecule having the nucleic acid sequence set forth in SEQ ID NO: 28 which encodes the polypeptide which prevents development of Wilson's disease.

* * * * *